(12) United States Patent
Altal et al.

(10) Patent No.: US 11,500,461 B2
(45) Date of Patent: Nov. 15, 2022

(54) LIGHT FIELD VISION-BASED TESTING DEVICE, SYSTEM AND METHOD

(71) Applicant: EVOLUTION OPTIKS LIMITED, Christ Church (BB)

(72) Inventors: Faleh Mohammad Faleh Altal, Montreal (CA); Guillaume Lussier, Montreal (CA); Matej Goc, Kingston (CA); Yaiza Garcia, Montreal (CA)

(73) Assignee: EVOLUTION OPTIKS LIMITED, Christ Church (BB)

( * ) Notice: Subject to any disclaimer, the term of this patent is extended or adjusted under 35 U.S.C. 154(b) by 0 days.

(21) Appl. No.: 17/652,656

(22) Filed: Feb. 25, 2022

(65) Prior Publication Data

US 2022/0261072 A1 Aug. 18, 2022

Related U.S. Application Data

(63) Continuation-in-part of application No. 17/510,297, filed on Oct. 25, 2021, which is a continuation of
(Continued)

(51) Int. Cl.
*G06F 3/01* (2006.01)
*G06T 3/40* (2006.01)
(Continued)

(52) U.S. Cl.
CPC ......... *G06F 3/013* (2013.01); *G02B 27/0025* (2013.01); *G06F 3/04845* (2013.01); *G06T 3/40* (2013.01); *G06V 40/19* (2022.01)

(58) Field of Classification Search
CPC ............ G02B 27/0025; G02B 27/0075; G06F 3/013; G06F 3/04845; G06T 3/40;
(Continued)

(56) References Cited

U.S. PATENT DOCUMENTS

| 5,032,754 A | 7/1991 | Iwao et al. |
| 5,959,664 A | 9/1999 | Woodgate |
| 6,192,341 B1 | 2/2001 | Becker et al. |
| 6,309,117 B1 | 10/2001 | Bunce et al. |
| (Continued) | | |

FOREIGN PATENT DOCUMENTS

| AU | 2015100739 | 7/2015 |
| DE | 9410161 U1 | 12/1994 |
| (Continued) | | |

OTHER PUBLICATIONS

U.S. Appl. No. 17/302,392, filed Apr. 30, 2021, Guillaume Lussier.
(Continued)

*Primary Examiner* — Jack Dinh
(74) *Attorney, Agent, or Firm* — Knobbe, Martens, Olson & Bear, LLP

(57) ABSTRACT

Described are various embodiments of a light field vision-based testing device, system and method. One such device comprises an array of digital display pixels; a corresponding array of light field shaping elements (LFSEs); a hardware processor operable to adjust perception of a defined optotype within a range of visual acuity compensations; and an adjustable refractive optical system adjustable to selectively produce a complementary visual acuity compensation to extend each of a cylindrical compensation range and a spherical compensation range.

12 Claims, 51 Drawing Sheets

Related U.S. Application Data application No. PCT/IB2021/051868, filed on Mar. 5, 2021, which is a continuation-in-part of application No. PCT/IB2020/057887, filed on Aug. 22, 2020, and a continuation-in-part of application No. PCT/US2020/058383, filed on Oct. 30, 2020, said application No. PCT/IB2020/057887 is a continuation-in-part of application No. 16/810,143, filed on Mar. 5, 2020, now Pat. No. 10,761,604, said application No. PCT/US2020/058383 is a continuation-in-part of application No. 16/810,143, filed on Mar. 5, 2020, now Pat. No. 10,761,604, application No. 17/652,656, which is a continuation-in-part of application No. PCT/IB2020/057985, filed on Aug. 26, 2020, which is a continuation of application No. 16/854,787, filed on Apr. 21, 2020, now Pat. No. 10,860,099.

(60) Provisional application No. 62/929,639, filed on Nov. 1, 2019.

(51) Int. Cl.
*G02B 27/00* (2006.01)
*G06F 3/04845* (2022.01)
*G06V 40/19* (2022.01)

(58) Field of Classification Search
CPC ........ G06T 5/006; G06V 40/19; G09G 3/001; G09G 3/04; G09G 2354/00; G09G 2360/121; G09G 2380/08
See application file for complete search history.

(56) References Cited

U.S. PATENT DOCUMENTS

| | | |
|---|---|---|
| 6,386,707 B1 | 5/2002 | Pellicano |
| 6,483,485 B1 | 11/2002 | Huang et al. |
| 6,536,907 B1 | 3/2003 | Towner et al. |
| 6,543,898 B1 | 4/2003 | Griffin et al. |
| 6,784,905 B2 | 8/2004 | Brown et al. |
| 6,809,704 B2 | 10/2004 | Kulas |
| 6,820,979 B1 | 11/2004 | Stark et al. |
| 6,876,758 B1 | 4/2005 | Polat et al. |
| 6,953,249 B1 | 10/2005 | Maguire, Jr. |
| 7,062,547 B2 | 6/2006 | Brown et al. |
| 7,147,605 B2 | 12/2006 | Ragauskas |
| 7,517,086 B1 | 4/2009 | Kürkure |
| 7,819,818 B2 | 10/2010 | Ghajar |
| 7,866,817 B2 | 1/2011 | Polat |
| 7,891,813 B2 | 2/2011 | Ogilvie |
| 7,973,850 B2 | 7/2011 | Ishiga |
| 8,089,512 B2 | 1/2012 | Okabe et al. |
| 8,098,440 B2 | 1/2012 | Jethmalani et al. |
| 8,164,598 B2 | 4/2012 | Kimpe |
| 8,231,220 B2 | 7/2012 | Baranton |
| 8,322,857 B2 | 12/2012 | Barbur et al. |
| 8,540,375 B2 | 9/2013 | Destain |
| 8,717,254 B1 | 5/2014 | Nave et al. |
| 8,783,871 B2 | 7/2014 | Pamplona et al. |
| 8,798,317 B2 | 8/2014 | Wu |
| 8,823,742 B2 | 9/2014 | Kweon |
| 8,857,984 B2 | 10/2014 | Clarke et al. |
| 8,967,809 B2 | 3/2015 | Kirschen et al. |
| 9,010,929 B2 | 4/2015 | Lewis |
| 9,041,833 B2 | 5/2015 | Hatakeyama |
| 9,052,502 B2 | 6/2015 | Caldeira et al. |
| 9,066,683 B2 | 6/2015 | Zhou |
| 9,104,233 B2 | 8/2015 | Alberth |
| 9,159,299 B2 | 10/2015 | Lee |
| 9,177,355 B1 | 11/2015 | Buchheit |
| 9,183,806 B2 | 11/2015 | Felt |
| 9,198,571 B2 | 12/2015 | Kiderman et al. |
| 9,301,680 B2 | 4/2016 | Fassi et al. |
| 9,307,940 B2 | 4/2016 | MacLullich et al. |
| 9,492,074 B1 | 11/2016 | Lee et al. |
| 9,642,522 B2 | 5/2017 | Samadani et al. |
| 9,844,323 B2 | 12/2017 | Pamplona et al. |
| 9,895,057 B2 | 2/2018 | Tumlinson |
| 10,058,241 B2 | 8/2018 | Patella et al. |
| 10,085,631 B2 | 10/2018 | Shimizu et al. |
| 10,182,717 B2 | 1/2019 | Lindig et al. |
| 10,206,566 B2 | 2/2019 | Skolianos et al. |
| 10,247,941 B2 | 4/2019 | Fürsich |
| 10,335,027 B2 | 7/2019 | Pamplona et al. |
| 10,345,590 B2 | 7/2019 | Samec et al. |
| 10,394,322 B1 | 8/2019 | Gotsch |
| 10,420,467 B2 | 9/2019 | Krall et al. |
| 10,548,473 B2 | 2/2020 | Escalier et al. |
| 10,761,604 B2 | 9/2020 | Gotsch et al. |
| 2002/0024633 A1 | 2/2002 | Kim et al. |
| 2002/0099305 A1 | 7/2002 | Fukushima et al. |
| 2006/0119705 A1 | 6/2006 | Liao |
| 2007/0247522 A1 | 10/2007 | Holliman |
| 2008/0309764 A1 | 12/2008 | Kubota et al. |
| 2009/0290132 A1 | 11/2009 | Shevlin |
| 2010/0156214 A1 | 6/2010 | Yang |
| 2010/0277693 A1 | 11/2010 | Martinez-Conde et al. |
| 2010/0298735 A1 | 11/2010 | Suffin |
| 2011/0019056 A1 | 1/2011 | Hirsch et al. |
| 2011/0122144 A1 | 5/2011 | Gabay |
| 2011/0157180 A1 | 6/2011 | Burger et al. |
| 2011/0261173 A1 | 10/2011 | Lin et al. |
| 2011/0268868 A1 | 11/2011 | Dowski, Jr. et al. |
| 2012/0010474 A1 | 1/2012 | Olsen et al. |
| 2012/0113389 A1 | 5/2012 | Mukai et al. |
| 2012/0206445 A1 | 8/2012 | Chiba |
| 2012/0249951 A1 | 10/2012 | Hirayama |
| 2012/0254779 A1 | 10/2012 | Ollivierre et al. |
| 2012/0262477 A1 | 10/2012 | Buchheit |
| 2013/0027384 A1 | 1/2013 | Ferris |
| 2013/0096820 A1 | 4/2013 | Agnew |
| 2013/0120390 A1 | 5/2013 | Marchand et al. |
| 2013/0222652 A1 | 8/2013 | Akeley et al. |
| 2014/0028662 A1 | 1/2014 | Liao et al. |
| 2014/0055692 A1 | 2/2014 | Kroll et al. |
| 2014/0063332 A1 | 3/2014 | Miyawaki |
| 2014/0118354 A1 | 5/2014 | Pais et al. |
| 2014/0137054 A1 | 5/2014 | Gandhi et al. |
| 2014/0200079 A1 | 7/2014 | Bathiche et al. |
| 2014/0253876 A1 | 9/2014 | Klin et al. |
| 2014/0267284 A1 | 9/2014 | Blanche et al. |
| 2014/0268060 A1 | 9/2014 | Lee et al. |
| 2014/0282285 A1 | 9/2014 | Sadhvani et al. |
| 2014/0300711 A1 | 10/2014 | Kroon et al. |
| 2014/0327750 A1 | 11/2014 | Malachowsky et al. |
| 2014/0327771 A1 | 11/2014 | Malachowsky et al. |
| 2014/0340390 A1 | 11/2014 | Lanman et al. |
| 2015/0016777 A1 | 1/2015 | Abovitz et al. |
| 2015/0049390 A1 | 2/2015 | Lanman et al. |
| 2015/0177514 A1 | 6/2015 | Maimone et al. |
| 2015/0185501 A1 | 7/2015 | Bakaraju et al. |
| 2015/0234187 A1 | 8/2015 | Lee |
| 2015/0234188 A1 | 8/2015 | Lee |
| 2015/0262424 A1 | 9/2015 | Tabaka et al. |
| 2015/0336511 A1 | 11/2015 | Ukeda |
| 2016/0042501 A1 | 2/2016 | Huang et al. |
| 2016/0103419 A1 | 4/2016 | Callagy et al. |
| 2016/0134815 A1 | 5/2016 | Ishiguro et al. |
| 2016/0260258 A1 | 9/2016 | Lo et al. |
| 2016/0306390 A1 | 10/2016 | Vertegaal et al. |
| 2016/0335749 A1 | 11/2016 | Kano |
| 2017/0027435 A1 | 2/2017 | Boutinon et al. |
| 2017/0060399 A1 | 3/2017 | Hough et al. |
| 2017/0123209 A1 | 5/2017 | Spitzer et al. |
| 2017/0212352 A1 | 7/2017 | Cobb et al. |
| 2017/0227781 A1 | 8/2017 | Banerjee et al. |
| 2017/0302913 A1 | 10/2017 | Tonar et al. |
| 2017/0307898 A1 | 10/2017 | Vdovin et al. |
| 2017/0353717 A1 | 12/2017 | Zhou et al. |
| 2017/0365101 A1 | 12/2017 | Samec et al. |
| 2017/0365189 A1 | 12/2017 | Halpin et al. |
| 2018/0033209 A1 | 2/2018 | Akeley |
| 2018/0070820 A1 | 3/2018 | Fried et al. |

(56) References Cited

U.S. PATENT DOCUMENTS

| | | |
|---|---|---|
| 2018/0084245 A1 | 3/2018 | Lapstun |
| 2018/0136486 A1 | 5/2018 | Macnamara et al. |
| 2018/0203232 A1 | 7/2018 | Bouchier et al. |
| 2018/0252935 A1 | 9/2018 | Vertegaal et al. |
| 2018/0290593 A1 | 10/2018 | Cho |
| 2018/0329485 A1 | 11/2018 | Carothers et al. |
| 2018/0330652 A1 | 11/2018 | Perreault et al. |
| 2019/0094552 A1 | 3/2019 | Shousha |
| 2019/0125179 A1 | 5/2019 | Xu et al. |
| 2019/0150729 A1 | 5/2019 | Huang et al. |
| 2019/0175011 A1 | 6/2019 | Jensen et al. |
| 2019/0228586 A1 | 7/2019 | Bar-Zeev et al. |
| 2019/0246095 A1 | 8/2019 | Kishimoto |
| 2019/0246889 A1 | 8/2019 | Marin et al. |
| 2019/0310478 A1 | 10/2019 | Marin et al. |
| 2020/0012090 A1 | 1/2020 | Lapstun |
| 2020/0272232 A1 | 8/2020 | Lussier et al. |
| 2021/0002557 A1 | 4/2021 | Lussier |
| 2021/0271091 A1 | 9/2021 | Xu et al. |

FOREIGN PATENT DOCUMENTS

| | | |
|---|---|---|
| DE | 102004038822 A1 | 3/2006 |
| DE | 102016212761 | 5/2018 |
| DE | 102018121742 A1 | 3/2020 |
| DE | 102018129600 A1 | 5/2020 |
| DE | 102019102373 A1 | 7/2020 |
| EP | 2127949 A1 | 12/2009 |
| EP | 1509121 B1 | 9/2012 |
| EP | 2589020 A2 | 5/2013 |
| EP | 2678804 A1 | 1/2014 |
| EP | 2760329 A1 | 8/2014 |
| EP | 2999393 A1 | 3/2016 |
| EP | 2547248 B1 | 5/2017 |
| EP | 3262617 A1 | 1/2018 |
| EP | 3313263 A1 | 5/2018 |
| EP | 3339943 A1 | 6/2018 |
| EP | 3367307 A3 | 12/2018 |
| EP | 2828834 B1 | 11/2019 |
| EP | 3620846 A1 | 3/2020 |
| EP | 3631770 A1 | 4/2020 |
| EP | 3657440 A1 | 5/2020 |
| EP | 3659109 A1 | 6/2020 |
| EP | 3689225 A1 | 8/2020 |
| EP | 3479344 B1 | 12/2020 |
| EP | 3313263 A1 | 12/2021 |
| FR | 3059537 B1 | 5/2019 |
| JP | 2003038443 A | 2/2003 |
| WO | 2011156721 A1 | 12/2011 |
| WO | 2013166570 A1 | 11/2013 |
| WO | 2014174168 A1 | 10/2014 |
| WO | 2014197338 A2 | 12/2014 |
| WO | 2015162098 A1 | 10/2015 |
| WO | 2017192887 A2 | 11/2017 |
| WO | 2017218539 A1 | 12/2017 |
| WO | 2018022521 A1 | 2/2018 |
| WO | 2018092989 A1 | 5/2018 |
| WO | 2018129310 A1 | 7/2018 |
| WO | WO2021038421 A1 | 8/2020 |
| WO | WO2021087384 | 10/2020 |
| WO | 2021038430 A1 | 3/2021 |
| WO | 2021122640 A1 | 6/2021 |

OTHER PUBLICATIONS

U.S. Appl. No. 17/309,133, filed Apr. 29, 2021, Daniel Gotsch.
U.S. Appl. No. 62/929,639, filed Nov. 1, 2019, Guillaume Lussier.
"A Computational Light Field Display for Correcting Visual Aberrations," Huang, F.C., Technical Report No. UCB/EECS-2013-206, Electrical Engineering and Computer Sciences University of California at Berkeley, http://www.eecs.berkeley.edu/Pubs/TechRpts/2013/EECS-2013-206.html, Dec. 15, 2013.
Agus M. et al., "GPU Accelerated Direct Volume Rendering on an Interactive Light Field Display", Eurographics 2008, vol. 27, No. 2, 2008.
Burnett T., "FoVI3D Extreme Multi-view Rendering for Light-field Displays", GTC 2018 (GPU Technology Conference), Silicon Valley, 2018.
Ciuffreda, Kenneth J., et al., Understanding the effects of mild traumatic brain injury on the pupillary light reflex, Concussion (2017) 2(3), CNC36.
Fattal, D. et al., A Multi-Directional Backlight for a Wide-Angle, Glasses-Free Three-Dimensional Display, Nature, Mar. 21, 2013, pp. 348-351, vol. 495.
Fielmann Annual Report 2019 (https://www.fielmann.eu/downloads/fielmann_annual_report_2019.pdf).
Gray, Margot, et al., Female adolescents demonstrate greater oculomotor and vestibular dysfunction than male adolescents following concussion, Physical Therapy in Sport 43 (2020) 68-74.
Halle M., "Autostereoscopic displays and computer graphics", Computer Graphics, ACM SIGGRAPH, 31(2), May 1997, pp. 58-62.
Howell, David R., et al., Near Point of Convergence and Gait Deficits in Adolescents After Sport-Related Concussion, Clin J Sport Med, 2017.
Howell, David R., et al., Receded Near Point of Convergence and Gait Are Associated After Concussion, Br J Sports Med, Jun. 2017; 51:e1, p. 9 (Abstract).
Huang, F.C. et al., "Eyeglasses-Free Display: Towards Correcting Visual Aberrations With Computational Light Field Displays,", ACM Transactions on Graphics (TOG)—Proceedings of ACM SIGGRAPH 2014, vol. 33, Issue 4, Article No. 59, Jul. 2014.
Kawata, K., et al., Effect of Repetitive Sub-concussive Head Impacts on Ocular Near Point of Convergence, In t. J Sports Med 2016; 37; 405-410.
Lewin, Sarah "No Need for Reading Glasses With Vision-Correcting Display", published 2014.
Mainone, Andrew, et al. "Focus 3D: Compressive accommodation display." ACM Trans. Graph. 32.5 (2013): 153-1.
Masia B. et al., "A survey on computational displays: Pushing the boundaries of optics, computation, and perception", Computer & Graphics, vol. 37, 2013, pp. 1012-1038.
Murray, Nicholas G., et al., Smooth Pursuit and Saccades after Sport-Related Concussion, Journal of Neurotrauma 36: 1-7 (2019).
Pamplona V. F. et al., "Tailored Displays to Compensate for Visual Aberrations," ACM Transactions on Graphics (TOG), Jul. 2012 Article No. 81, https://doi.org/10.1145/2185520.2185577.
Pamplona V. F., Thesis (Ph.D.)—Universidade Federal do Rio Grande do Sul. Programa de Pós-Graduação em Computação, Porto Alegre, BR-RS, 2012. Advisor: Manuel Menezes de Oliveira Neto.
Ventura, Rachel E., et al., Diagnostic Tests for Concussion: Is Vision Part of the Puzzle?, Journal of Neuro-Ophthalmology 2015; 35; 73-81.
Wetzstein, G. et al., "Tensor Displays: Compressive Light Field Synthesis using Multilayer Displays with Directional Backlighting", https://web.media.mit.edu/~gordonw/TensorDisplays/TensorDisplays.pdf.
Zahid, Abdullah Bin, et al., Eye Tracking as a Biomarker for Concussion in Children, Clin J Sport Med 2018.

replaces 1102

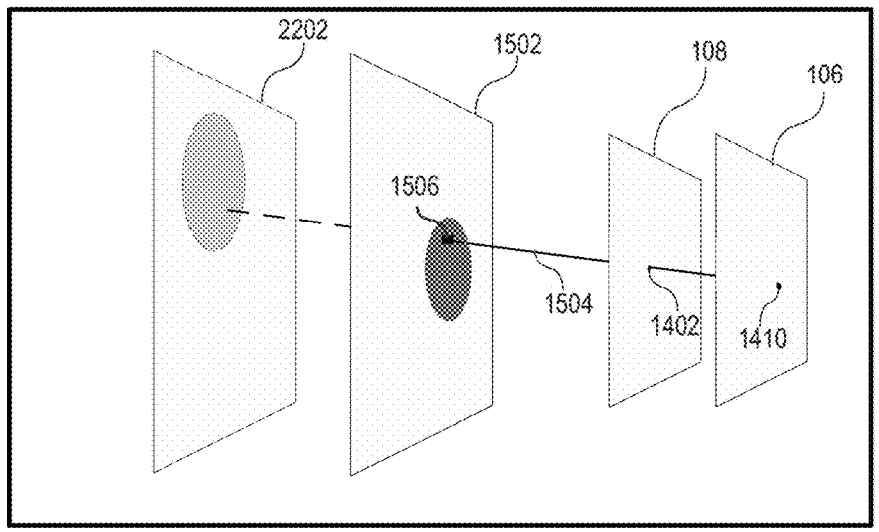
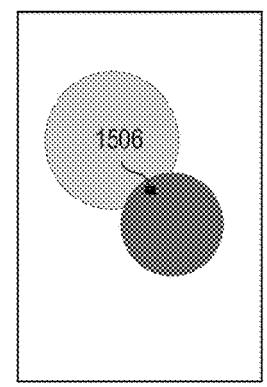
Figure 22B
Figure 22A
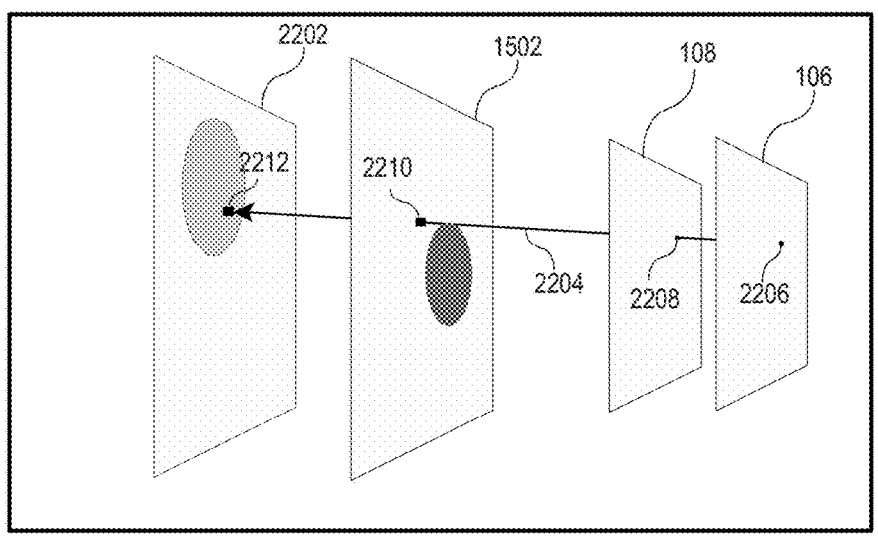
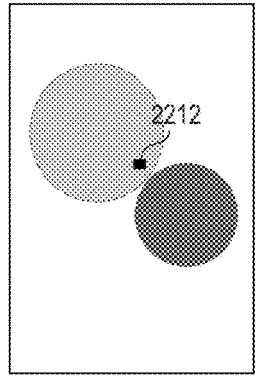
Figure 22D
Figure 22C

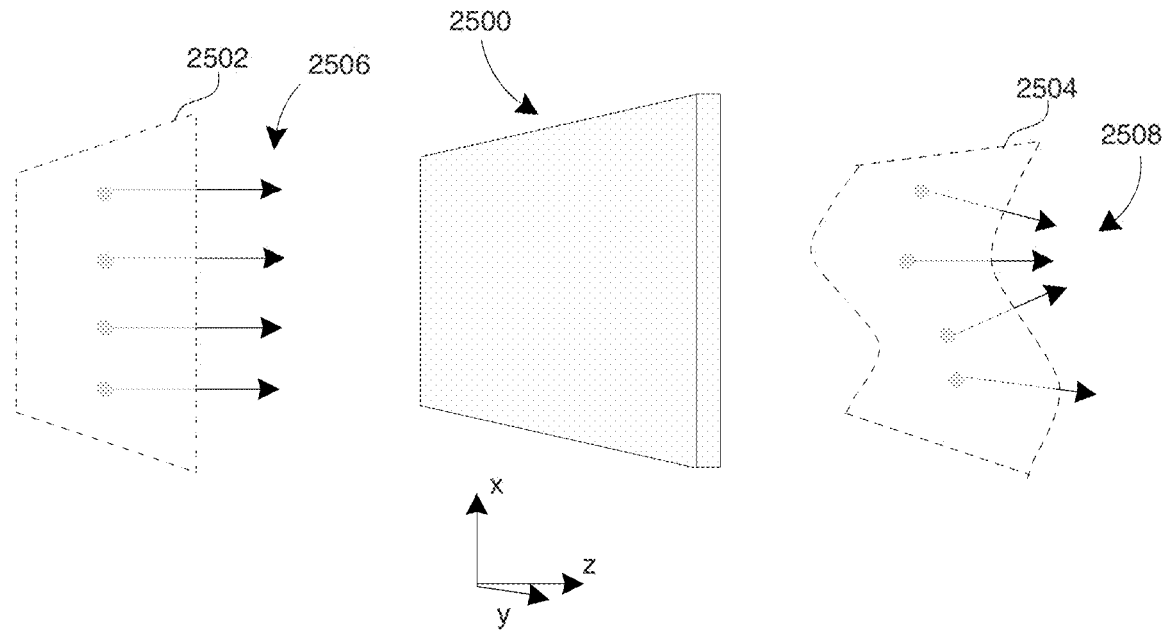
Figure 25
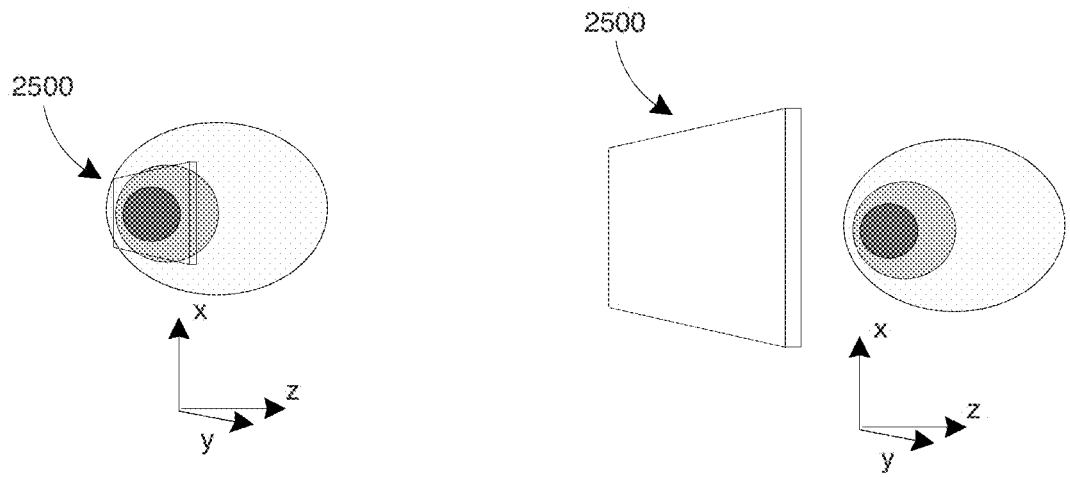
Figure 26A
Figure 26B

LIGHT FIELD VISION-BASED TESTING DEVICE, SYSTEM AND METHOD

CROSS REFERENCE TO RELATED APPLICATIONS

This application is a continuation-in-part of U.S. patent application Ser. No. 17/510,297 filed Oct. 25, 2021, which is a continuation of International Application Serial No. PCT/IB20221/051868 filed Mar. 5, 2021, which is a continuation-in-part of International Application Serial No. PCT/IB2020/057887 filed Aug. 22, 2020 and of International Application Serial No. PCT/US2020/058383 filed Oct. 30, 2020, each of which are a respective continuation-in-part of U.S. patent application Ser. No. 16/810,143 filed Mar. 5, 2020, now U.S. Pat. No. 10,761,604, the entire disclosure of each of which is incorporated herein by reference.

This application is also a continuation-in-part of International Application Serial No. PCT/IB2020/057985 filed Aug. 26, 2020, which is a continuation of U.S. patent application Ser. No. 16/854,787 filed Apr. 21, 2020, now U.S. Pat. No. 10,860,099, and which claims priority to U.S. Provisional Application No. 62/929,639 filed Nov. 1, 2019, the entire disclosure of each of which is incorporated herein by reference.

FIELD OF THE DISCLOSURE

The present disclosure relates to digital displays, and in particular, to a light field vision-based testing device, system and method.

BACKGROUND

Refractive errors such as myopia, hyperopia, and astigmatism affect a large segment of the population irrespective of age, sex and ethnic group. If uncorrected, such errors can lead to impaired quality of life. One method to determine the visual acuity of a person is to use a phoropter to do a subjective vision test (e.g. blur test) which relies on feedback from the subject. The phoropter is used to determine the refractive power needed to bring any projected image to focus sharply onto the retina. A traditional phoropter is usually coupled with a screen or a chart where optotypes are presented, for example a Snellen chart. A patient is asked to look through the instrument to a chart placed at optical infinity, typically equivalent to 6 m/20 feet. Then he/she will be asked about the letters/symbols presented on the screen, and whether he/she is able to differentiate/resolve the letters. The patient will keep looking at letters of smaller size or higher resolution power until there is no improvement, at that time the eye-care practitioner is able to determine the visual acuity (VA) of the subject and proceed with the other eye.

Light field displays are known to adjust a user's perception of an input image by adjusting a light field emanated by the display so to control how a light field image is ultimately projected for viewing. For instance, in some examples, users who would otherwise require corrective eyewear such as glasses or contact lenses, or again bifocals, may consume images produced by such devices in clear or improved focus without the use of such eyewear. Other light field display applications, such as 3D displays, are also known.

This background information is provided to reveal information believed by the applicant to be of possible relevance. No admission is necessarily intended, nor should be construed, that any of the preceding information constitutes prior art or forms part of the general common knowledge in the relevant art.

SUMMARY

The following presents a simplified summary of the general inventive concept(s) described herein to provide a basic understanding of some aspects of the disclosure. This summary is not an extensive overview of the disclosure. It is not intended to restrict key or critical elements of embodiments of the disclosure or to delineate their scope beyond that which is explicitly or implicitly described by the following description and claims.

A need exists for a light field vision-based testing device, system and method that overcome some of the drawbacks of known technology, or at least, provide a useful alternative thereto. Examples of light field vision-based testing devices, systems and methods are provided herein.

In accordance with one aspect, there is provided a subjective eye test device comprising: an array of digital display pixels; a corresponding array of light field shaping elements (LFSEs) disposed to shape a light field emanating from said pixels toward a user pupil location; a hardware processor operable on pixel data for a defined optotype to output adjusted pixel data to be rendered via said LFSEs to adjust perception of said defined optotype at the user pupil location within a range of visual acuity compensations, wherein said range of visual acuity compensations comprises a cylindrical compensation range and a spherical compensation range; and an adjustable refractive optical system interposed to intercept said light field and adjustable to selectively produce a complementary visual acuity compensation to extend each of said cylindrical compensation range and said spherical compensation range; wherein said hardware processor and said adjustable refractive optical system are operable to adjust said perception of said defined optotype until an optimal spherical visual acuity compensation and an optimal cylindrical visual acuity compensation are subjectively identified.

In one embodiment, the adjustable refractive optical system comprises an electrically tunable lens.

In one embodiment, the electrically tunable lens comprises a pair of spherically tunable lenses.

In one embodiment, the adjustable refractive optical system comprises a tunable cylindrical lens tunable to extend said cylindrical compensation range.

In one embodiment, the tunable cylindrical lens comprises a pair of cylindrical lenses, wherein an angular offset of said pair of cylindrical lenses is tunable to extend said cylindrical compensation range.

In one embodiment, the adjustable refractive optical system is operable to set a coarse visual acuity compensation value within a broader course visual acuity compensation range, whereas said hardware processor is operable to fine-tune said coarse visual acuity compensation value within a narrower visual acuity compensation range around said coarse visual acuity compensation value until said optimal spherical and cylindrical visual acuity compensation is subjectively identified.

In one embodiment, the adjustable refractive optical system comprises an adjustable spherical lens to set a coarse spherical visual acuity compensation and an adjustable cylindrical lens to set a coarse cylindrical visual acuity compensation.

In one embodiment, a total visual acuity compensation power is composed of a coarse visual acuity compensation power produced by said adjustable refractive optical system, and a fine visual acuity compensation power produced by said hardware processor operating on said pixel data.

In one embodiment, the hardware processor is operable on said pixel data to simultaneously render at least two said defined optotype side-by-side in accordance with respective visual acuity compensations within said narrower visual acuity compensation range for subjective comparison.

In one embodiment, the at least two said defined optotype are rendered to present distinct levels of correction for a same optotype.

In one embodiment, the defined optotype comprises multiple optotypes varying in size and displayed simultaneously according to a same visual acuity compensation.

In one embodiment, the optimal cylindrical visual acuity compensation compensates for astigmatism.

In accordance with another aspect, there is provided a computer-implemented subjective eye test method, implemented by one or more digital processors, comprising: rendering a defined optotype via an array of digital display pixels and a corresponding array of light field shaping elements (LFSEs) disposed to shape a light field emanating from said pixels toward a user pupil location; setting a coarse visual acuity compensation via an adjustable refractive optical system interposed to intercept said light field, to a coarse visual acuity compensation value; digitally adjusting perception of said defined optotype within a fine-tuning range around said coarse visual acuity compensation value by dynamically adjusting pixel data for said defined optotype to be rendered via said LFSEs in producing a fine-tuning visual acuity compensation, until an optimal visual acuity compensation is subjectively defined; wherein said coarse visual acuity compensation and said fine-tuning visual acuity compensation each respectively comprise at least a coarse cylindrical compensation and a fine-tuning cylindrical compensation.

In one embodiment, the coarse spherical visual acuity compensation and a fine-tuning spherical visual acuity compensation are first subjectively identified, before said coarse cylindrical compensation and said fine-tuning cylindrical compensation are subjectively identified.

In one embodiment, the rendering comprises rendering at least two defined optotypes side-by-side; wherein said coarse visual acuity compensation is set uniformly to each of said at least two defined optotypes; whereas respective fine-tuning visual acuity compensations are simultaneously set for each of said at least two defined optotypes for comparative purposes in subjectively identifying said optimal visual acuity compensation.

In one embodiment, the setting a coarse visual acuity compensation comprises setting offset rotation angles between cylindrical lenses disposed to intercept said light field.

In one embodiment, the setting a coarse visual acuity compensation comprises setting a coarse spherical compensation via variable spherical optics, and setting a coarse cylindrical compensation via distinct variable cylindrical optics.

In one embodiment, the variable spherical optics comprise an electrically tunable spherical lens.

In one embodiment, the digitally adjusting comprises, for each given pixel of at least some of said digital display pixels: digitally projecting an adjusted image ray trace from said given pixel towards the user pupil location, given a corresponding LFSE corresponding thereto, to intersect a virtual phase element digitally defined to virtually produce a designated optical phase shift corresponding to said fine-tuning cylindrical compensation; digitally projecting a refracted ray trace refracted by said virtual phase element to intersect an adjusted image plane location on a designated adjusted image plane; associating with said given pixel an adjusted image value designated for said adjusted image location; and rendering for each said given pixel said adjusted image value associated therewith.

In one embodiment, the cylindrical fine-tuning cylindrical visual acuity compensation is defined by a cylindrically variable optical aberration parameter; wherein said digitally adjusting comprises, for each given pixel of at least some of said digital display pixels: defining a corresponding location on an adjusted image surface as a function of a direction of a given light field emanated by said given pixel given a corresponding LFSE and given value for said cylindrically variable optical aberration for a given pupil location intersected by said given light field; associating an adjusted image pixel value with said given pixel given said corresponding location on said adjusted image surface; and rendering each said given pixel according to said adjusted pixel value associated therewith, thereby perceptively rendering a perceptively adjusted version of the input image that at least partially accommodates said cylindrically variable optical aberration.

In one embodiment, the fine-tuning cylindrical compensation corresponds with an astigmatism compensation.

In one embodiment, the total visual acuity compensation power is composed of a coarse visual acuity compensation power and a fine visual acuity compensation power.

Other aspects, features and/or advantages will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIGS. 22A to 22D are schematic diagrams illustrating certain process steps of FIGS. 21A and 21B, in accordance with one embodiment;

FIG. 25 is a schematic diagram of an exemplary virtual phase element for simulating optical aberrations, including higher order aberrations (HOAs), in accordance with one embodiment;

FIGS. 26A and 26B are schematic diagrams illustrating how a phase element of FIG. 25 may be used to simulate aberrations, including HOAs, in the eye (26A) or in a phase element located in front of the eye (20B), in accordance with one embodiment;

Figure 1A:
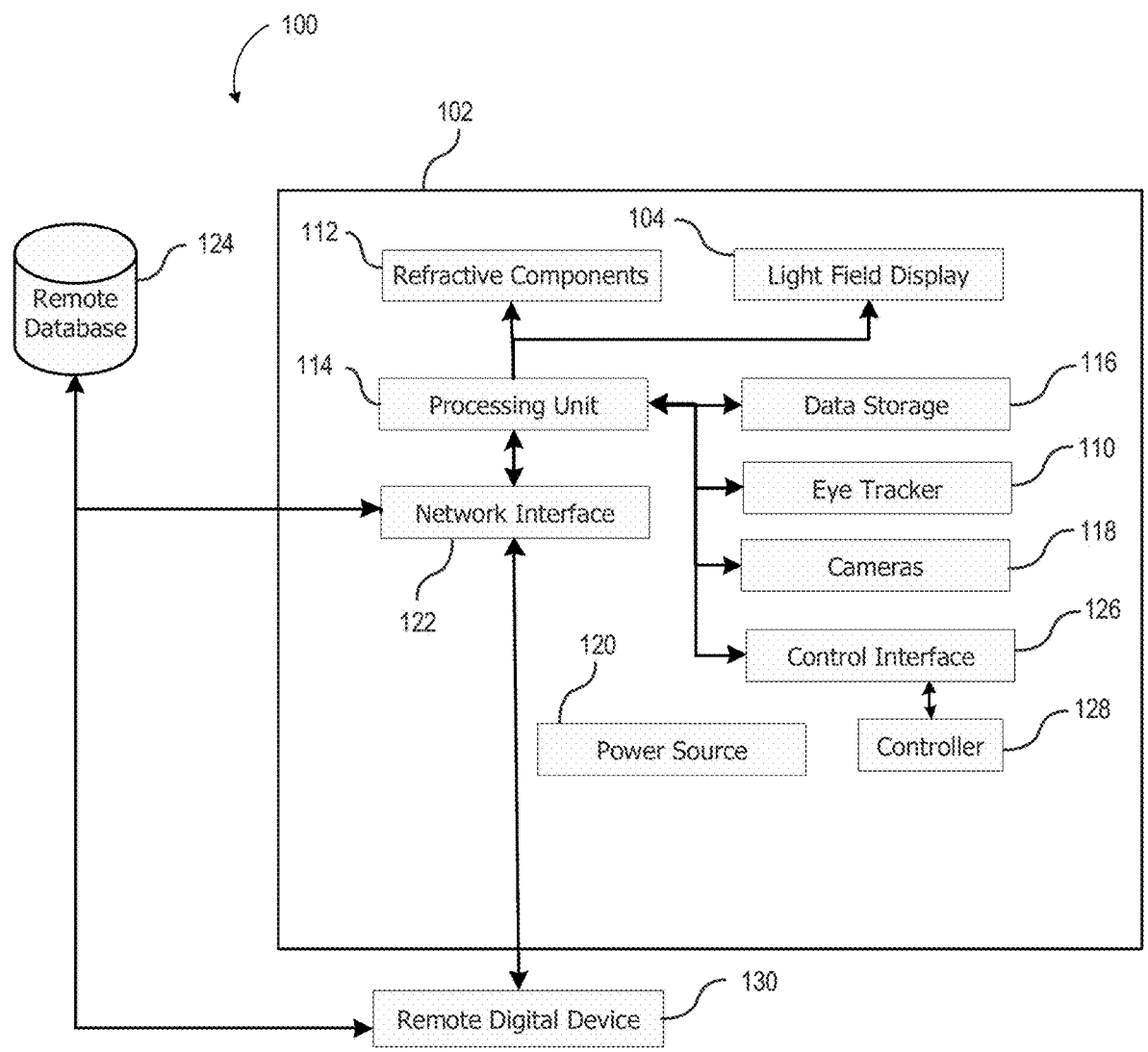
FIGS. 1A and 1B are schematic diagrams of an exemplary light field vision testing or previewing system, in accordance with one embodiment.

Elements in the several figures are illustrated for simplicity and clarity and have not necessarily been drawn to scale. For example, the dimensions of some of the elements in the figures may be emphasized relative to other elements for facilitating understanding of the various presently disclosed embodiments. Also, common, but well-understood elements that are useful or necessary in commercially feasible embodiments are often not depicted in order to facilitate a less obstructed view of these various embodiments of the present disclosure.

DETAILED DESCRIPTION

Various implementations and aspects of the specification will be described with reference to details discussed below. The following description and drawings are illustrative of the specification and are not to be construed as limiting the specification. Numerous specific details are described to provide a thorough understanding of various implementations of the present specification. However, in certain instances, well-known or conventional details are not described in order to provide a concise discussion of implementations of the present specification.

Various apparatuses and processes will be described below to provide examples of implementations of the system disclosed herein. No implementation described below limits any claimed implementation and any claimed implementations may cover processes or apparatuses that differ from those described below. The claimed implementations are not limited to apparatuses or processes having all of the features of any one apparatus or process described below or to features common to multiple or all of the apparatuses or processes described below. It is possible that an apparatus or process described below is not an implementation of any claimed subject matter.

Furthermore, numerous specific details are set forth in order to provide a thorough understanding of the implementations described herein. However, it will be understood by those skilled in the relevant arts that the implementations described herein may be practiced without these specific details. In other instances, well-known methods, procedures and components have not been described in detail so as not to obscure the implementations described herein.

In this specification, elements may be described as "configured to" perform one or more functions or "configured for" such functions. In general, an element that is configured to perform or configured for performing a function is enabled to perform the function, or is suitable for performing the function, or is adapted to perform the function, or is operable to perform the function, or is otherwise capable of performing the function.

It is understood that for the purpose of this specification, language of "at least one of X, Y, and Z" and "one or more of X, Y and Z" may be construed as X only, Y only, Z only, or any combination of two or more items X, Y, and Z (e.g., XYZ, XY, YZ, ZZ, and the like). Similar logic may be applied for two or more items in any occurrence of "at least one . . . " and "one or more . . . " language.

Unless defined otherwise, all technical and scientific terms used herein have the same meaning as commonly understood by one of ordinary skill in the art to which this invention belongs.

Throughout the specification and claims, the following terms take the meanings explicitly associated herein, unless the context clearly dictates otherwise. The phrase "in one of the embodiments" or "in at least one of the various embodiments" as used herein does not necessarily refer to the same embodiment, though it may. Furthermore, the phrase "in another embodiment" or "in some embodiments" as used herein does not necessarily refer to a different embodiment, although it may. Thus, as described below, various embodiments may be readily combined, without departing from the scope or spirit of the innovations disclosed herein.

In addition, as used herein, the term "or" is an inclusive "or" operator, and is equivalent to the term "and/or," unless the context clearly dictates otherwise. The term "based on" is not exclusive and allows for being based on additional factors not described, unless the context clearly dictates otherwise. In addition, throughout the specification, the meaning of "a," "an," and "the" include plural references. The meaning of "in" includes "in" and "on."

As used in the specification and claims, the singular forms "a", "an" and "the" include plural references unless the context clearly dictates otherwise.

The term "comprising" as used herein will be understood to mean that the list following is non-exhaustive and may or may not include any other additional suitable items, for example one or more further feature(s), component(s) and/or element(s) as appropriate.

The methods and systems described herein are directed, according to different embodiments, to light field rendering methods and systems capable of compensating for, or simulating, the presence of one or more optical aberrations, including higher order aberrations (HOAs), in, or disposed in relation to, a user's eye so to present a corrected, simulating or compensating image thereto. The methods and systems discussed below, in accordance with different embodiments, make use of a "virtual" optical element or phase element specifically tailored or defined so as to correctly reproduce or simulate the presence of these one or more aberrations.

For instance, a higher order aberration, as compared to lower zero, first or second-order aberrations, can often be defined by one or more polynomial functions that, alone or in combination, can be used to define a refractive response resulting from the higher order aberration. Examples of higher order aberrations may include, but are not limited to, trefoil, coma, and spherical aberrations that may result in poor night vision, glare, halos, blurring, starburst patterns or double vision. In these or other embodiments, lower order aberrations, such as those common to astigmatism (e.g. defined by cylindrical and axis parameters), myopia or hyperopia (e.g. defined by limited or constrained eye focus parameters), may be addressed, simulated or compensated for using the embodiments described herein, and that, independently or in combination. As such, addressed aberrations may be decomposed into lower and/or higher order aberrations as defined by respective or combined aberration parameters, whereby some may be otherwise addressed by alternate methods (e.g. within the simplified context of lower order aberrations), whereas other aberrations may be defined by complementary aberration parameters (e.g. higher order aberration parameters, etc.) and specifically addressed by the methods and approaches described herein. As such, in combination, all aberration parameters may be effectively addressed or simulated. These and other such considerations will become further apparent to the skilled artisan upon reading of the following illustrative examples.

As will be further described below, the herein described methods and systems may be equally applied to vision correction and/or for vision testing applications. For example, devices, displays and methods described herein may allow a user's perception of one or more input images (or input image portions), where each image or image portion is virtually located or perceived to be at a distinct image plane/depth location, to be adjusted or altered using the described light field display technology, again allowing for corrective assessment and/or previewing capabilities in respect of this viewer's reduced visual acuity or aberrations.

Some of the herein described embodiments provide for digital display devices, or devices encompassing such displays, for use by users having reduced visual acuity, whereby images ultimately rendered by such devices can be dynamically processed to accommodate the user's reduced visual acuity so that they may more comfortably consume rendered images without the use of corrective eyewear, contact lenses, or surgical intervention, as would otherwise be required. As noted above, embodiments are not to be limited as such as the notions and solutions described herein may also be applied to other technologies in which a user's perception of an input image to be displayed can be altered or adjusted via the light field display. Again, similar implementation of the herein described embodiments can allow for implementation of digitally adaptive vision tests or corrective or adaptive vision previews or simulations such that individuals with such reduced visual acuity can be exposed to distinct perceptively adjusted versions of an input image(s) to subjectively ascertain a potentially required or preferred vision correction.

Generally, digital displays as considered herein will comprise a set of image rendering pixels and a corresponding set of light field shaping elements that at least partially govern a light field emanated thereby to produce a perceptively adjusted version of the input image, notably distinct perceptively adjusted portions of an input image or input scene, which may include distinct portions of a same image, a same 2.5D/3D scene, or distinct images (portions) associated with different image depths, effects and/or locations and assembled into a combined visual input. For simplicity, the following will generally consider distinctly addressed portions or segments as distinct portions of an input image, whether that input image comprises a singular image having distinctly characterized portions, a digital assembly of distinctly characterized images, overlays, backgrounds, foregrounds or the like, or any other such digital image combinations.

In some examples, light field shaping elements may take the form of a light field shaping layer or like array of optical elements to be disposed relative to the display pixels in at least partially governing the emanated light field. As described in further detail below, such light field shaping layer elements may take the form of a microlens and/or pinhole array, or other like arrays of optical elements, or again take the form of an underlying light field shaping layer, such as an underlying array of optical gratings or like optical elements operable to produce a directional pixelated output.

Within the context of a light field shaping layer, as described in further detail below in accordance with some embodiments, the light field shaping layer can be disposed at a pre-set distance from the pixelated display so to controllably shape or influence a light field emanating therefrom. For instance, each light field shaping layer can be defined by an array of optical elements centered over a corresponding subset of the display's pixel array to optically influence a light field emanating therefrom and thereby govern a projection thereof from the display medium toward the user, for instance, providing some control over how each pixel or pixel group will be viewed by the viewer's eye(s). As will be further detailed below, arrayed optical elements may include, but are not limited to, lenslets, microlenses or other such diffractive optical elements that together form, for example, a lenslet array; pinholes or like apertures or windows that together form, for example, a parallax or like barrier; concentrically patterned barriers, e.g. cut outs and/or windows, such as a to define a Fresnel zone plate or optical sieve, for example, and that together form a diffractive optical barrier (as described, for example, in Applicant's co-pending U.S. application Ser. No. 15/910,908, the entire contents of which are hereby incorporated herein by reference); and/or a combination thereof, such as for example, a lenslet array whose respective lenses or lenslets are partially shadowed or barriered around a periphery thereof so to combine the refractive properties of the lenslet with some of the advantages provided by a pinhole barrier.

In operation, the display device will also generally invoke a hardware processor operable on image pixel (or subpixel) data for an image to be displayed to output corrected or adjusted image pixel data to be rendered as a function of a stored characteristic of the light field shaping elements and/or layer (e.g. layer distance from display screen, distance between optical elements (pitch), absolute relative location of each pixel or subpixel to a corresponding optical element, properties of the optical elements (size, diffractive and/or refractive properties, etc.), or other such properties, and a selected vision correction or adjustment parameter related to the user's reduced visual acuity or intended viewing experience. While light field display characteristics will generally remain static for a given implementation (i.e. a given shaping element and/or layer will be used and set for each device irrespective of the user), image processing can, in some embodiments, be dynamically adjusted as a function of the user's visual acuity or intended application so to actively adjust a distance of a virtual image plane, or perceived image on the user's retinal plane given a quantified user eye focus or like optical aberration(s), induced upon rendering the corrected/adjusted image pixel data via the static optical layer and/or elements, for example, or otherwise actively adjust image processing parameters as may be considered, for example, when implementing a viewer-adaptive pre-filtering algorithm or like approach (e.g. compressive light field optimization), so to at least in part govern an image perceived by the user's eye(s) given pixel or subpixel-specific light visible thereby through the layer.

Figure 1B:
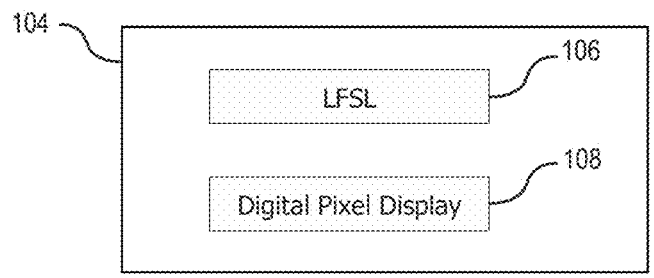

With reference to FIGS. 1A and 1B, and in accordance with different embodiments, an exemplary subjective vision testing device/system (interchangeably referred to as a corrective vision previewing device/system), generally referred to using the numeral 100, will now be described. At the heart of this system is a light field vision testing device such as a light field refractor or phoropter device 102. Generally, light field refractor 102 is a device comprising, as mentioned above, a light field display 104 and which is operable to display or generate one or more images, including optotypes, to a user or patient having his/her vision acuity (e.g. refractive error) tested.

In some embodiments, as illustrated in FIG. 1B, light field display 104 comprises a light field shaping layer (LFSL) 108 overlaid or placed in front of a digital pixel display 110 (i.e. LCD, LED, OLED, etc.). For the sake of illustration, the following embodiments will be described within the context of a LFSL 108 defined, at least in part, by a lenslet array comprising an array of microlenses (also interchangeably referred to herein as lenslets) that are each disposed at a distance from a corresponding subset of image rendering pixels in an underlying digital display. It will be appreciated that while a light field shaping layer may be manufactured and disposed as a digital screen overlay, other integrated concepts may also be considered, for example, where light field shaping elements are integrally formed or manufactured within a digital screen's integral components such as a textured or masked glass plate, beam-shaping light sources (e.g. directional light sources and/or backlit integrated optical grating array) or like component.

Accordingly, each lenslet will predictively shape light emanating from these pixel subsets to at least partially govern light rays being projected toward the user by the display device. As noted above, other light field shaping layers may also be considered herein without departing from the general scope and nature of the present disclosure, whereby light field shaping will be understood by the person of ordinary skill in the art to reference measures by which light, that would otherwise emanate indiscriminately (i.e. isotropically) from each pixel group, is deliberately controlled to define predictable light rays that can be traced between the user and the device's pixels through the shaping layer.

For greater clarity, a light field is generally defined as a vector function that describes the amount of light flowing in every direction through every point in space. In other words, anything that produces or reflects light has an associated light field. The embodiments described herein produce light fields from an object that are not "natural" vector functions one would expect to observe from that object. This gives it the ability to emulate the "natural" light fields of objects that do not physically exist, such as a virtual display located far behind the light field display.

Figure 2A:
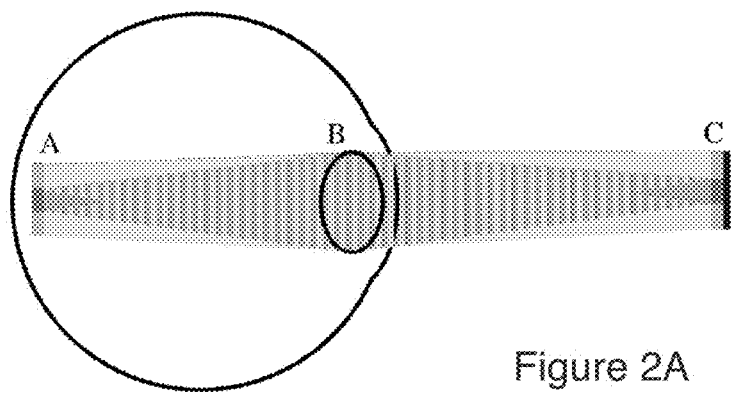
FIGS. 2A to 2C schematically illustrate normal vision, blurred vision, and corrected vision in accordance with one embodiment, respectively.
Figure 2B:
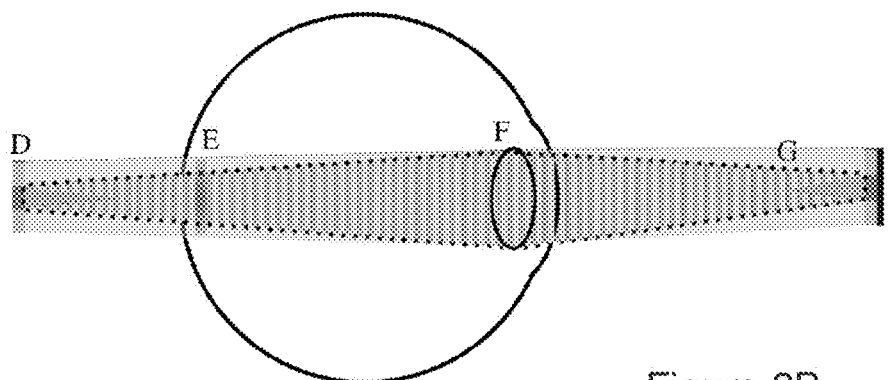

In one example, to apply this technology to vision correction, consider first the normal ability of the lens in an eye, as schematically illustrated in FIG. 2A, where, for normal vision, the image is to the right of the eye (C) and is projected through the lens (B) to the retina at the back of the eye (A). As comparatively shown in FIG. 2B, the poor lens shape and inability to accommodate (F) in presbyopia causes the image to be focused past the retina (D) forming a blurry image on the retina (E). The dotted lines outline the path of a beam of light (G). Naturally, other optical aberrations present in the eye will have different impacts on image formation on the retina. To address these aberrations, a light field display 104, in accordance with some embodiments, projects the correct sharp image (H) on the retina for an eye with a crystalline lens which otherwise could not accommodate sufficiently to produce a sharp image. The other two light field pixels (I) and (J) are drawn lightly, but would otherwise fill out the rest of the image.

Figure 2C:
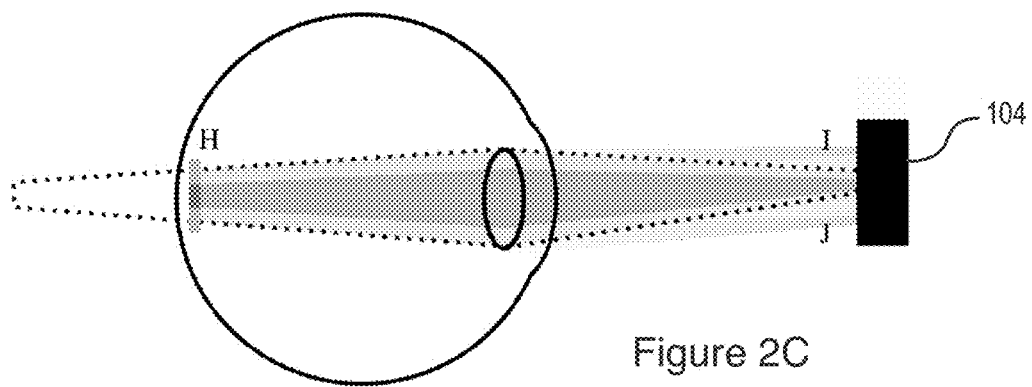
Figure 3A:
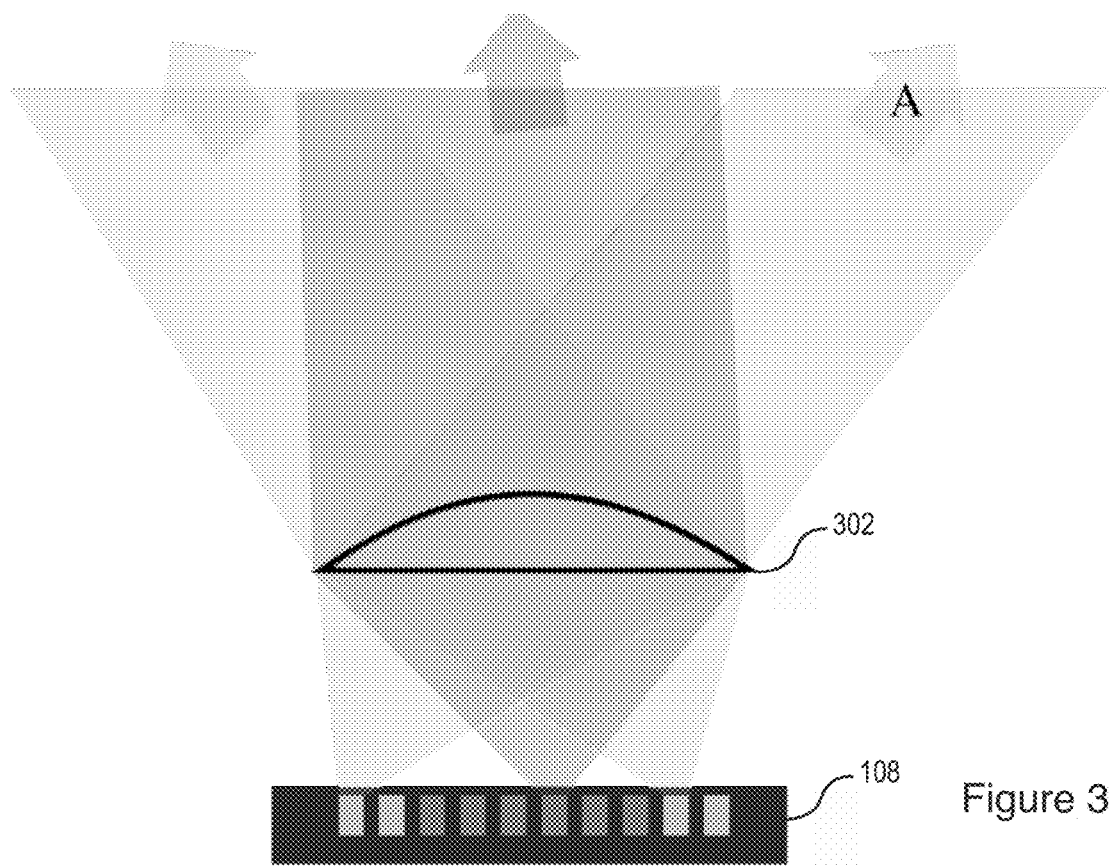
FIGS. 3A and 3B are schematic diagrams of a light field display in which respective pixel subsets are aligned to emit light through a corresponding microlens or lenslet, in accordance with one embodiment.

As will be appreciated by the skilled artisan, a light field as seen in FIG. 2C cannot be produced with a 'normal' two-dimensional display because the pixels' light field emits light isotropically. Instead it is necessary to exercise tight control on the angle and origin of the light emitted, for example, using a microlens array or other light field shaping layer such as a parallax barrier, or combination thereof. Following with the example of a microlens array for LFSL 106, FIG. 3A schematically illustrates a single light field pixel defined by a convex microlens 302 disposed at its focus from a corresponding subset of pixels in a digital pixel display 108 to produce a substantially collimated beam of light emitted by these pixels, whereby the direction of the beam is controlled by the location of the pixel(s) relative to the microlens. The single light field pixel produces a beam similar to that shown in FIG. 2C where the outside rays are lighter and the majority inside rays are darker. The digital pixel display 108 emits light which hits the microlens 302 and it results in a beam of substantially collimated light (A).

Figure 3B:
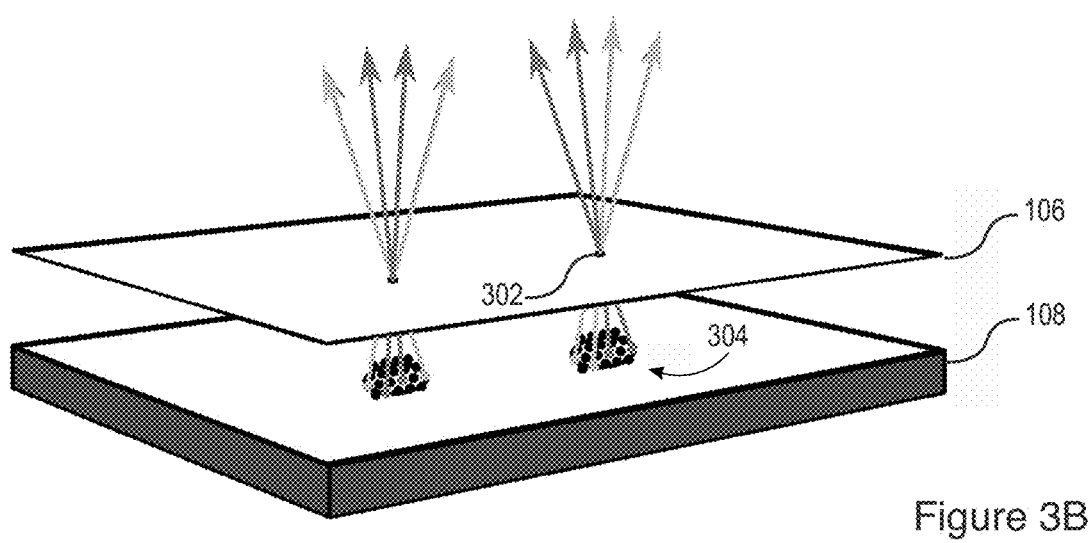

Accordingly, upon predictably aligning a particular microlens array with a pixel array, a designated "circle" of pixels will correspond with each microlens and be responsible for delivering light to the pupil through that lens. FIG. 3B schematically illustrates an example of a light field display assembly in which a LFSL 106 sits above a pixel display 108 to have pixels 304 emit light through the microlens array. A ray-tracing algorithm can thus be used to produce a pattern to be displayed on the pixel array below the microlens in order to create the desired virtual image that will effectively correct for the viewer's reduced visual acuity.

As will be detailed further below, the separation between the LFSL 106 and the pixel array 108 as well as the pitch of the lenses can be selected as a function of various operating characteristics, such as the normal or average operating distance of the display, and/or normal or average operating ambient light levels.

In some embodiments, LFSL 106 may be a microlens array (MLA) defined by a hexagonal array of microlenses or lenslet disposed so to overlay a corresponding square pixel array of digital pixel display 108. In doing so, while each microlens can be aligned with a designated subset of pixels to produce light field pixels as described above, the hexagonal-to-square array mismatch can alleviate certain periodic optical artifacts that may otherwise be manifested given the periodic nature of the optical elements and principles being relied upon to produce the desired optical image corrections. Conversely, a square microlens array may be favoured when operating a digital display comprising a hexagonal pixel array.

In some embodiments, the MLA may further or alternatively be overlaid or disposed at an angle (rotation) relative to the underlying pixel array, which can further or alternatively alleviate period optical artifacts.

In yet some further or alternative embodiments, a pitch ratio between the microlens array and pixel array may be deliberately selected to further or alternatively alleviate periodic optical artifacts. For example, a perfectly matched pitch ratio (i.e. an exact integer number of display pixels per microlens) is most likely to induce periodic optical artifacts, whereas a pitch ratio mismatch can help reduce such occurrences.

Accordingly, in some embodiments, the pitch ratio will be selected to define an irrational number, or at least, an irregular ratio, so to minimize periodic optical artifacts. For instance, a structural periodicity can be defined so to reduce the number of periodic occurrences within the dimensions of the display screen at hand, e.g. ideally selected so to define a structural period that is greater than the size of the display screen being used.

While this example is provided within the context of a microlens array, similar structural design considerations may be applied within the context of a parallax barrier, diffractive barrier or combination thereof. In some embodiments, light field display 104 can render dynamic images at over 30 frames per second on the hardware in a smartphone.

Accordingly, a display device as described above and further exemplified below, can be configured to render a corrected or adjusted image via the light field shaping layer that accommodates, tests or simulates for the user's visual acuity. By adjusting the image correction in accordance with the user's actual predefined, set or selected visual acuity level, different users and visual acuity may be accommodated using a same device configuration, whereas adjusting such parameters for a given user may allow for testing for or simulation of different corrective or visual adjustment solutions. For example, by adjusting corrective image pixel data to dynamically adjust a virtual image distance below/above the display as rendered via the light field shaping layer, different visual acuity levels may be accommodated, and that, for an image input as a whole, for distinctly various portions thereof, or again progressively across a particular input.

As noted in the examples below, in some embodiments, light field rendering may be adjusted to effectively generate a virtual image on a virtual image plane that is set at a designated distance from an input user pupil location, for example, so to effectively push back, or move forward, a perceived image, or portion thereof, relative to the light field refractor device 102. In yet other embodiments, light field rendering may rather or alternatively seek to map the input image on a retinal plane of the user, taking into account visual aberrations, so to adaptively adjust rendering of the input image on the display device to produce the mapped effect. Namely, where the unadjusted input image would otherwise typically come into focus in front of or behind the retinal plane (and/or be subject to other optical aberrations), this approach allows to map the intended image on the retinal plane and work therefrom to address designated optical aberrations accordingly. Using this approach, the device may further computationally interpret and compute virtual image distances tending toward infinity, for example, for extreme cases of presbyopia. This approach may also more readily allow, as will be appreciated by the below description, for adaptability to other visual aberrations that may not be as readily modeled using a virtual image and image plane implementation. In both of these examples, and like embodiments, the input image is digitally mapped to an adjusted image plane (e.g. virtual image plane or retinal plane) designated to provide the user with a designated image perception adjustment that at least partially addresses designated visual aberrations. Naturally, while visual aberrations may be addressed using these approaches, other visual effects may also be implemented using similar techniques.

Figure 5:
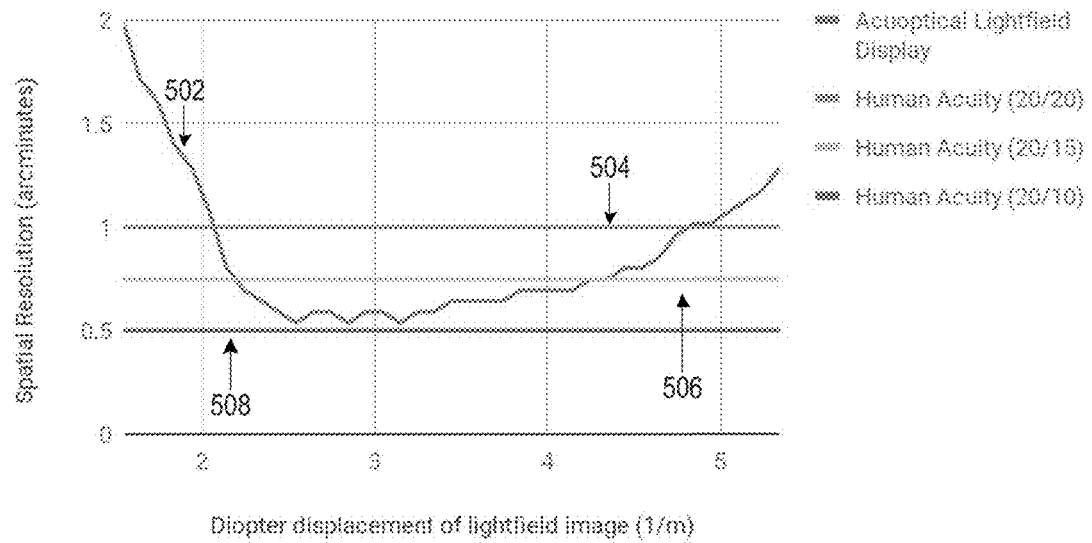
FIG. 5 is a plot of the angular resolution of an exemplary light field display as a function of the dioptric power generated, in accordance with one embodiment.

As an example of the effectiveness of the light field display in generating a diopter displacement (e.g. simulate the effect of looking through an optical component (i.e. a lens) of a given diopter strength or power) is shown in FIG. 5, where a plot is shown of the angular resolution (in arcminutes) of an exemplary light field display comprising a 1500 ppi digital pixel display, as a function of the dioptric power of the light field image (in diopters). From this plot, it is clear that, in this particular example, the light field display is able to generate displacements (line 502) in diopters that have higher resolution corresponding to 20/20 vision (line 504) or better (e.g. 20/15—line 506) and close to (20/10—line 508)), here within a dioptric power range of 2 to 2.5 diopters.

Thus, in the context of a refractor 102, light field display 104 (in conjunction with the light field rendering or ray-tracing methods described below) may, according to different embodiments, be used to replace, at least in part, traditional optical components.

In some embodiments, the light field display can display a virtual image at optical infinity, meaning that any level of accommodation-based presbyopia (e.g. first order) can be corrected for. In some further embodiments, the light field display can both push the image back or forward, thus allowing for selective image corrections for both hyperopia (far-sightedness) and myopia (nearsightedness). In yet further embodiments as described below, variable displacements and/or accommodations may be applied as a function of non-uniform visual aberrations, or again to provide perceptive previewing or simulation of non-uniform or otherwise variable corrective powers/measures across a particular input or field of view.

However, the light field rendering system introduced above and the ray-tracing methods described below may also be used with other devices which may similarly comprise a light field display. For example, this may include a smartphone, tablets, e-readers, watches, televisions, GPS devices, laptops, desktop computer monitors, televisions, smart televisions, handheld video game consoles and controllers, vehicular dashboard and/or entertainment displays, and the like, without limitation.

Accordingly, any of the light field processing or ray-tracing methods described below, any modification thereto also discussed below, and related light field display solutions, can be equally applied to image perception adjustment solutions for visual media consumption, as they can for subjective vision testing solutions, or other technologically related fields of endeavour. As alluded to above, the light field display and rendering/ray-tracing methods discussed above may all be used to implement, according to various embodiments, a subjective vision testing device or system such as a phoropter or refractor. Indeed, a light field display may replace, at least in part, the various refractive optical components usually present in such a device. Thus, the vision correction light field ray tracing methods discussed below may equally be applied to render optotypes at different dioptric power or refractive correction by generating vision correction for hyperopia (far-sightedness) and myopia (nearsightedness), as was described above in the general case of a vision correction display. Light field systems and methods described herein, according to some embodiments, may be applied to create the same capabilities as a traditional instrument and to open a spectrum of new features, all while improving upon many other operating aspects of the device. For example, the digital nature of the light field display enables continuous changes in dioptric power compared to the discrete change caused by switching or changing a lens or similar; displaying two or more different dioptric corrections seamlessly at the same time; and, in some embodiments, the possibility of measuring higher-order aberrations and/or to simulate them for different purposes such as, deciding for free-form lenses, cataract surgery operation protocols, IOL choice, etc.

Going back to FIG. 1A, as producing a light field with angular resolution sufficient for accommodation correction over the full viewing 'zone' of a display would generally require an astronomically high pixel density, instead, a correct light field can be produced, in some embodiments, only at or around the location of the user's pupil(s). To do so, where a location or position of the user's eye is not otherwise rigidly constrained (e.g. within the context of a subject eye testing device or the like) the light field display can be paired with pupil tracking technology, as will be discussed below, to track a location of the user's eyes/pupils relative to the display. The display can then compensate for the user's eye location and produce the correct virtual image, for example, in real-time. Thus, in some embodiments, light field refractor 102 may include, integrated therein or interfacing therewith, a pupil/eye tracking system 110 to improve or enhance corrective image rendering by tracking a location of the user's eye(s)/pupil(s) (e.g. both or one, e.g. dominant, eye(s)) and adjusting light field corrections accordingly one or more eye/pupil tracking light sources, such as one or more infrared (IR) or near-IR (NIR) light source(s) to accommodate operation in limited ambient light conditions, leverage retinal retro-reflections, invoke corneal reflection, and/or other such considerations. For instance, different IR/NIR pupil tracking techniques may employ one or more (e.g. arrayed) directed or broad illumination light sources to stimulate retinal retro-reflection and/or corneal reflection in identifying a tracking a pupil location. Other techniques may employ ambient or IR/NIR light-based machine vision and facial recognition techniques to otherwise locate and track the user's eye(s)/pupil(s). To do so, one or more corresponding (e.g. visible, IR/NIR) cameras may be deployed to capture eye/pupil tracking signals that can be processed, using various image/sensor data processing techniques, to map a 3D location of the user's eye(s)/pupil(s). As mentioned above, in some embodiments, such eye/pupil tracking hardware/software may be integral to device 102, for instance, operating in concert with integrated components such as one or more front facing camera(s), onboard IR/NIR light source(s) (not shown) and the like. In other user environments, such as in a vehicular environment, eye/pupil tracking hardware may be further distributed within the environment, such as dash, console, ceiling, windshield, mirror or similarly-mounted camera(s), light sources, etc.

Figure 4A:
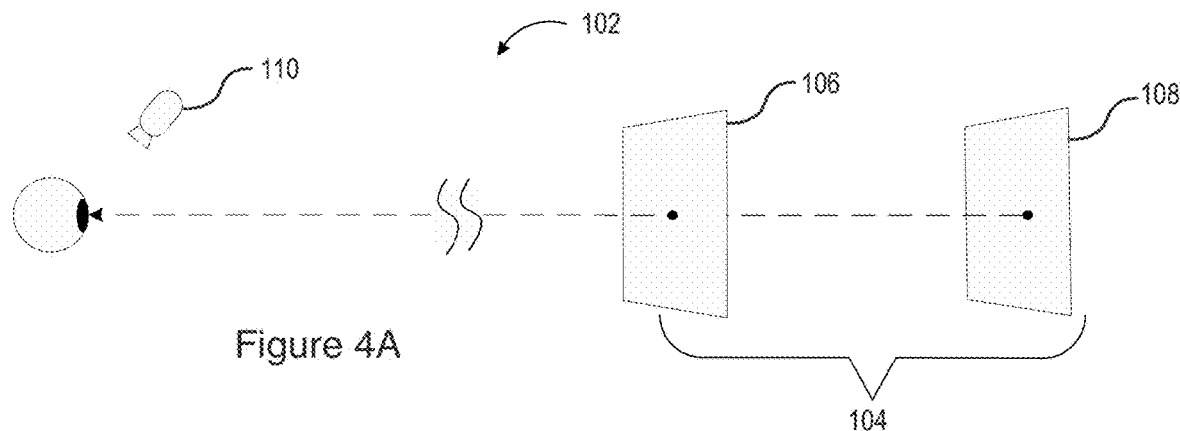
FIGS. 4A to 4C are schematic diagrams of exemplary light field vision testing or previewing systems (e.g. refractors/phoropters), in accordance with different embodiments.
Figure 4B:
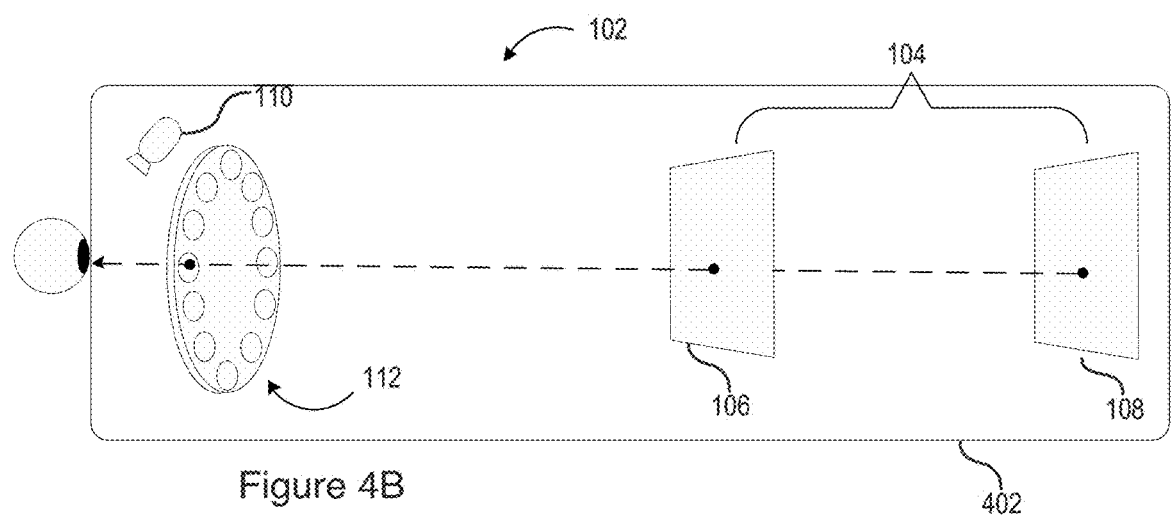
Figure 4C:
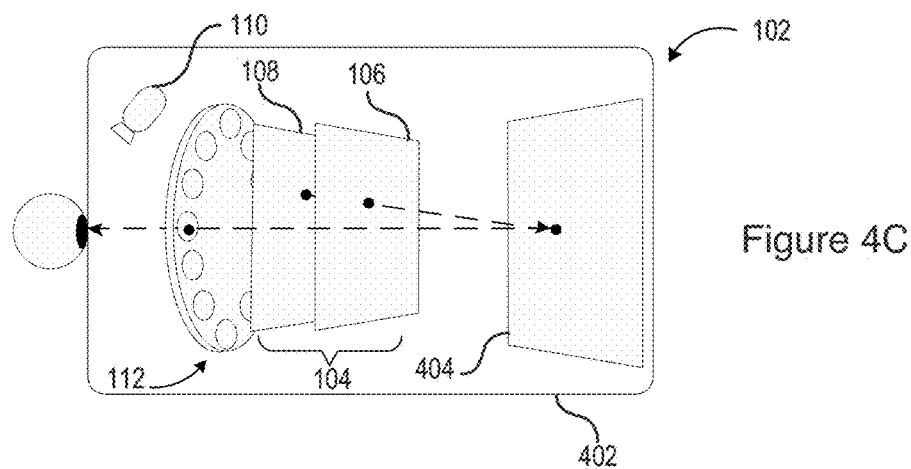

In one embodiment and as illustrated in FIG. 4A, light field refractor 102 may be configured with light field display 104 located relatively far away (e.g. one or more meters) from the user's eye currently being diagnosed. Note that the pointed line in FIGS. 4A to 4C is used to schematically illustrate the direction of the light rays emitted by light field display 104. Also illustrated is eye-tracker 110, which may be provided as a physically separate element, for example, installed in at a given location in a room or similar. In some embodiments, the noted eye/pupil tracker 110 may include the projection of IR markers/patterns to help align the patient's eye with the light field display. In some embodiments, a tolerance window (e.g. "eye box") may be considered to limit the need to refresh the ray-tracing iteration. An exemplary value of the size of the eye box, in some embodiments, is around 6 mm, though smaller (e.g. 4 mm) or larger eye boxes may alternatively be set to impact image quality, stability or like operational parameters.

Going back to FIG. 1A, light field refractor 102 may also comprise, according to different embodiments and as will be further discussed below, one or more refractive optical components 112, a processing unit 114, a data storage unit or internal memory 116, one or more cameras 118, a power source 120, a network interface 122 for communicating via network to a remote database or server 124.

In some embodiments, power source 120 may comprise, for example, a rechargeable Li-ion battery or similar. In some embodiments, it may comprise an additional external power source, such as, for example, a USB-C external power supply. It may also comprise a visual indicator (screen or display) for communicating the device's power status, for example whether the device is on/off or recharging.

In some embodiments, internal memory 116 may be any form of electronic storage, including a disk drive, optical drive, read-only memory, random-access memory, or flash memory, to name a few examples. In some embodiments, a library of chart patterns (Snellen charts, prescribed optotypes, forms, patterns, or other) may be located in internal memory 116 and/or retrievable from remote server 124 via network interface 122.

Figure 6A:
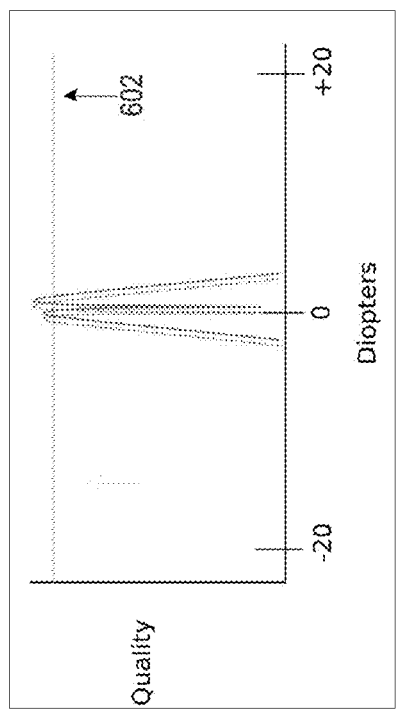
FIGS. 6A to 6D are schematic plots of the image quality generated by a light field refractor/phoropter as a function of the dioptric power generated by using in combination with the light field display (A) no refractive component, (B) one refractive component, (C) and (D) a multiplicity of refractive components.
Figure 6B:
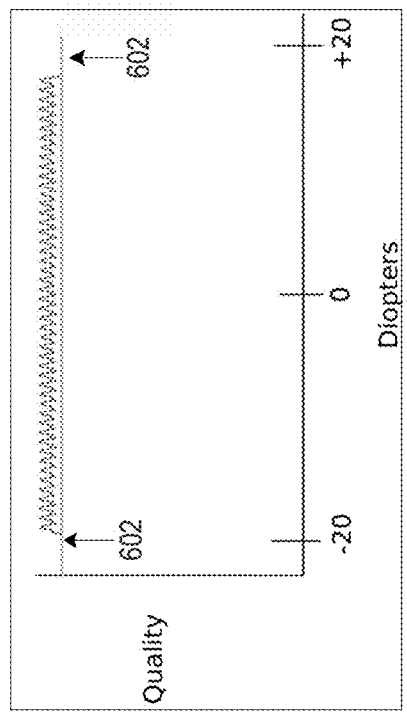

In some embodiments, one or more optical components 112 may be used in combination with the light field display 104, for example to shorten the size of refractor 102 and still offer an acceptable range in dioptric power. The general principle is schematically illustrated in the plots of FIGS. 6A to 6D. In these schematic plots, the image quality (e.g. inverse of the angular resolution, higher is better) at which optotypes are small enough to be useful for vision testing in this plot is above horizontal line 602 which represents typical 20/20 vision. FIG. 6A shows the plot for the light field display only, where we see the characteristic two peaks corresponding to the smallest resolvable point, one of which was plotted in FIG. 5 (here inverted and shown as a peak instead of a basin), and where each region above the line may cover a few diopters of dioptric power, according to some embodiments. While the dioptric range may, in some embodiments, be more limited than needed when relying only on the light field display, it is possible to shift this interval by adding one or more refractive optical components. This is shown in FIG. 6B where the regions above the line 602 is shifted to the left (negative diopters) by adding a single lens in the optical path.

Figure 6C:
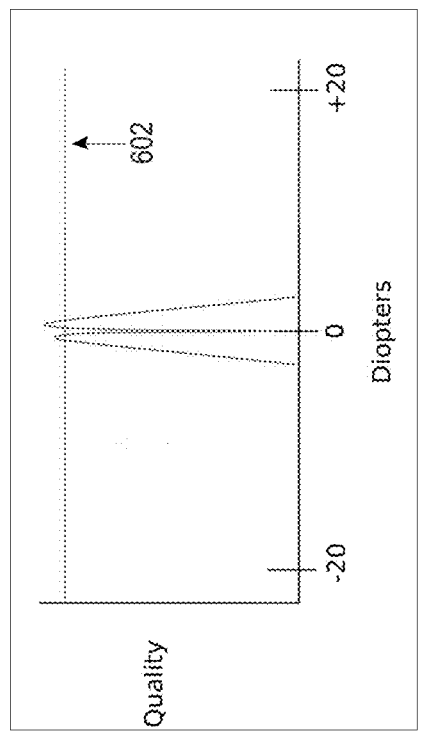
Figure 6D:
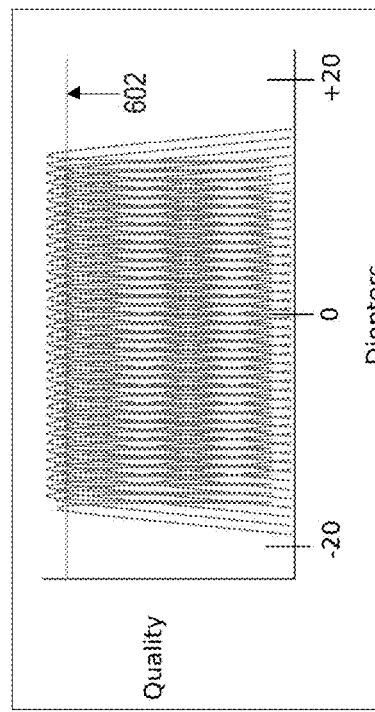

Thus, by using a multiplicity of refractive optical components 112 or by alternating sequentially between different refractive components 112 of increasing or decreasing dioptric power, it is possible to shift the center of the light field diopter range to any required value, as shown in FIG. 6C, and thus the image quality may be kept above line 602 for any required dioptric power as shown in FIG. 6D. In some embodiments, a range of 30 diopters from +10 to −20 may be covered for example. In the case of one or more reels of lenses, the lens may be switched for a given larger dioptric power increment, and the light field display would be used to provide a finer continuous change to accurately pin-point the required total dioptric power required to compensate for the patient's reduced visual acuity. This would still result in light field refractor 102 having a reduced number of refractive optical components compared to the number of components needed in a traditional refractor, while drastically enhancing the overall fine-tuning ability of the device.

One example, according to one embodiment, of such a light field refractor 102 is schematically illustrated in FIG. 4B, wherein the light field display 104 (herein shown comprising LFSL 106 and digital pixel display 108) is combined with a multiplicity of refractive components 112 (herein illustrated as a reel of lenses as an example only). By changing the refractive component used in combination with light field display 104, a larger dioptric range may be covered. This may also provide means to reduce the dimension of device 102 as mentioned above, making it more portable, so that all its internal components may be encompassed into a shell, housing or casing 402. In some embodiments, light field refractor 102 may thus comprise a durable ABS housing that may be shock and harsh-environment resistant. In some embodiments, light field refractor 102 may also comprise a telescopic feel for fixed or portable usage; optional mounting brackets, and/or a carrying case (not shown). In some embodiments, all components may be internally protected and sealed from the elements.

In some embodiments, casing 402 may further comprise a head-rest or similar (not shown) to keep the user's head still and substantially in the same location, thus, in such examples, foregoing the general utility of a pupil tracker or similar techniques by substantially fixing a pupil location relative to this headrest.

In some embodiments, it may also be possible to further reduce the size of device 102 by adding, for example, a mirror or any device which may increase the optical path. This is illustrated in FIG. 4C where the length of the device was reduced by adding a mirror 404. This is shown schematically by the pointed arrow which illustrates the light being emitted from pixel display 108 travelling through LFSL 106 before being reflected back by mirror through refractive components 112 and ultimately hitting the eye.

The skilled technician will understand that different examples of refractive components 112 may be include, without limitation, one or more lenses, sometimes arranged in order of increasing dioptric power in one or more reels of lenses similar to what is typically found in traditional refractors/phoropters; an electrically controlled fluid lens; active Fresnel lens; and/or Spatial Light Modulators (SLM). In some embodiments, additional motors and/or actuators (not shown) may be used to operate refractive components 112. The motors/actuators may be communicatively linked to processing unit 114 and power source 120, and operate seamlessly with light field display 102 to provide the required dioptric power.

Figure 7A:
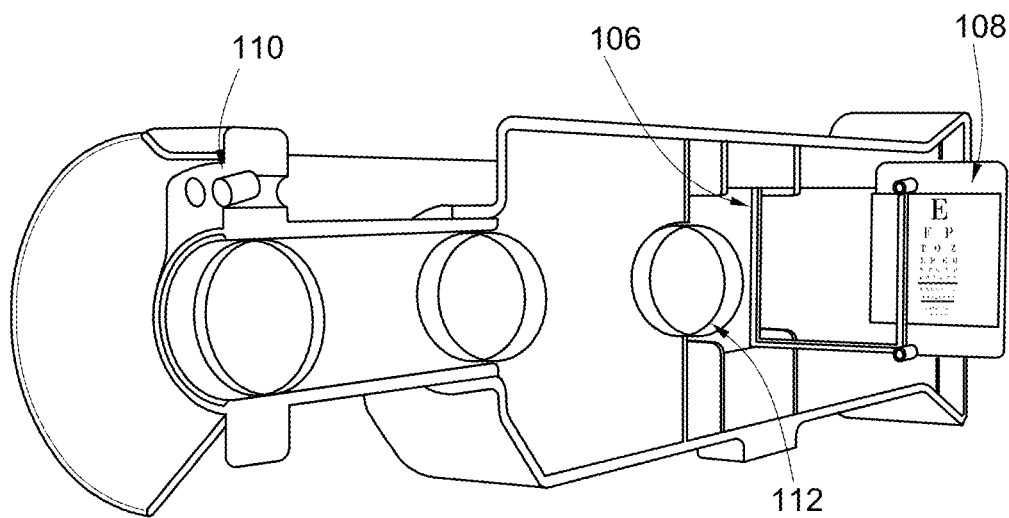
FIGS. 7A, 7B and 7C are perspective views of exemplary light field refractors/phoropters, showing a casing thereof in cross-section (A and B) and a unit combining side-by-side two of the units (C) shown in 7A and 7B, in accordance with one embodiment.
Figure 7B:
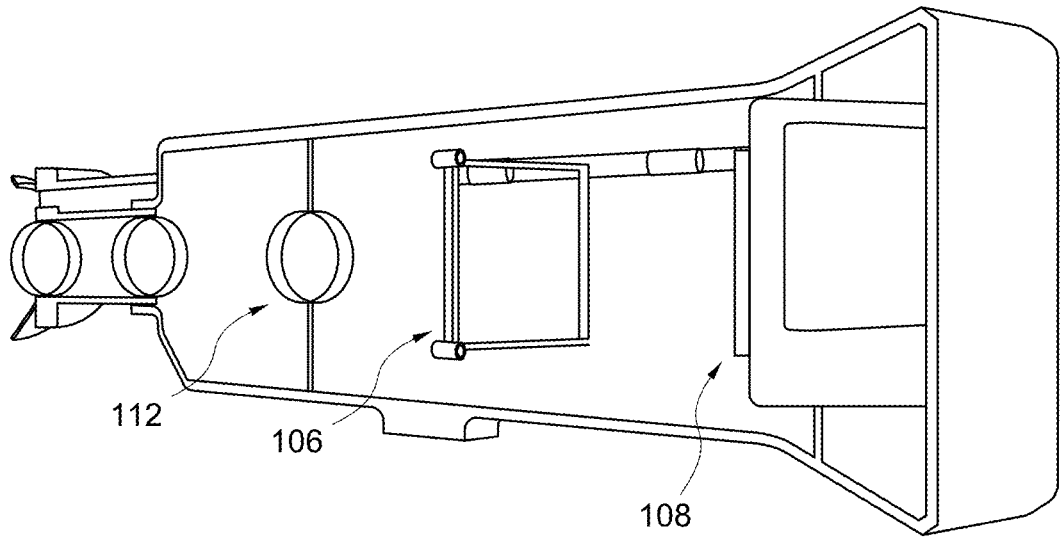

For example, FIGS. 7A and 7B show a perspective view of an exemplary light field phoropter 102 similar to the one schematically shown in FIG. 3B, but wherein the refractive component 112 is an electrically tunable liquid lens. Thus, in this particular embodiment, no mechanical or moving component are used, which may result in the device being more robust. In some embodiments, the electrically tunable lens may have a range of ±13 diopters.

In one illustrative embodiment, a 1000 dpi display is used with a MLA having a 65 mm focal distance and 1000 μm pitch with the user's eye located at a distance of about 26 cm. A similar embodiment uses the same MLA and user distance with a 3000 dpi display.

Other displays having resolutions including 750 dpi, 1000 dpi, 1500 dpi and 3000 dpi were also tested or used, as were MLAs with a focal distance and pitch of 65 mm and 1000 μm, 43 mm and 525 μm, 65 mm and 590 μm, 60 mm and 425 μm, 30 mm and 220 μm, and 60 mm and 425 μm, respectively, and user distances of 26 cm, 45 cm or 65 cm.

Going back to FIG. 1A, in some embodiments, eyetracker 110 may further comprise a digital camera, in which case it may be used to further acquire images of the user's eye to provide further diagnostics, such as pupillary reflexes and responses during testing for example. In other embodiments, one or more additional cameras 118 may be used to acquire these images instead. In some embodiments, light field refractor 102 may comprise built-in stereoscopic tracking cameras.

In some embodiments, feedback and/or control of the vision test being administered by system 100 may be given via a control interface 126. In some embodiments, the control interface 126 may comprise a dedicated handheld controller-like device 128. This controller 128 may be connected via a cable or wirelessly, and may be used by the patient directly and/or by an operator like an eye professional. In some embodiments, both the patient and operator may have their own dedicated controller 128. In some embodiments, the controller may comprise digital buttons, analog thumbstick, dials, touch screens, and/or triggers.

In some embodiments, control interface 126 may comprise a digital screen or touch screen, either on refractor 102 itself or part of an external module (not shown). In other embodiments, control interface 126 may let on or more external remote devices (i.e. computer, laptop, tablet, smartphone, remote, etc.) control light field refractor 102 via network interface 122. For example, remote digital device 130 may be connected to light field refractor 102 via a cable (e.g. USB cable, etc.) or wirelessly (e.g. via Wi-Fi, Bluetooth or similar) and interface with light field refractor 102 via a dedicated application, software or website (not shown). Such a dedicated application may comprise a graphical user interface (GUI), and may also be communicatively linked to remote database 124.

In some embodiments, the user or patient may give feedback verbally and the operator may control the vision test as a function of that verbal feedback. In some embodiments, refractor 102 may comprise a microphone (not shown) to record the patient's verbal communications, either to communicate them to a remote operator via network interface 122 or to directly interact with the device (e.g. via speech recognition or similar).

Going back to FIG. 1A, processing unit 114 may be communicatively connected to data storage 116, eye tracker 110, light field display 104 and refractive components 112. Processing unit 114 may be responsible for rendering one or more images or optotypes via light field display 104 and, in some embodiments, jointly control refractive components 112 to achieve a required total change in dioptric power. It may also be operable to send and receive data to internal memory 116 or to/from remote database 124 via network interface 122.

In some embodiments, diagnostic data may be automatically transmitted/communicated to remote database 124 or remote digital device 130 via network interface 122 through the use of a wired or wireless network connection. The skilled artisan will understand that different means of connecting electronic devices may be considered herein, such as, but not limited to, Wi-Fi, Bluetooth, NFC, Cellular, 2G, 3G, 4G, 5G or similar. In some embodiments, the connection may be made via a connector cable (e.g. USB including microUSB, USB-C, Lightning connector, etc.). In some embodiments, remote digital device 130 may be located in a different room, building or city.

Figure 7C:
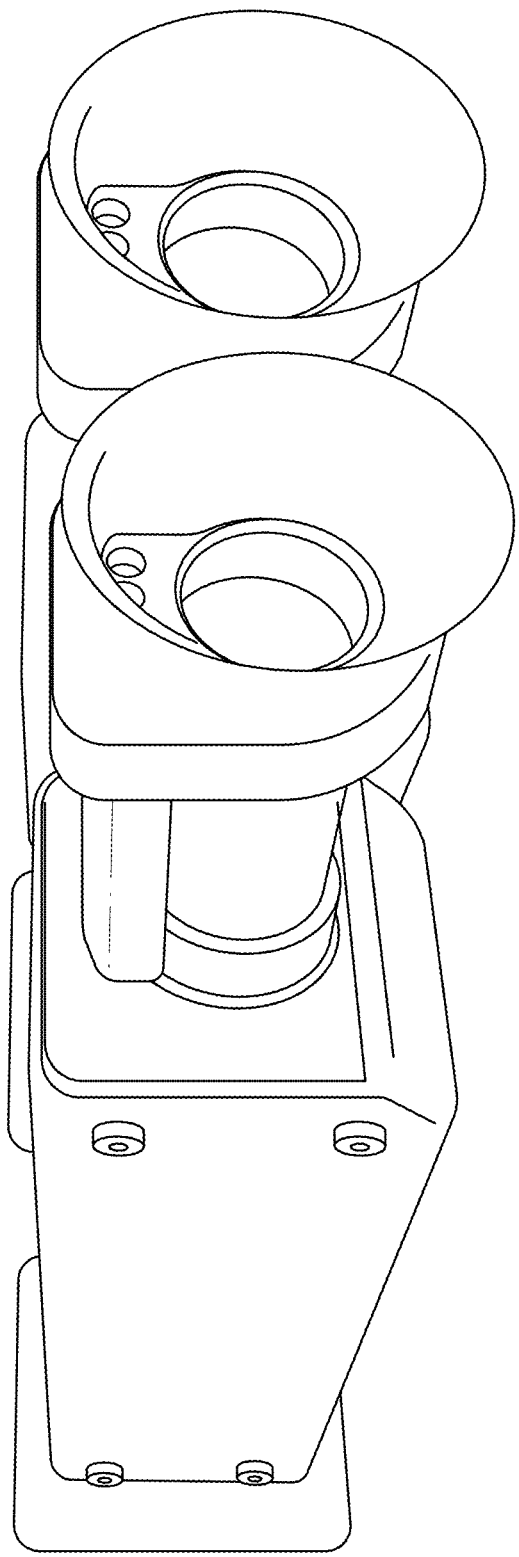

In some embodiments, two light field refractors 102 may be combined side-by-side to independently measure the visual acuity of both left and right eye at the same time. An example is shown in FIG. 7C, where two units corresponding to the embodiment of FIG. 7A or 7B (used as an example only) are placed side-by-side or fused into a single device.

In some embodiments, a dedicated application, software or website may provide integration with third party patient data software. In some embodiments, software required to operate and installed on refractor 102 may be updated on-the-fly via a network connection and/or be integrated with the patient's smartphone app for updates and reminders.

In some embodiments, the dedicated application, software or website may further provide a remote, real-time collaboration platform between an eye professional and user/patient, and/or between different eye professionals. This may include interaction between different participants via video chat, audio chat, text messages, etc.

In some embodiments, light field refractor 102 may be self-operated or operated by an optometrist, ophthalmologist or other certified eye-care professional. For example, in some embodiments, a user/patient may use refractor 102 in the comfort of his/her own home, in a store or a remote location.

In some embodiments, refractor 102 (or each right/left portion of a binocular refractor) may further include additional optical components or assemblies, as introduced above, to non-refractively guide or realign a predominant view zone toward a device output and corresponding user pupil location/configuration. For example, in some embodiments and as illustrated schematically in FIG. 48, refractor 4802 may comprise, for each eye, a corresponding view zone redirecting mirror assembly configured to act as a periscope-like device for redirecting the light field emitted by the light field display along a redirected optical path, for example, to accommodate a physical mismatch between device performance and/or form factor requirements and average physical characteristics of a user's face (e.g. eye position, IPD, etc.). For example, in some embodiments, two monocular devices joined together such as the one illustrated in FIG. 7C may have components that are such that the output from each light field display (or each light field display portion of a common display) is further apart than that imposed or preferred to accommodate a user's (average or input) IPD. This may be a result, for example, of display requirement to achieve a desired output resolution or brightness, for example, whereby displays of a certain minimum width are required that, when disposed side-by-side, result in the non-ideal formation of overly spaced-apart predominant binocular view zones. Accordingly, rather than to accept formation of sub-optimal view zone characteristics or constrain or limit use of or access to available pixels, non-refractive view zone redirection optics may be aptly employed to address such geometrical/dimensional mismatches.

Figure 48:
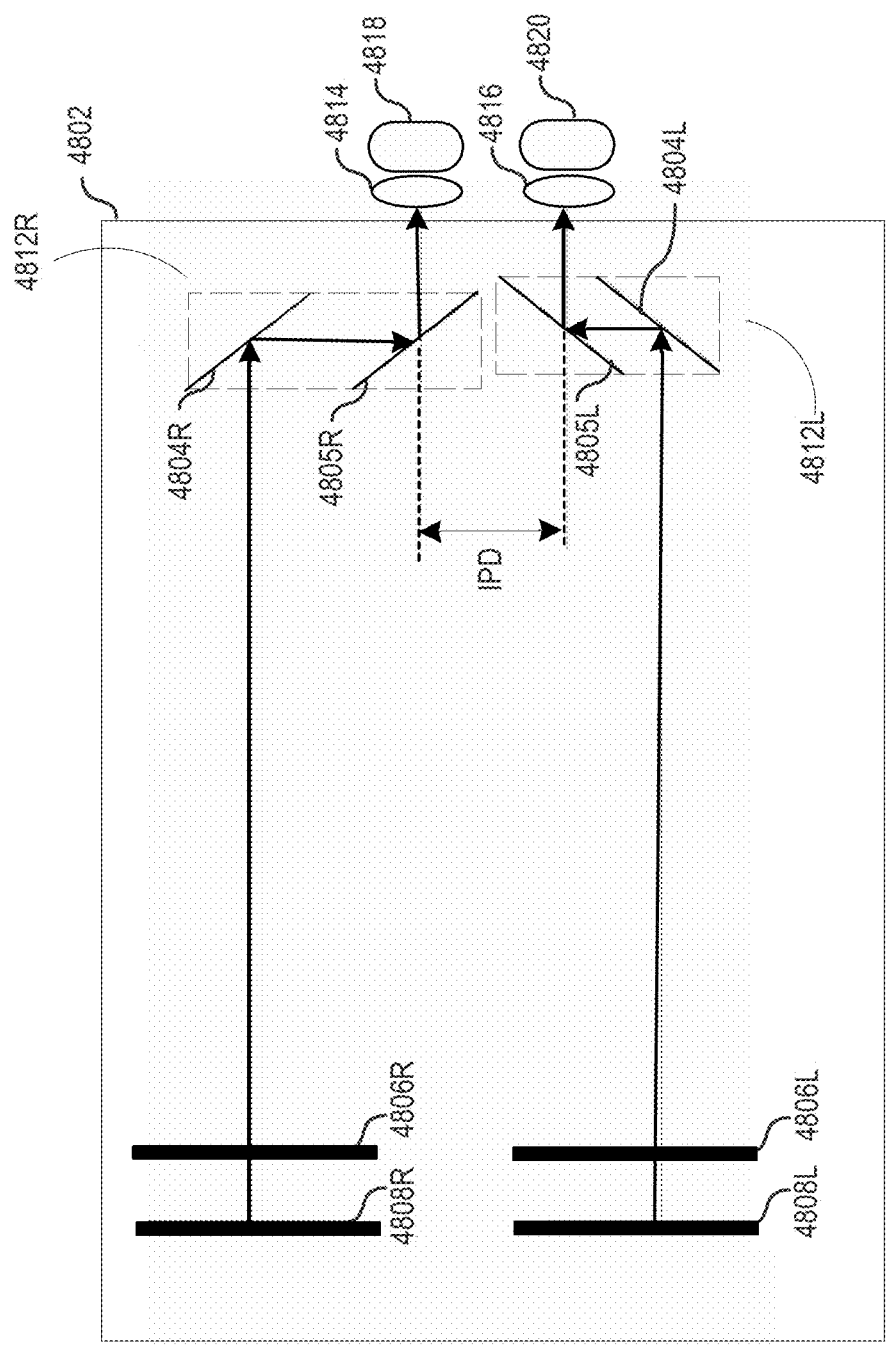
FIG. 48 is a schematic diagram of an exemplary binocular refractor device comprising respective light field optics, mirror assemblies, and refractive optical systems, in accordance with one embodiment.

Indeed, in some embodiments, one or more mirror assemblies are used to redirect the light field image from each display (portion) so that the spacing between the light field outputs at the eyes is substantially equal to the IPD. In FIG. 48, which shows schematically a top-down view of a binocular refractor 4802, two assemblies 4812R and 2712L are shown, each comprising mirror pairs 4804R and 4805R, and 4804L and 4805L, respectively, to move the respective right and left view zones generated by the right and left LFSLs 4806R/L and pixel displays 4808R/L, respectively, to the appropriate location in line with the user's eyes.

In this particular embodiment, a refractive optical assembly is further included to extend the dynamic compensation range (further described below) otherwise provided by the light field components of the refractor 4802. For instance, respective right (4814) and left (4816) spherical tunable lenses (or respective stacks thereof), are provided to provide a complementary dynamic spherical compensation range, whereas respective right (4818) and left (4820) cylindrical optical elements (e.g. respective dynamically rotationally offset cylindrical lens pairs) are provided to provide a complementary dynamic cylindrical compensation range. Such compensation range-extending components will be described in further detail below. Similar or alternative device configurations, and optical components therefor, are described in Applicant's co-pending International Application No. PCT/US2021/070936 filed Jul. 22, 2021, the entire contents of which are hereby incorporated herein by reference.

Figure 8:
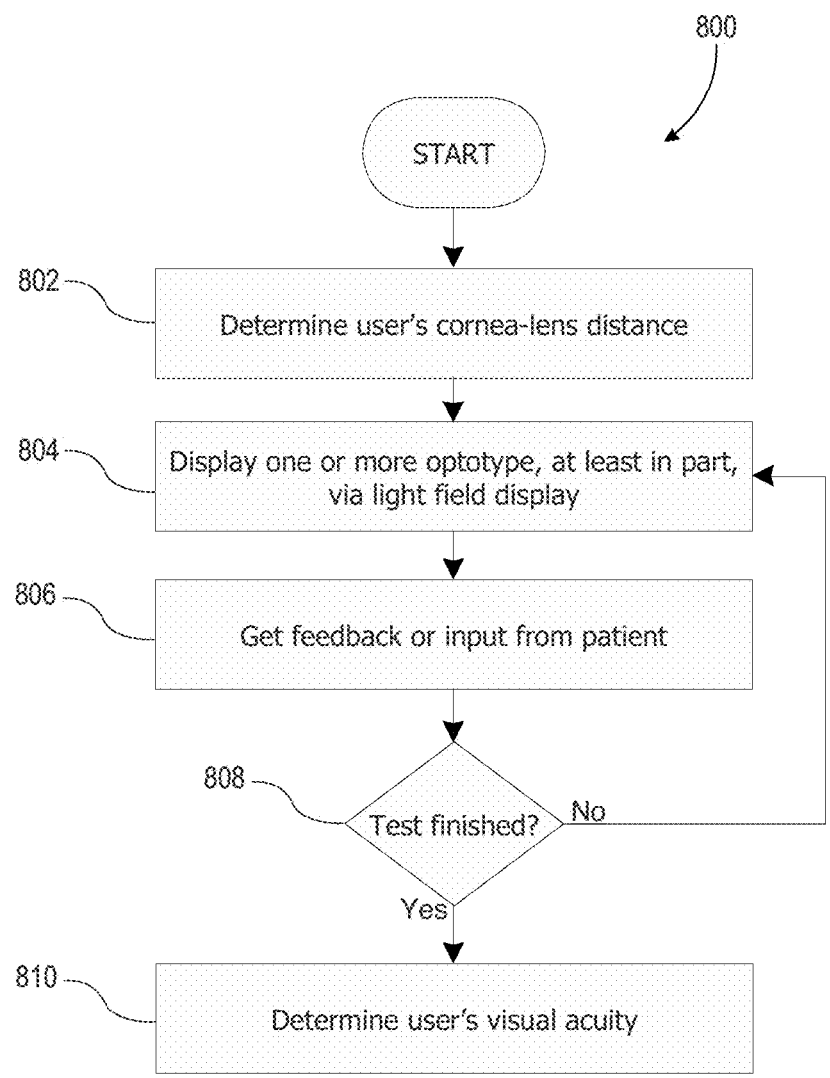
FIG. 8 is a process flow diagram of an exemplary dynamic subjective vision testing method, in accordance with one embodiment.

With reference to FIG. 8 and in accordance with one exemplary embodiment, a dynamic subjective vision testing method using vision testing system 100, generally referred to using the numeral 800, will now be described. As mentioned above, the use of a light field display enables refractor 102 to provide more dynamic and/or more modular vision tests than what is generally possible with traditional refractors/phoropters. Generally, method 800 seeks to diagnose a patient's reduced visual acuity and produce therefrom, in some embodiments, an eye prescription or similar.

In some embodiments, eye prescription information may include, for each eye, one or more of: distant spherical, cylindrical and/or axis values, and/or a near (spherical) addition value.

In some embodiments, the eye prescription information may also include the date of the eye exam and the name of the eye professional that performed the eye exam. In some embodiments, the eye prescription information may also comprise a set of vision correction parameter(s), as will be further discussed below, for operating any vision correction light field displays using the systems and methods described below. In some embodiments, the eye prescription may be tied to a patient profile or similar, which may contain additional patient information such as a name, address or similar. The patient profile may also contain additional medical information about the user. All information or data (i.e. set of vision correction parameter(s), user profile data, etc.) may be kept on external database 124. Similarly, in some embodiments, the user's current vision correction parameter(s) may be actively stored and accessed from external database 124 operated within the context of a server-based vision correction subscription system or the like, and/or unlocked for local access via the client application post user authentication with the server-based system.

Refractor 102 being, in some embodiments, portable, a large range of environments may be chosen to deliver the vision test (home, eye practitioner's office, etc.). At the start, the patient's eye may be placed at the required location. This may be done by placing his/her head on a headrest or by placing the objective (i.e. eyepiece) on the eye to be diagnosed. As mentioned above, the vision test may be self-administered or partially self-administered by the patient. For example, the operator (e.g. eye professional or other) may have control over the type of test being delivered, and/or be the person who generates or helps generate therefrom an eye prescription, while the patient may enter inputs dynamically during the test (e.g. by choosing or selecting an optotype, etc.).

As will be discussed below, light field rendering methods described herein generally requires an accurate location of the patient's pupil center. Thus, at step 802, such a location is acquired. In some embodiments, such a pupil location may be acquired via eye tracker 110, either once, at intervals, or continuously. In other embodiments, the location may be derived from the device or system's dimension. For example, in some embodiments, the use a head-rest and/or an eye-piece or similar provides an indirect means of deriving the pupil location. In some embodiments, refractor 102 may be self-calibrating and not require any additional external configuration or manipulation from the patient or the practitioner before being operable to start a vision test.

At step 804, one or more optotypes is/are displayed to the patient, at one or more dioptric power (e.g. in sequence, side-by-side, or in a grid pattern/layout). The use of light field display 104 offers multiple possibilities regarding how the images/optotypes are presented, and at which dioptric power each may be rendered. The optotypes may be presented sequentially at different dioptric power, via one or more dioptric power increments. In some embodiments, the patient and/or operator may control the speed and size of the dioptric power increments.

Figure 9:
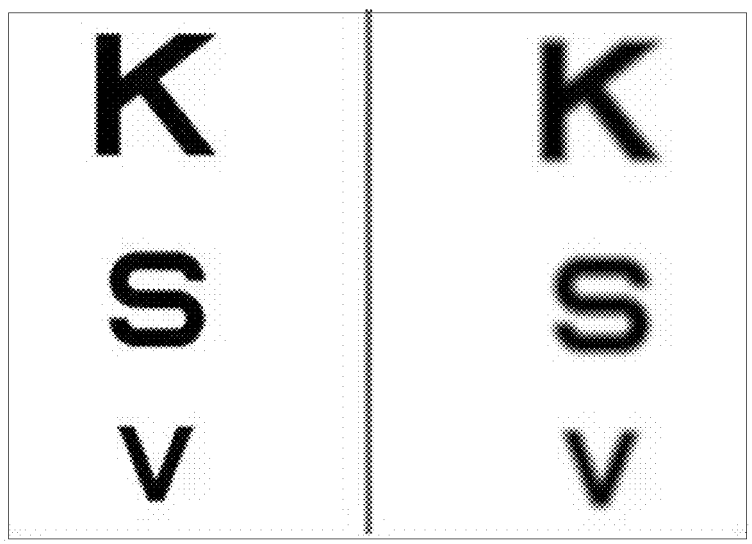
FIG. 9 is a schematic diagram of an exemplary light field image showing two columns of optotypes at different dioptric power for the method of FIG. 8, in accordance with one embodiment.

In some embodiments, optotypes may also be presented, at least in part, simultaneously on the same image but rendered at a different dioptric power. For example, FIG. 9 shows an example of how different optotypes may be displayed to the patient but rendered with different dioptric powers simultaneously. These may be arranged in columns or in a table or similar. In FIG. 9, we see two columns of three optotypes (K, S, V), varying in size, as they are perceived by a patient, each column being rendered at different degrees of refractive correction (e.g. dioptric power). In this specific example, the optotypes on the right are being perceived as blurrier than the optotypes on the left.

Thus, at step 806, the patient would communicate/verbalize this information to the operator or input/select via, for example, control interface 126 the left column as the one being clearer. Thus, in some embodiments, method 800 may be configured to implement dynamic testing functions that dynamically adjust one or more displayed optotype's dioptric power in real-time in response to a designated input, herein shown by the arrow going back from step 808 to step 804 in the case where at step 808, the user or patient communicates that the perceived optotypes are still blurry or similar. In the case of sequentially presented optotypes, the patient may indicate when the optotypes shown are clearer. In some embodiments, the patient may control the sequence of optotypes shown (going back and forth as needed in dioptric power), and the speed and increment at which these are presented, until he/she identifies the clearest optotype. In some embodiments, the patient may indicate which optotype or which group of optotypes is the clearest by moving an indicator icon or similar within the displayed image.

In some embodiments, the optotypes may be presented via a video feed or similar.

In some embodiments, when using a reel of lenses or similar (for refractive components 112), discontinuous changes in dioptric power may be unavoidable. For example, the reel of lenses may be used to provide a larger increment in dioptric power, as discussed above. Thus, step 804 may in this case comprise first displaying larger increments of dioptric power by changing lens as needed, and when the clearest or less blurry optotypes are identified, fine-tuning with continuous or smaller increments in dioptric power using the light field display. In the case of optotypes presented simultaneously, the refractive components 112 may act on all optotypes at the same time, and the change in dioptric power between them may be controlled only by the light display 104. In some embodiments, for example when using an electrically tunable fluid lens or similar, the change in dioptric power may be continuous.

In some embodiments, eye images may be recorded during steps 802 to 806 and analyzed to provide further diagnostics. For example, eye images may be compared to a bank or database of proprietary eye exam images and analyzed, for example via an artificial intelligence (AI) or Machine-learning (ML) system or similar. This analysis may be done by refractor 102 locally or via a remote server or database 124.

Once the correct dioptric power needed to correct for the patient's reduced visual acuity is defined at step 810, an eye prescription or vision correction parameter(s) may be derived from the total dioptric power used to display the best perceived optotypes.

In some embodiments, the patient, an optometrist or other eye-care professional may be able to transfer the patient's eye prescription directly and securely to his/her user profile store on said server or database 124. This may be done via a secure website, for example, so that the new prescription information is automatically uploaded to the secure user profile on remote database 124. In some embodiments, the eye prescription may be sent remotely to a lens specialist or similar to have prescription glasses prepared.

In some embodiments, vision testing system 100 may also or alternatively be used to simulate compensation for other or higher-order aberrations. Indeed, the light field rendering methods described above may be used to compensation for higher order aberrations (HOA), and thus be used to validate externally measured or tested HOA via method 3600, in that a measured, estimated or predicted HOA can be dynamically compensated for using the system described herein and thus subjectively visually validated by the viewer in confirming whether the applied HOA correction satisfactorily addresses otherwise experienced vision deficiencies.

With reference to FIGS. 10A to 17D, and in accordance with different embodiments, an exemplary computationally implemented ray-tracing method for rendering an adjusted image via an array of light field shaping elements, in this example provided by a light field shaping layer (LFSL) disposed relative to a set of underlying display pixels, that accommodates or compensates for the user's reduced visual acuity will now be described. In this first example, for illustrative purposes, adjustment of a single image (i.e. the image as whole) is being implemented without consideration for distinct image portions and taking only into account spherical dioptric power changes. Further examples below will specifically address modification of the following example for adaptively adjusting distinct image portions and/or adjustments considering other aberrations such as HOA, and/or astigmatism.

Figure 10A:
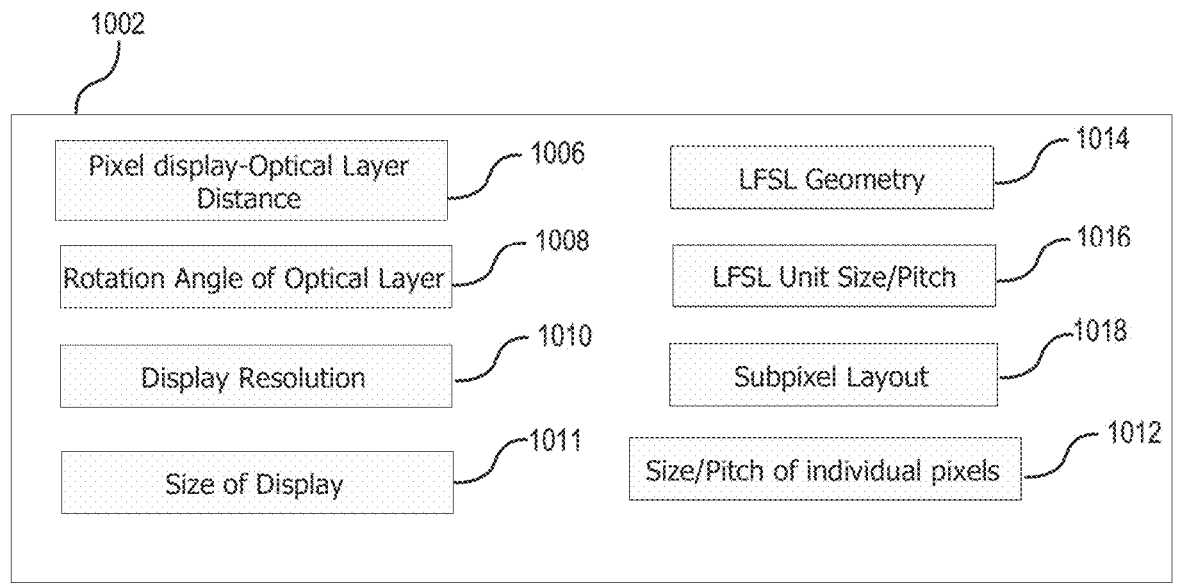
FIGS. 10A and 10B are process flow diagrams of exemplary input constant parameters and variables, respectively, for the ray-tracing rendering process of FIG. 11, in accordance with one embodiment.

In this exemplary embodiment and as shown in FIG. 10A, a set of constant parameters 1002 used for the light field rendering process may be pre-determined. These may include, for example, any data or parameters that are not expected to significantly change during a user's viewing session, between different viewing sessions or even between users, for instance. These may generally be based on the physical and functional characteristics of light field display 104 for which the method is to be implemented, as will be explained below. Similarly, as shown in FIG. 10B, every iteration of the rendering algorithm (i.e. when rendering a full light field image frame) may also use a set of input variables 1004 which are expected to change either at each rendering iteration (i.e. between frames) or at least between each user's viewing session.

As illustrated in FIG. 10A, the list of constant parameters 1002 may include, without limitations, the distance 1006 between pixel display 108 and the LFSL 106, the in-plane rotation angle 1008 between the frames of reference digital pixel display 108 and LFSL 106, the resolution 1010 and/or size 1011 of digital pixel display 108, the size 1012 of each individual pixel, the optical geometry 1014 of LFSL 106, the size or pitch of individual optical elements or units 1016 within LFSL 106 and optionally the subpixel layout 1018 of pixel display 108. Moreover, both the resolution 1010 and the size of each individual pixel 1012 of pixel display 108 may be used to pre-determine both the absolute size of the display in real units (i.e. in mm) and the three-dimensional position/location of each pixel within the display. In some embodiments where the subpixel layout 1018 is available, the position/location within pixel display 108 of each subpixel may also be pre-determined. These three-dimensional location/positions are usually calculated using a given frame of reference located somewhere within the plane of pixel display 108, for example a corner or the middle of the display, although other reference points may be chosen. Concerning the optical layer geometry 1014, different geometries may be considered, for example a hexagonal geometry. Finally, by combining the distance 1006, the rotation angle 1008, and the geometry 1014 with the optical element size 1016, it is possible to similarly pre-determine the three-dimensional location/position of each optical element of LFSL 106 with respect to the frame of reference of pixel display 108.

Figure 10B:
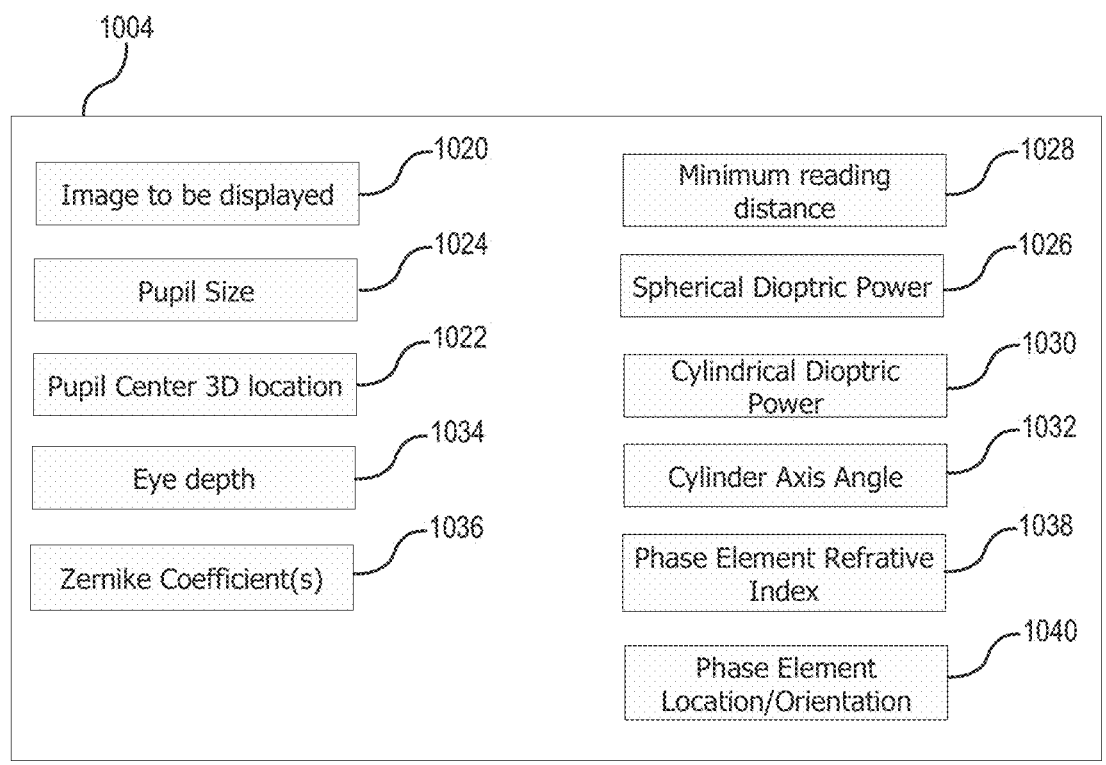

FIG. 10B meanwhile illustratively lists an exemplary set of input variables 1004 that may be used for the light field rendering methods described below, and may include any input data that may reasonably change during a user's single viewing session, for example between each image frame, or between different viewing sessions or even between different users (e.g. not related to the hardware specifications of light field display 104 or refractor 102). These may be automatically acquired by device 102 during normal operation or be inputted (for example by a user or person operating the device for the user) into the device as required. They may thus include without limitation: the image(s)/optotype(s) to be displayed 1020 (e.g. comprising pixel data such as on/off, colour, brightness, etc.), a three-dimensional pupil center location 1022 (e.g. in embodiments implementing active eye/pupil tracking methods) and/or a pupil size 1024.

The methods described below, according to different embodiments, also utilize vision correction parameters in the form of dioptric power so as to modulate the strength and nature of the compensation/correction generated by the light field image. These may include a spherical dioptric power 1026 (which may be derived indirectly, for example, from a minimum reading distance value 1028 as will be discussed below), but also, in some embodiments, one or more sets of a cylindrical power 1030 and a corresponding cylindrical axis angle 1032. In some embodiments, these input variables (spherical dioptric power 1026, cylindrical dioptric power 1026 and cylinder axis angle 1030) mirror the SPHERE, CYL and AXIS parameters used in a typical eye examination.

Moreover, in some embodiments, an eye depth value 1034 may also be used, either as an average value or customized for an individual user. In some embodiments, input image 1020, may be representative of one or more digital images to be displayed with digital pixel display 108. In addition, input image 1020 may generally be encoded in any data format used to store digital images known in the art.

Pupil center location 1022, in one embodiment, is the three-dimensional coordinates of at least one the user's pupils' center with respect to a given reference frame, for example a point on device 102 or digital pixel display 108 and may be derived from any eye/pupil tracking method known in the art via eye/pupil tracker 110. In some embodiments, the pupil center location 1022 may be determined prior to any new iteration of the rendering algorithm, or in other cases, at a lower framerate (and thus re-use the same location/position for two or more subsequent image frames). In some embodiments, only the pupil center location of a single user's eye may be determined, for example the user's dominant eye (i.e. the one that is primarily relied upon by the user). In some embodiments, this location/position, and particularly the associated pupil distance to the screen may otherwise or additionally be rather approximated or adjusted based on other contextual or environmental parameters, such as an average or preset user distance to the screen (e.g. typical reading distance for a given user or group of users; stored, set or adjustable driver distance in a vehicular environment; etc.).

In the illustrated embodiment, the minimum reading distance 1028 is defined as the minimal focus distance for reading that the user's eye(s) may be able to accommodate (i.e. able to view without discomfort). In some embodiments, different values of the minimum reading distance 1028 associated with different users may be entered, for example, as can other adaptive vision correction parameters be considered depending on the application at hand and vision correction being addressed. As mentioned above, in some embodiments, minimum reading distance 1028 may be derived from an eye prescription (e.g. glasses prescription or contact prescription) or similar. It may, for example, correspond to the near point distance corresponding to the uncorrected user's eye, which can be calculated from the prescribed corrective lens power assuming that the targeted near point was at 25 cm.

In some embodiments, as will be further described below, input variables 1004 may further comprise a set of Zernike coefficients 1036. These are usually used to define or characterize a set of HOAs to be corrected, as will be described below, in accordance with different embodiments. These may be chosen so as to describe one or more optical aberrations via a Zernike polynomial. In some embodiments, these may be used in addition to or in replacement of previously discussed variables such as spherical power 1026, cylindrical power 1030 or cylinder axis angle 1032. In other embodiments, at least some of the Zernike coefficients 1036 may be derived from spherical power 1026, cylindrical power 1030 or cylinder axis angle 1032. For example, in some embodiments, Zernike coefficients 1036 may be used to model HOA only, while spherical power may be simulated via the method 1100 described below. In some embodiments, in the exemplary case of astigmatism, the corresponding Zernike coefficients 1036 may be computed from spherical power 1026, cylindrical power 1030 or cylinder axis angle 1032, as will be shown below.

In addition, the methods for treating HOAs discussed below, in accordance with different embodiments, will make use of an optical or phase element to simulate the effects of HOAs. This element may have additional variables associated with it, for example at least one refractive index 1038 and a location/orientation 1040. More details regarding the use of this phase element (or a plurality of elements) will be given further below.

With added reference to FIGS. 11 to 16D, parameters 1002 and variables 1004 may be used in the light field ray-tracing method 1100, herein presented in accordance with different embodiments. While method 1100 and the steps described in FIG. 12 apply equally to both embodiments, steps 1102 and 1112 may be applied using either virtual image planes "virtually" located behind the display or on the retinal plane (via an eye focal plane (i.e. inside the eye)).

Moreover, method 1100 as illustrated in FIGS. 11 to 17D is designed to correct for spherical aberrations. However, other methods expanding on method 1100, for example that may also correct for astigmatism, will be described further below.

Moreover, for illustrative purposes, in this example, adjustment of a single image (i.e. the image as whole) is being implemented without consideration for distinct image portions. Further examples below will specifically address modification of the following example for adaptively adjusting distinct image portions.

Figure 11:
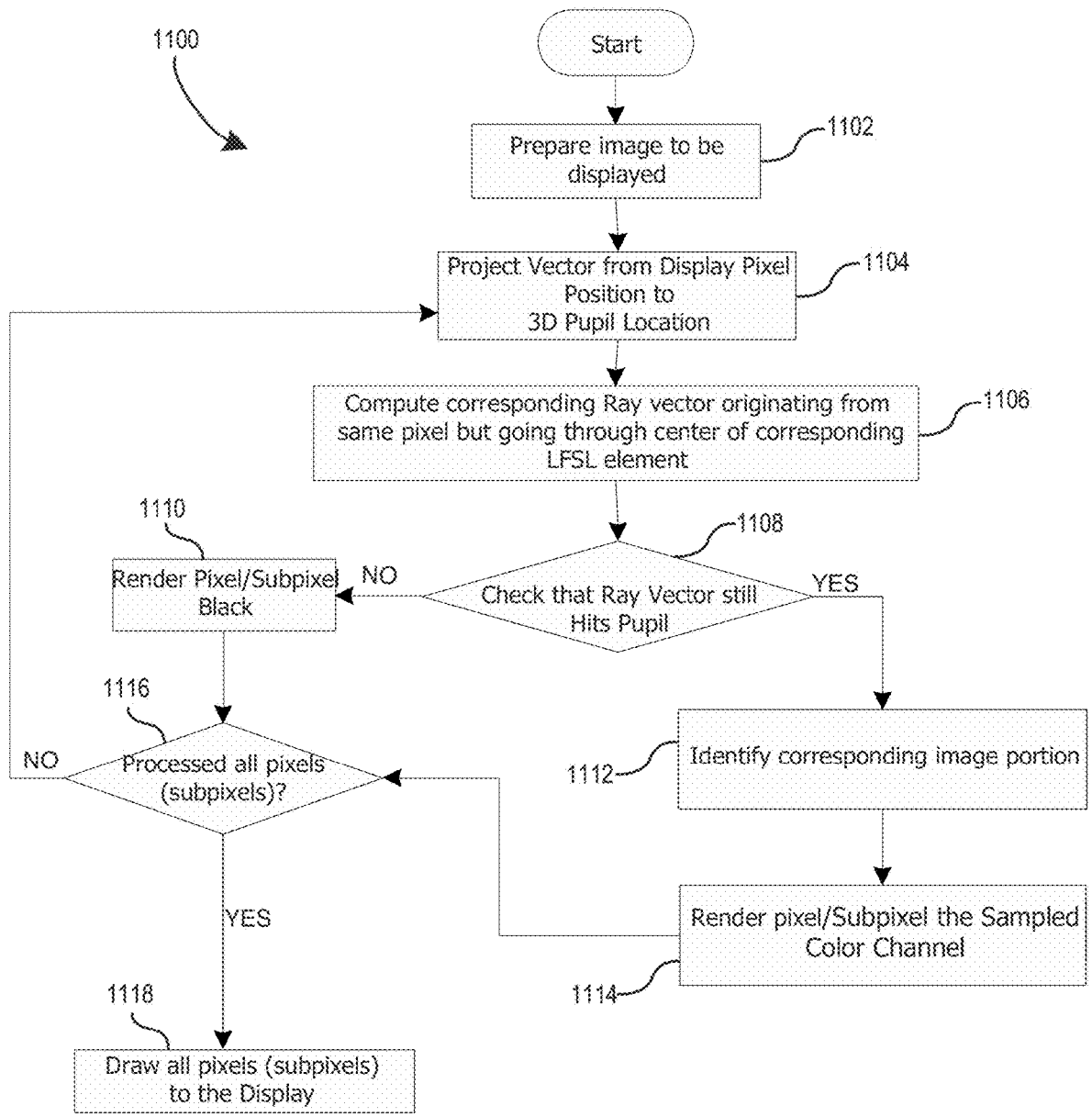
FIG. 11 is a process flow diagram of an illustrative ray-tracing rendering process, in accordance with one embodiment.
Figure 12:
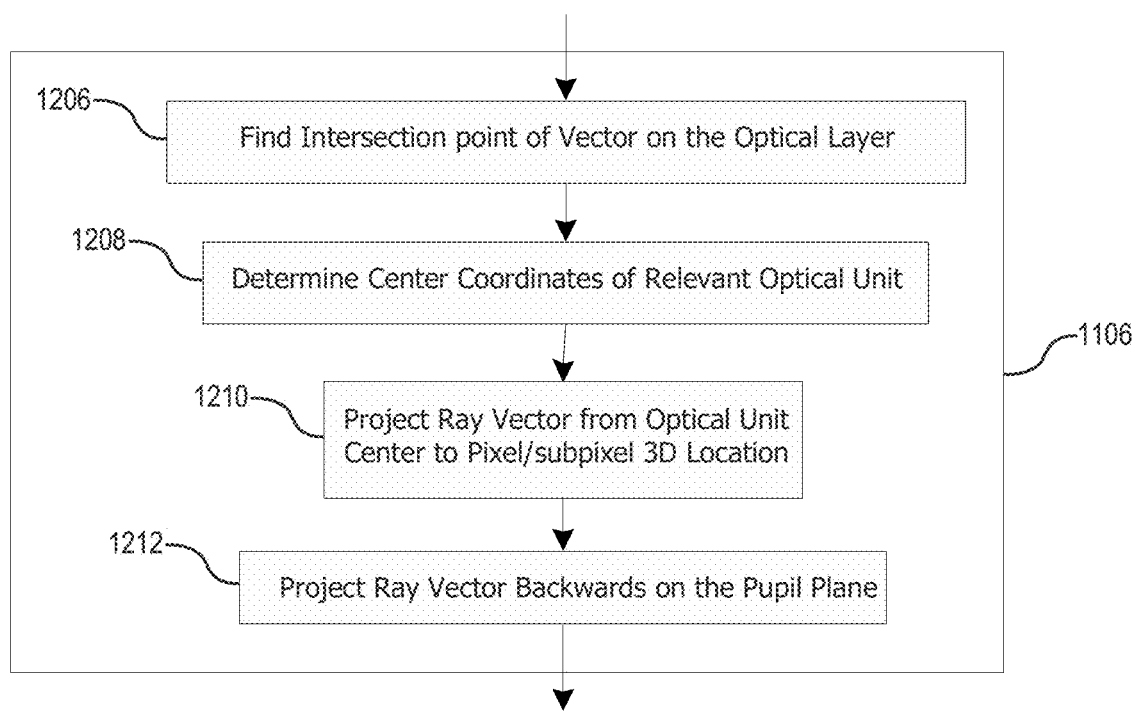
FIG. 12 is a process flow diagram illustrating a process step of FIG. 11, in accordance with one embodiment.

In the illustrated embodiment of FIG. 11, method 1100 begins with step 1102, in which the image to be displayed is pre-processed for subsequent ray-tracing steps. This includes numerically computing a location or position for a corresponding adjusted image surface or plane that corresponds to the required spherical dioptric power 1026 on which the image to be displayed will be mapped.

An exemplary ray-tracing methodology is described in steps 1104 to 1118 of FIG. 11, at the end of which the output color of each pixel of pixel display 108 is known so as to virtually reproduce the light field emanating from an input image 1020 positioned at the adjusted image plane. In FIG. 11, these steps are illustrated as a loop over each pixel in pixel display 108, so that each of steps 1104 to 1116 describes the computations done for each individual pixel. However, in some embodiments, these computations need not be executed sequentially, but rather, steps 1104 to 1116 may be executed in parallel for each pixel or a subset of pixels at the same time. Indeed, as will be discussed below, this exemplary method is well suited to vectorization and implementation on highly parallel processing architectures such as GPUs.

Figure 14A:
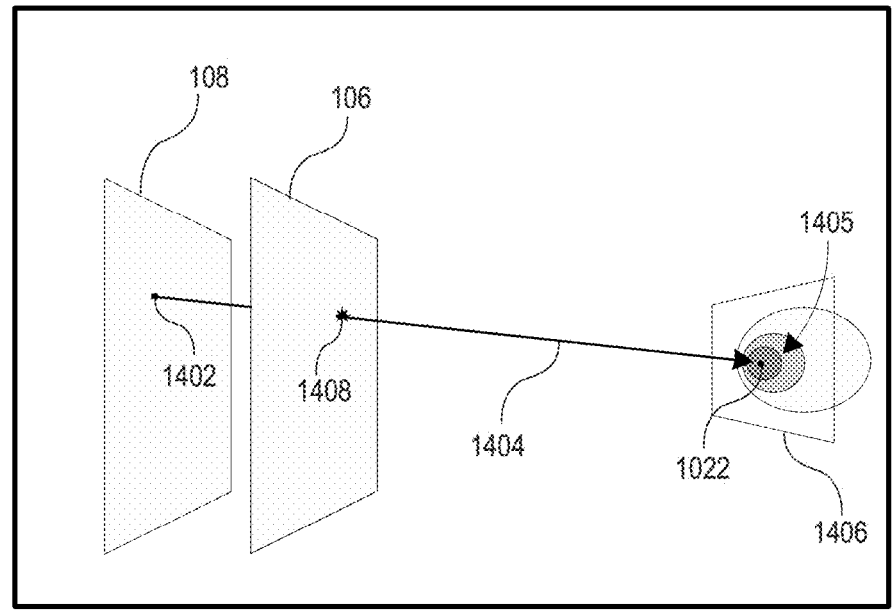
FIGS. 14A and 14B are schematic diagrams illustrating certain process steps of FIG. 11, in accordance with one embodiment.
Figure 14B:
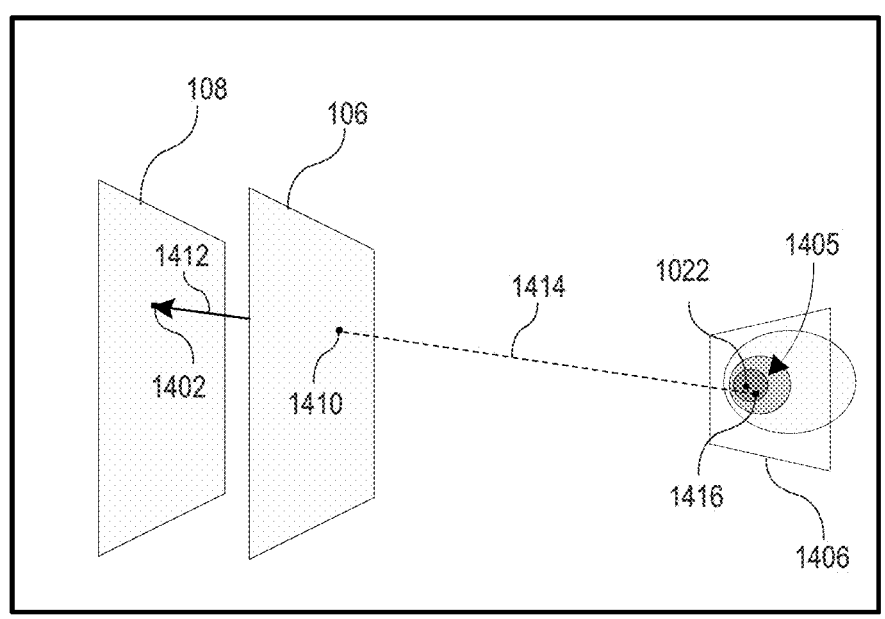

As illustrated in the schematic diagrams of FIG. 14A, in step 1104, for a given pixel 1402 in pixel display 108, a trial vector 1404 is first generated from the pixel's position to the pupil center position 1022 of the user's pupil 1405. As mentioned above, pupil center position 1022 may be acquired via eye/pupil tracker 110. In addition, a corresponding pupil plane 1406, which may be a flat 2D surface or plane in 3D space centered on pupil center position 1022, may be defined here as well. As shown in FIG. 14A, trial vector 1404, by construction, necessarily has to go through a corresponding optical unit of LFSL 106.

Once trial vector 1404 has been computed, in step 1106, a new Ray vector 1412 will be similarly generated from a center location/position 1410 of the corresponding optical unit comprising intersection point 1408 of LFSL 106 and pointing to pixel 1402. In this exemplary embodiment, step 1106 is detailed in the sub-steps 1206 to 1212 shown in FIG. 12.

Thus, in sub-step 1206, the location of intersection point 1408 of vector 1404 with the LFSL 106 is calculated as illustrated in FIG. 14A. In sub-step 1208, the coordinates of the center location 1410 of the optical element or unit of LFSL 106 closest to intersection point 1408 are computed. One way to efficiently compute this location is provided in related U.S. Pat. No. 10,394,322, the contents of which are incorporated herein by reference.

Once the position of the center 1410 of the optical element of LFSL 106 is known, in step 1210, as mentioned above, a normalized unit ray vector is generated from normalizing a ray vector 1412 originating from center position 1410 of LSFL 106 and extending to pixel 1402. This unit ray vector thus approximates the direction of the light field emanating from pixel 1402 through the center 1410 of this particular LFSL element, for instance, when considering a parallax barrier aperture or lenslet array (i.e. where the path of light travelling through the center of a given lenslet is not deviated by this lenslet). Further computation may be required when addressing more complex light shaping elements, as will be appreciated by the skilled artisan.

The orientation of ray vector 1412 will be used to find the portion of input image 1020 on the adjusted image plane, and thus the associated color, represented by pixel 1402. But first, in step 1212, ray vector 1412 is projected backwards (dotted line 1414 on FIG. 14B) to intersect with pupil plane 1406 at location 1416.

Going back to FIG. 11, at step 1108, method 1100 verifies that intersection point 1416 with pupil plane 1406 of projected ray vector 1414 is still located within user pupil entrance 1405 (i.e. that the user can still "see" it). Thus, once intersection point 1416 shown in FIG. 14B of projected ray vector 1414 with the pupil plane 1406 is known, the distance between the pupil center 1022 and intersection point 1416 within pupil plane 1406 may be calculated to determine if the deviation is acceptable, for example by using predetermined pupil size 1424 and verifying how far the projected ray vector intersection 1416 is from pupil center 1022 within pupil plane 1406.

If this deviation is deemed to be too large (i.e. light emanating from pixel 1402 channeled through optical element center 1410 is not perceived by pupil 1405), then in step 1110, method 1100 flags pixel 1402 as unnecessary and to simply be turned off or to render a black color.

In other embodiments, step 1108 may be modified so that instead of having a binary choice between the ray vector hitting the pupil or not, one or more smooth interpolation function (i.e. linear interpolation, Hermite interpolation or similar) may be used to quantify how far or how close intersection point 1416 is to pupil center 1022 within pupil plane 1406 and outputs a corresponding continuous value between 1 or 0. For example, the assigned value is equal to 1 substantially close to pupil center 1022 and gradually change to 0 as intersection point 1416 substantially approaches the pupil edges or beyond. In this case, the branch containing step 1110 may be ignored completely and step 1108 goes directly to step 1112. Then, at the end of step 1114, which will be discussed below, the pixel color value computed therein for pixel 1402 will be modified to be somewhere between the full color value identified therein or black, depending on the value of the interpolation function used at step 1108 (1 or 0).

In yet other embodiments, pixels found to illuminate a designated area around the pupil may still be rendered, for example, to produce a buffer zone to accommodate small movements in pupil location, for example, or again, to address potential inaccuracies, misalignments or to create a better user experience.

In the case where ray vector 1414 is within the pupil entrance (or if an interpolation function is used as discussed above), at step 1112, a corresponding image portion of input image 1020 located on the adjusted image plane and its corresponding color value are identified. As discussed above, two different but equivalent adjusted image planes may be used: a virtual image plane 1502 as shown schematically in FIG. 15 (i.e. positioned behind pixel display 108), or the retinal plane 1702 as shown in FIGS. 17A to 17D (i.e. behind user pupil 1405). Correspondingly, each variation of steps 1002 and 1112 are listed in the flow diagrams of FIGS. 13 and 16, respectively.

Figure 13:
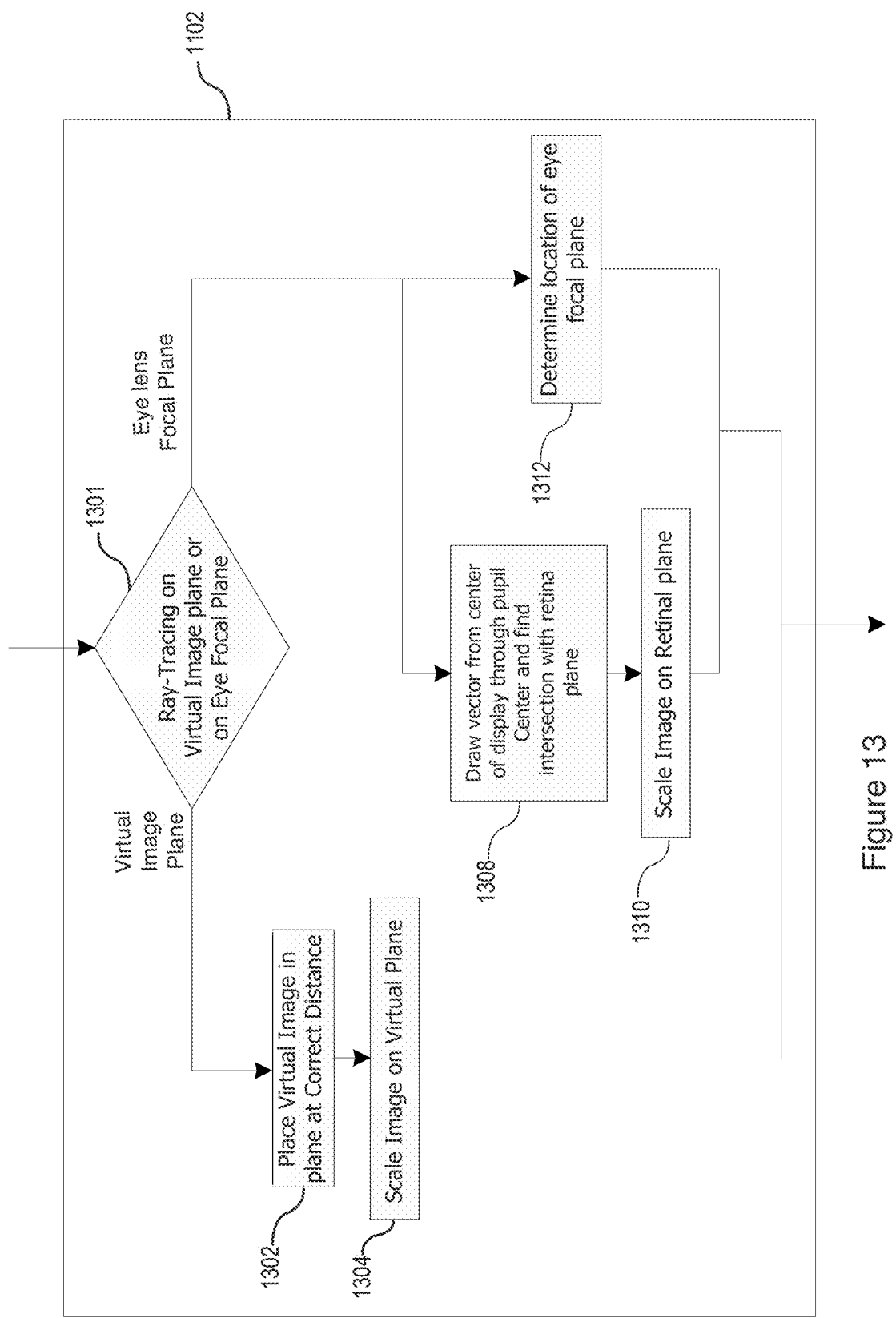
FIG. 13 is a process flow diagram illustrating certain process steps of FIG. 11, in accordance with one embodiment.
Figure 15:
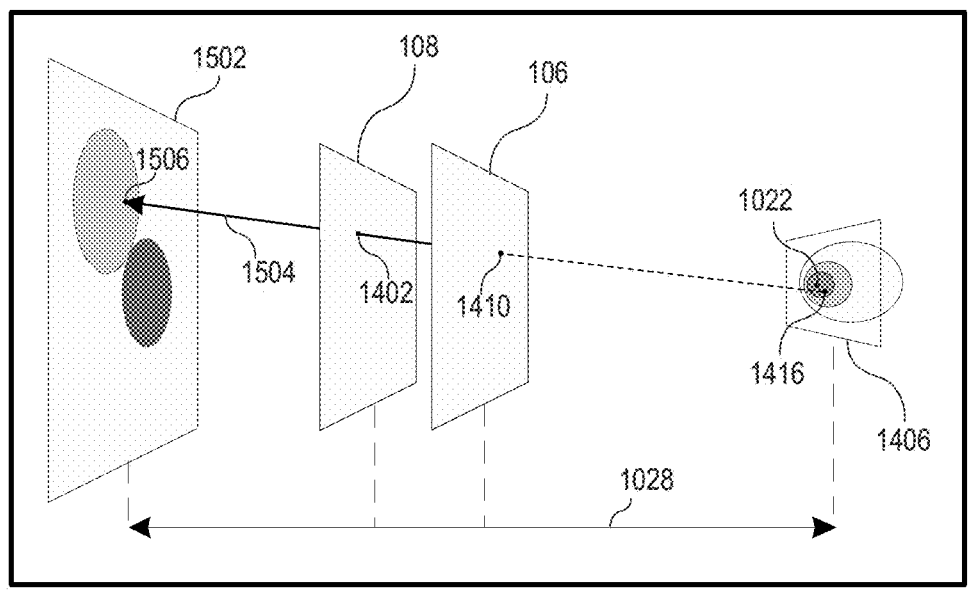
FIG. 15 is a schematic diagram illustrating the process steps of FIGS. 13 and 16, in accordance with one embodiment.

Thus, step 1102 is illustrated in FIG. 13, in accordance with one embodiment. In the case where virtual image planes are selected for ray-tracing in sub-step 1301, then as mentioned above ray-tracing is done using a virtual image plane 1502 as illustrated in FIG. 15. At sub-step 1302, the location or distance of virtual image plane 1502 from pupil plane 1406 may be computed as a function of spherical dioptric power 1026 (i.e. using the thin lens formula or other) and/or minimum reading distance 1028 (and/or related parameters). Then, at step 1304, input image 1020 is mapped onto virtual image plane 1502 so that its size of also scaled so to ensure that the perceived light field image correctly fills pixel display 108 when viewed by the distant user. An example is shown in FIG. 15 wherein virtual image plane 1502 is shown, as an example only, being located at a distance 1028 (in the z direction or depth) from pupil plane 1406, and the size of image 1020 is increased to avoid having the image as perceived by the user appear smaller than the display's size.

Figure 16:
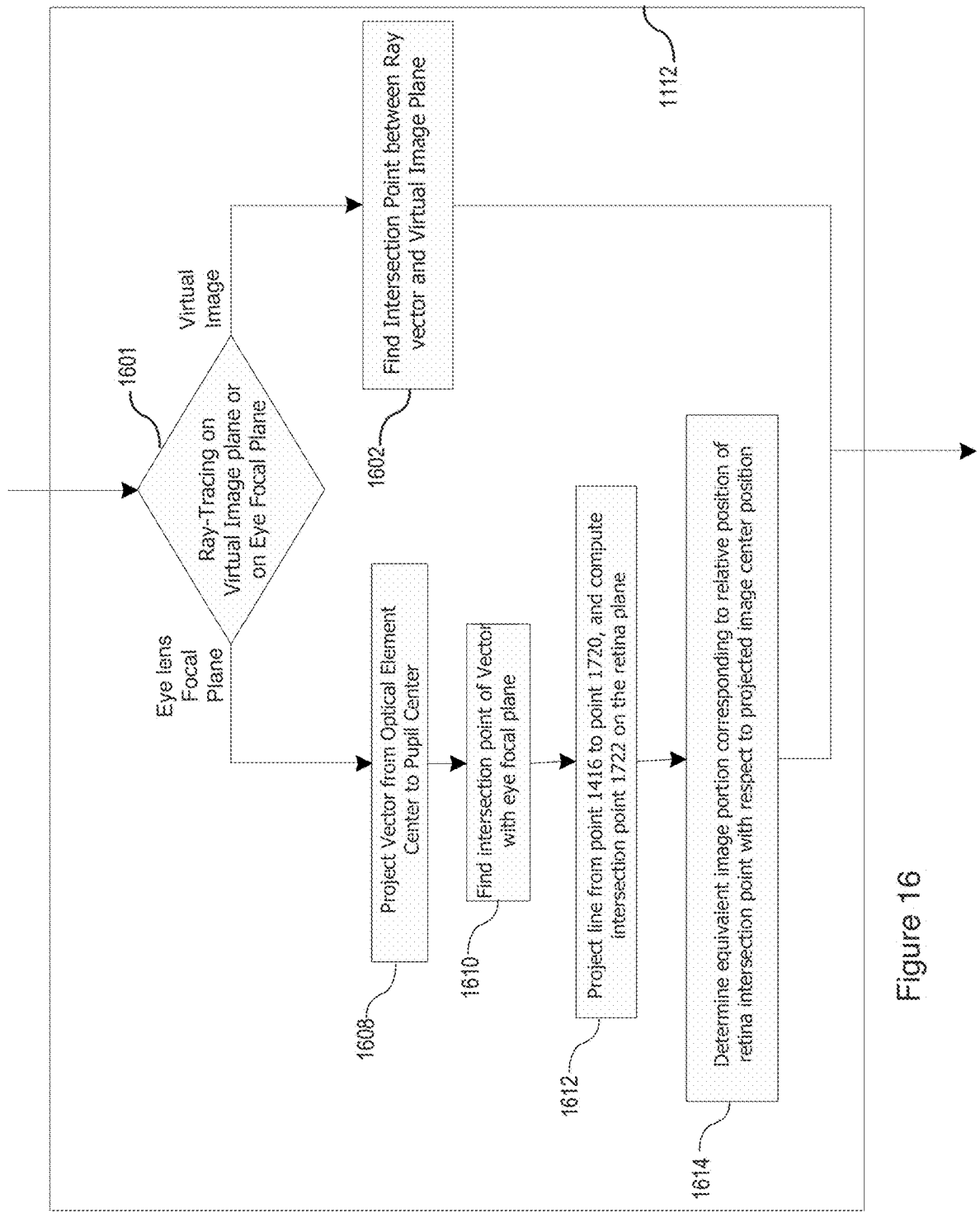
FIG. 16 is a process flow diagram illustrating certain process steps of FIG. 11, in accordance with one embodiment.

Continuing for the case of ray-tracing on virtual image plane 1502, the correct image portion is then identified in step 1112. So, as illustrated in FIG. 16, in this case sub-step 1601 leads to sub-step 1602. As schematically illustrated in FIG. 15, in sub-step 1602, ray vector 1412 is projected towards virtual image plane 1502 (shown as vector 1504 in FIG. 15) to find the position of the intersection point 1506. After this, the portion of image 1020 (and its associated colour channel) corresponding to intersection point 1506 on virtual image plane 1502 is identified.

As mentioned above, it may also be possible to use a retinal plane, herein defined as a 2D plane or surface substantially located at the location of the user's retina, as the adjusted image plane instead of virtual plane 1502.

Thus, in this case, illustrated schematically in FIGS. 17A to 17D, the adjusted image portion associated with a given pixel/subpixel is computed (mapped) on retinal plane 1702 instead of virtual image plane 1502 considered in the above example, again in order to provide the user with a designated image perception adjustment.

The skilled artisan will understand that a retinal plane may be defined in various ways. The exemplary embodiment described herein, the retinal plane 1702 is defined as a 2D plane located at a distance inside the eye equal to eye depth 1034 from the location of pupil center location 1022. It may also be taken to be parallel to pupil plane 1406, as illustrated in FIG. 17A to 17D, although it is not required to be so. It is meant to be an approximate location corresponding to the user's real retina.

Figure 17A:
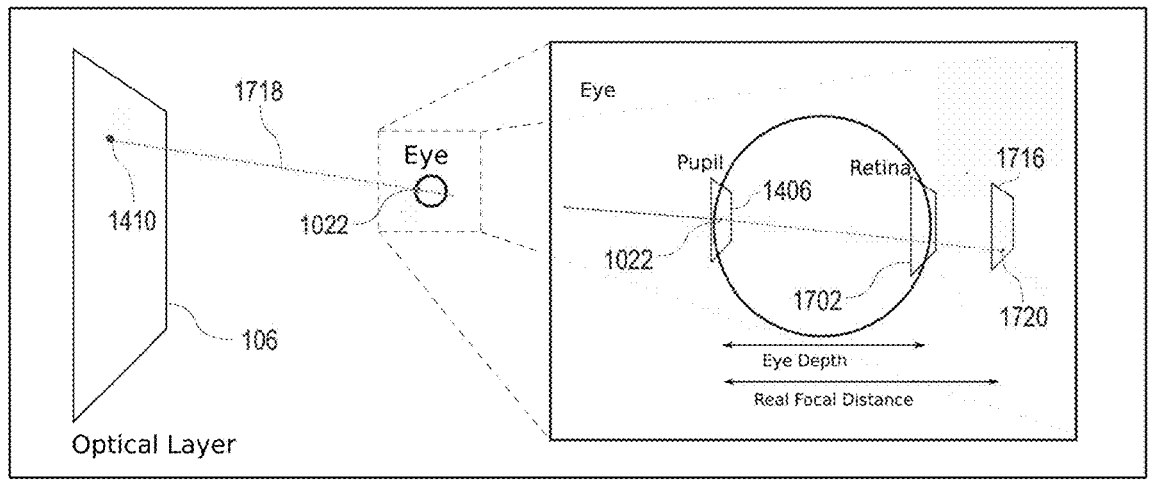
FIGS. 17A to 17D are schematic diagrams illustrating certain process steps of FIGS. 13 and 16, in accordance with one embodiment.
Figure 17B:
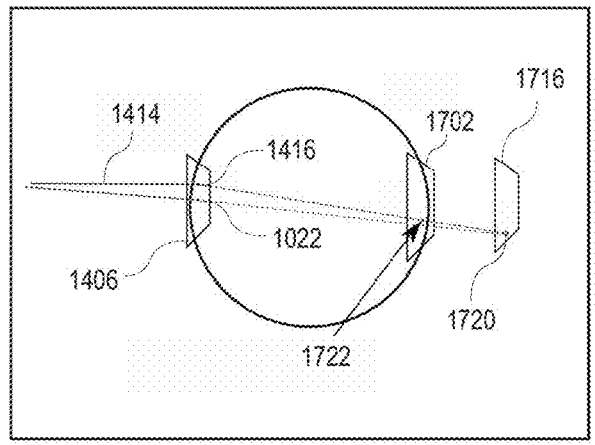
Figure 17C:
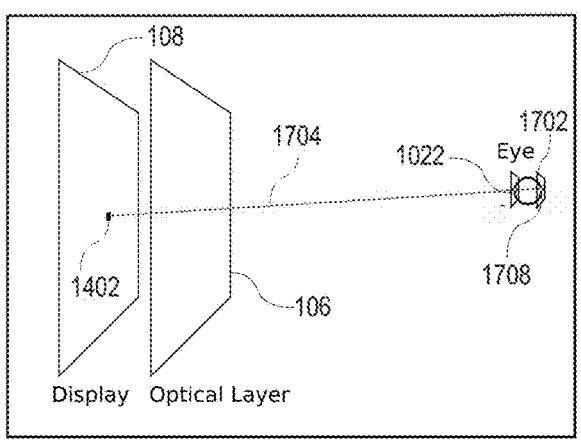
Figure 17D:
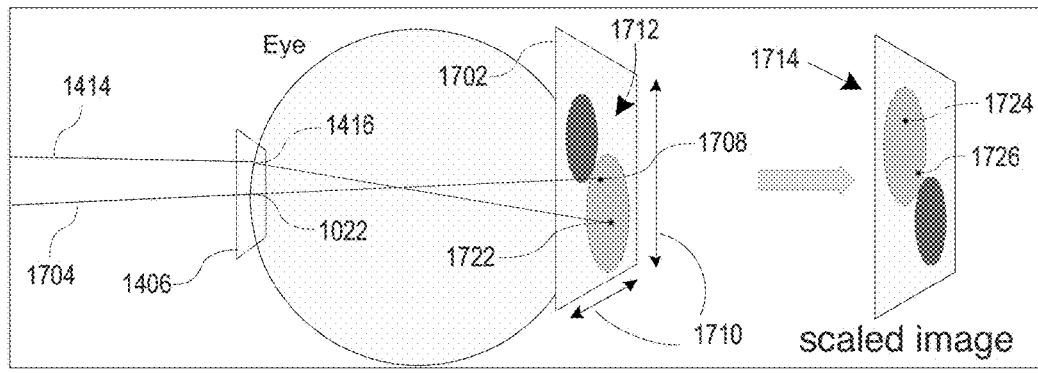

Thus, in the case where ray-tracing is done on retina image plane 1702, in step 1102 as shown in FIG. 13, sub-step 1301 leads to sub-step 1308, where a projected image center position on retinal plane 1702 is calculated. To do so, as illustrated in FIG. 17C, a vector 1704 is drawn originating from the center 1706 of pixel display 108 and passing through pupil center 1022. Vector 1704 is further projected beyond pupil plane 1405 onto retinal plane 1702, and the associated intersection point 1708 gives the location of the corresponding image center on retinal plane 1702. Once image center 1708 is known, in sub-step 1310 one can scale image 1020 to the x/y retina image size 1710, as illustrated schematically in FIG. 17D. In some embodiments, the required scaling may be computed by calculating the magnification of an individual pixel on retinal plane 1702, for example, which may be approximately equal to the x or y dimension of an individual pixel multiplied by the eye depth 1034 and divided by the absolute value of the distance to the eye (i.e. thus giving the magnification of the image portion created a pixel once focused by the eye lens on retinal plane 1702). An exemplary scaled inverted image 1712 on retinal plane 1702 is shown in FIG. 17D. Similarly, for comparison purposes, the input image 1020 may also normalized by the image x/y dimensions to produce a corresponding normalized input image 1714 having a width and height between −0.5 to 0.5 units, which may be compared to inverted scaled image 1712 which may also be similarly normalized.

In addition to sub-steps 1308 and 1310, sub-step 1312 is done independently to determine a location of a focal plane as produced by the user's eye for a given input value of spherical dioptric power 1026 (or minimum reading distance 1028). Thus, eye focal plane 1716 shown in FIGS. 17A and 17B is defined as the location where any light ray originating from optical unit center location 1410 would be focused by the user's eye. For a user with perfect vision, focal plane 1716 would be located at the same location as retinal plane 1702, but in the example shown in FIGS. 17A and 17B, as an example only, focal plane 1716 is located behind retinal plane 1702, which would be expected for a user with some form of farsightedness. The position of focal plane 1716 may be derived from the user's minimum reading distance 1028 or spherical dioptric power 1026, for example, by deriving therefrom the corresponding focal length of the user's eye. Other manually input or computationally or dynamically adjustable means may also or alternatively be considered to quantify this parameter.

Going back to FIG. 16, step 1112 in the case of ray-tracing on retinal plane 1702 has sub-step 1601 leading to sub-step 1608, illustrated schematically in FIG. 17A, where a vector 1718 is drawn from optical unit center 1410 to pupil center 1022. Then, in sub-step 1610, vector 1718 is projected further behind pupil plane 1406 onto eye focal plane 1716 where intersection point 1720 is identified.

The skilled artisan will note that any light ray originating from optical unit center 1410, no matter its orientation, will also be focused onto intersection point 1720, to a first approximation. Therefore, in some embodiments, the location 1722 on retinal plane 1702 onto which light entering the pupil at intersection point 1416 will converge may be approximated, at sub-step 1612, by drawing a straight line between intersection point 1416 where projected ray vector 1414 hits pupil plane 1406 and focal point 1720 on focal plane 1716, as illustrated in FIG. 17B. The intersection of this line with retinal plane 1702 (retina image point 1722) is thus the location on the user's retina corresponding to the image portion that will be reproduced by corresponding pixel 1402 as perceived by the user. Therefore, at sub-step 1614, by comparing the relative position of retinal point 1722 with the overall position of the projected image on the retinal plane 1702, the relevant adjusted image portion associated with pixel 1402 may be computed.

For example, the image portion position 1724 relative to retina image center position 1726 in the scaled coordinates (scaled input image 1714) corresponds to the inverse (because the image on the retina is inverted) scaled coordinates of retina image point 1722 with respect to retina image center 1708, as shown in FIG. 17D. Thus, the associated color with image portion position 1724 may be therefrom extracted and associated with pixel 1402.

Once step 1112 is finished, in step 1114, pixel 1409 is flagged as having the color value associated with the portion of image corresponding to intersection point 1506 in the case of ray-tracing on virtual image plane 1502 (as shown in FIG. 15) or in the case of ray-tracing on retinal plane 1702, to the image portion corresponding to intersection 1725 as shown in FIG. 17D.

At step 1116, a check is made to see if every pixel in pixel display 108 has been ray-traced. If not then method 1100 chooses another pixel 1402 and goes back to step 1104; if so, then the output color of all pixels has been determined and these are finally rendered in step 1118 by pixel display 108 to be viewed by the user, therefore presenting a light field corrected image. In the case of a single static image, the method may stop here. In yet other embodiments, pixels found to illuminate a designated area around the pupil may still be rendered, for example, to produce a buffer zone to accommodate small movements in pupil location, for example, or again, to address potential inaccuracies or misalignments.

As will be appreciated by the skilled artisan, selection of the adjusted image plane onto which to map the input image in order to adjust a user perception of this input image allows for different ray tracing approaches to solving a similar challenge, that is of creating an adjusted image using the light field display that can provide an adjusted user perception, such as addressing a user's reduce visual acuity. While mapping the input image to a virtual image plane set at a designated minimum (or maximum) comfortable viewing distance can provide one solution, the alternate solution may allow accommodation of different or possibly more extreme visual aberrations. For example, where a virtual image is ideally pushed to infinity (or effectively so), computation of an infinite distance becomes problematic. However, by designating the adjusted image plane as the retinal plane, the illustrative process steps of FIGS. 16A and 16B can accommodate the formation of a virtual image effectively set at infinity without invoking such computational challenges. Likewise, while first order aberrations are illustratively described with reference to FIG. 11, higher order or other optical anomalies may be considered within the present context, whereby a desired retinal image is mapped out and traced while accounting for the user's optical aberration(s) so to compute adjusted pixel data to be rendered in producing that image. These and other such considerations should be readily apparent to the skilled artisan.

While the computations involved in the above described ray-tracing algorithms (steps 1104 to 1116 of FIG. 11) may be done on general CPUs, it may be advantageous to use highly parallel programming schemes to speed up such computations. While in some embodiments, standard parallel programming libraries such as Message Passing Interface (MPI) or OPENMP may be used to accelerate the light field rendering via a general-purpose CPU, the light field computations described above are especially tailored to take advantage of graphical processing units (GPU), which are specifically tailored for massively parallel computations. Indeed, modern GPU chips are characterized by the very large number of processing cores, and an instruction set that is commonly optimized for graphics. In typical use, each core is dedicated to a small neighborhood of pixel values within an image, e.g., to perform processing that applies a visual effect, such as shading, fog, affine transformation, etc. GPUs are usually also optimized to accelerate exchange of image data between such processing cores and associated memory, such as RGB frame buffers. Furthermore, smartphones are increasingly being equipped with powerful GPUs to speed the rendering of complex screen displays, e.g., for gaming, video, and other image-intensive applications. Several programming frameworks and languages tailored for programming on GPUs include, but are not limited to, CUDA, OpenCL, OpenGL Shader Language (GLSL), High-Level Shader Language (HLSL) or similar. However, using GPUs efficiently may be challenging and thus require creative steps to leverage their capabilities, as will be discussed below.

In some embodiments, additional efficiencies may be leveraged on the GPU by storing the image data, for example image 1020, in the GPU's texture memory. Texture memory is cached on chip and in some situations is operable to provide higher effective bandwidth by reducing memory requests to off-chip DRAM. Specifically, texture caches are designed for graphics applications where memory access patterns exhibit a great deal of spatial locality, which is the case of the steps 1104 to 1116 of FIG. 11. For example, in method 1100, image 1020 may be stored inside the texture memory of the GPU, which then greatly improves the retrieval speed during step 1112 (including either one of the ray-tracing variants presented in FIGS. 13 and 16) where the color channel associated with the portion of input image 1020 is determined.

Moreover, while method 1100 presented above (and its associated variations) was discussed and illustrated as having each plane (i.e. virtual image plane 1502, pixel display 108, LSFL 106, pupil plane 1406, retinal plane 1702 or eye lens focal plane 1716) as being parallel with each other, this was only done as an example for clarity and to better describe the methodology associated therewith. Indeed, method 1100 as discussed may equally be applied to account for changes in the relative orientation between any one of those planes.

Figure 18:
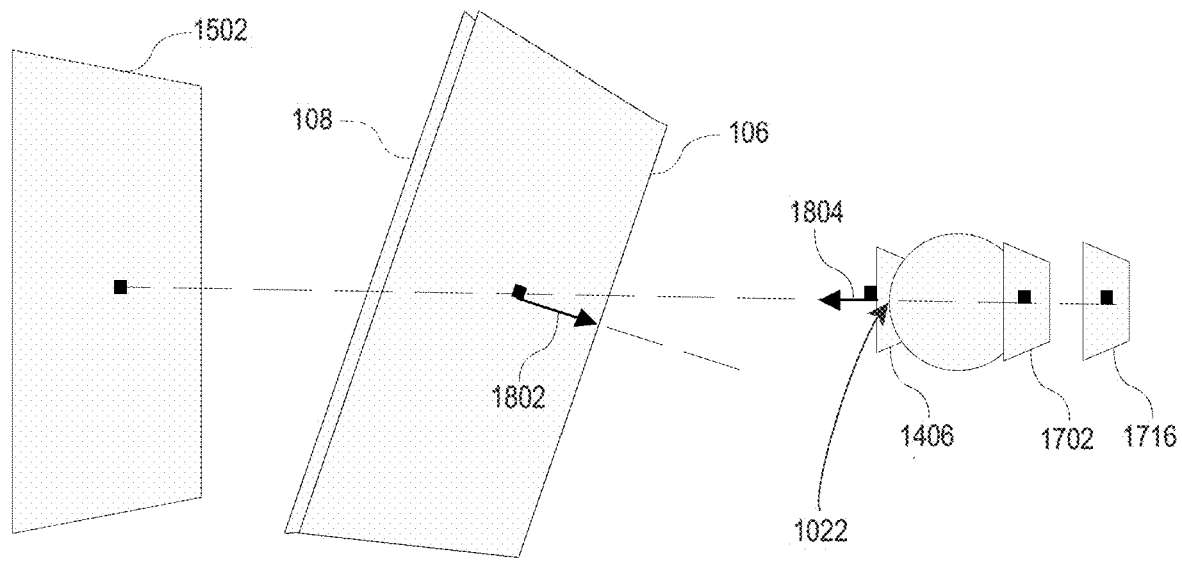
FIGS. 18 and 19 are schematic diagrams illustrating ray-tracing in the context of non-parallel planes, in accordance with one embodiment.
Figure 19:
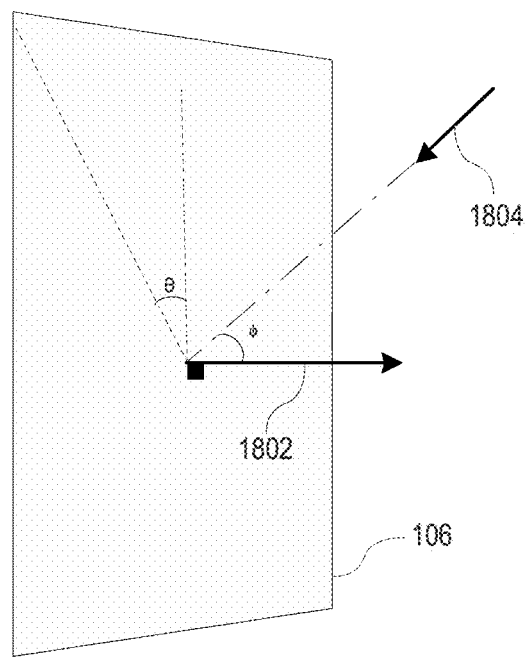

For example, and with reference to FIGS. 18 and 19, and in accordance with one exemplary embodiment, ray-tracing with non-parallel planes will now be discussed. In some embodiments, and as illustrated in FIG. 18, cases may be considered wherein the user is viewing the light field display at an angle. In this specific example, the ray-tracing method can therefore account for a change in orientation of the pupil plane 1406 with respect to the pixel display 108 and optical layer 106. In this example, other planes such as virtual image plane 1502, and retinal plane 1702 and focal plane 1716 may be taken to be parallel to pupil plane 1406. The relative difference in orientation between the two sets of planes is illustrated by using vector 1802 which is the normal vector to the plane of corresponding optical layer 106, and vector 1804 which is the normal vector to pupil plane 1406. The relative orientation between the two normal vectors is illustrated in FIG. 19, using polar and azimuthal angles.

The general orientation of pupil plane 1406 may be parametrized, for example, by using the 3D location of pupil center 1022 and a corresponding normal vector 1804. Normal vector 1804 may be taken to be, in some embodiments, equal to the gaze direction as measured by a gaze tracking system or similar, as will be discussed below.

Once the relative position and orientation of pupil plane 1406 is determined, the relative position/orientation of all remaining planes (parallel or non-parallel) may be determined and parametrized accordingly. Planes that are parallel share the same normal vector. From there, the method 1100 and its variants described above may be applied by finding the intersection point between an arbitrary vector and an arbitrarily oriented plane, as is done for example at steps 1206, 1212, 1602, 1610, 1612 for example.

In the illustrated example of FIG. 18, the position of virtual image plane 1502 may be computed using spherical dioptric power 1026 (and/or minimum reading distance 1028 and/or related parameters) but from the position of pupil plane 1406 and along the direction vector 1804.

To extract normal vector 1804 of pupil plane 1406, the eye tracking methods and systems described above may be used or modified to further provide a measure of the eye's gaze direction (e.g. gaze tracking). As discussed above, there are many known eye tracking methods in the art, some of which may also be used for gaze-tracking. For example, this includes Near-IR glint reflection methods and systems or methods purely based on machine vision methods. Hence, in some embodiments, pupil plane 1406 may be re-parametrized using an updated 3D location of pupil center 1022 and an updated normal vector 1804 at each eye tracking cycle. In other embodiments, a hybrid gaze tracking/pupil tracking system or method may be used wherein gaze direction (e.g. normal vector 1804) is provided at a different interval than pupil center location 1022. For example, in some embodiments, for one or more cycles, only the 3D pupil center location 1022 may be measured and an old gaze direction vector may be re-used or manually updated. In some embodiments, an eye model or similar may be constructed to map a change in measured pupil center location 1022 to a change in the gaze direction vector without relying on the full capabilities of the gaze tracking system or method. Such a map may be based on one or more previous gaze tracking measurements. In any case, by measuring/determining the 3D pupil center location 1022 and normal vector 1804, the pupil plane may be parametrized accordingly.

Note that in FIG. 18, pixel display 108 and optical layer 106 are shown as being parallel for simplicity, but other embodiments may envision optical layer 106 to be non-parallel to display 108 as well. This doesn't change the general scope of the present discussion, as long as the relative angle between them is known. For example, such an angle may be pre-determined during manufacturing or measured in real-time using one or more sensors (for example in the case where optical layer 106 may be mobile). Similarly, other planes like for example retinal plane 1702 may also be made to be non-parallel to the pupil plane, depending on the user's eye geometry.

Figure 20A:
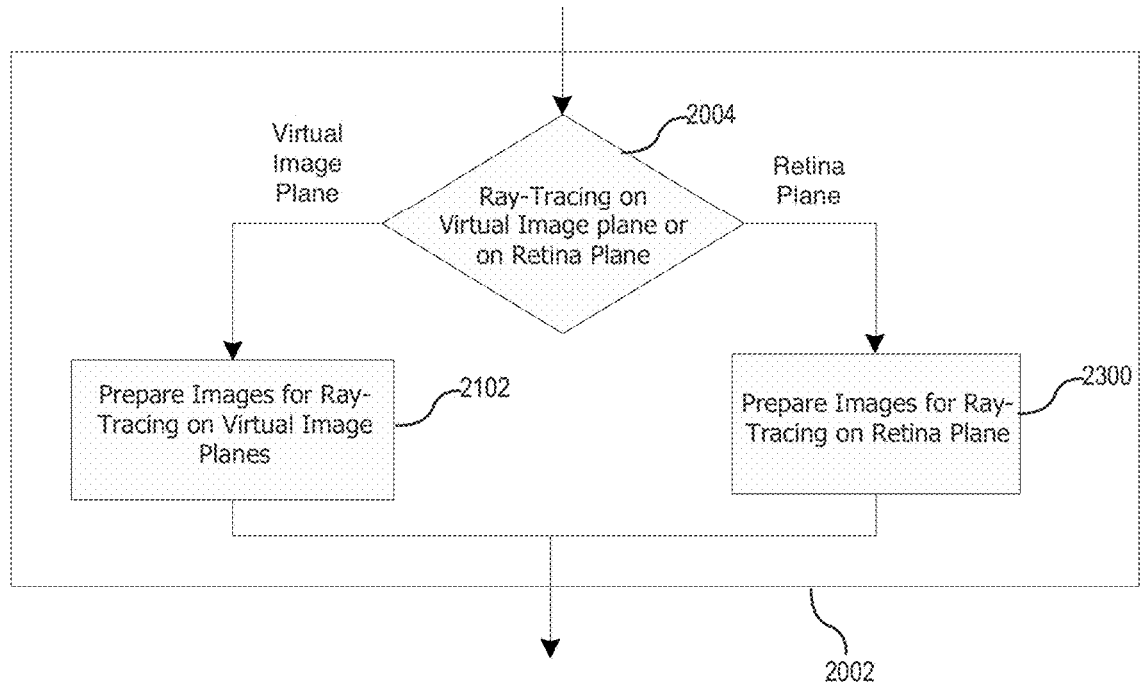
FIGS. 20A and 20B are process flow diagrams of certain process steps of FIG. 11 for rendering a light field originating from multiple distinct virtual image planes, in accordance with one embodiment.
Figure 20B:
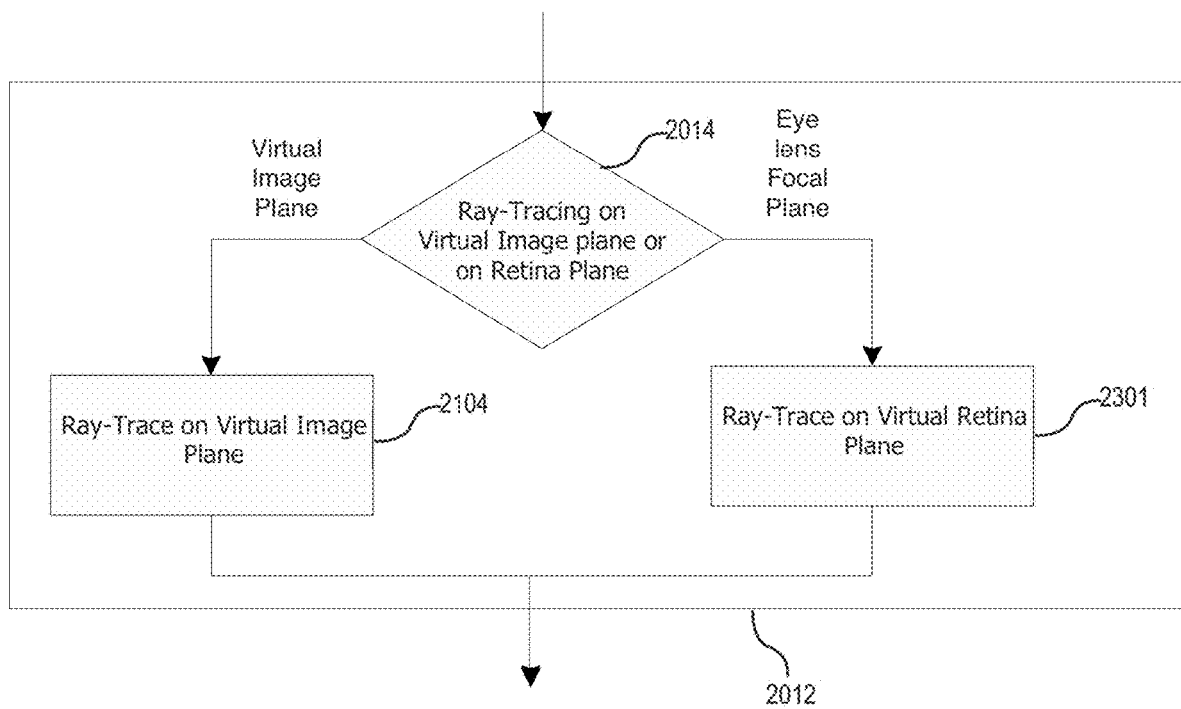

With reference to FIGS. 20A to 22D and in accordance with one embodiment, a modified embodiment of method 1100 operable to render multiple images or image portions on multiple adjusted distinct image planes simultaneously via an array of light field shaping elements, or light field shaping layer (LFSL) thereof, will now be discussed. Thus, step 2002 shown in FIG. 20A is meant to replace step 1102 in method 1100, while step 2012 of FIG. 20B replaces step 1112. This is because the previously above-described steps 1102 and 1112 were directed to correcting a single image by directly or indirectly modifying the location of the virtual image plane and/or eye focal plane. In contrast, the below-described embodiments of steps 2002 and 2012 are directed to a light field display which is generally operable to display multiple image planes at different locations/depths/aberrations simultaneously. Thus, in step 2002, at sub-step 2004, the method continues to sub-step 2102 (illustrated in FIG. 21A) if ray-tracing is done using the virtual image plane or if ray-tracing is done using the retinal plane then sub-step 2300 is used (illustrated in FIG. 23A). Similarly, as shown in FIG. 20B, from sub-step 2014, the method proceeds to sub-step 2104 in the case of ray-tracing to virtual image plane (illustrated in FIG. 21B) or to sub-step 2301 (illustrated in FIG. 23B if ray-tracing is done using the retinal plane).

Unlike known stereoscopic effects, the methods as herein described may be implemented to generate varying depth perceptions within a same eye, that is, allowing for the monoscopic viewing of an input to exhibit multiple distinct image perception adjustments (i.e. multiple juxtaposed and/or overlapping depths, enhancements or like optical adjustments, compensations, etc.). For example, in some embodiments, distinct image planes may be juxtaposed such that different sides or quadrants of an image, for example, may be perceived at different depths. In such embodiments, a different effective vision correction parameter (e.g. diopter), or depth, may be applied, to each portion or quadrant. While this approach may result in some distortions or artefacts at the edges of the areas or quadrants, depending on the image data to be rendered along these edges, such artefacts may be negligible if at all perceivable. In other embodiments, however, different image portions may be at least partially superimposed such that portions at different depths, when viewed from particular perspectives, may indeed appear to overlap. This enables a user to focus on each plane individually, thus creating a 2.5D effect. Thus, a portion of an image may mask or obscure a portion of another image located behind it depending on the location of the user's pupil (e.g. on an image plane perceived to be located at an increased distance from the display than the one of the first image portion). Other effects may include parallax motion between each image plane when the user moves.

Figure 23A:
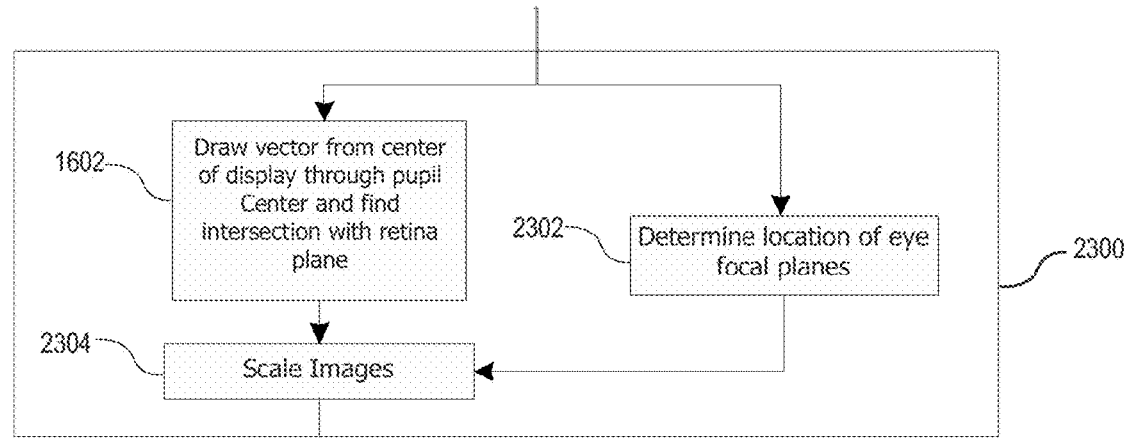
FIGS. 23A and 23B are process flow diagrams of certain process steps of FIG. 11 for rendering a light field originating from multiple distinct focal planes, in accordance with one embodiment.
Figure 23B:
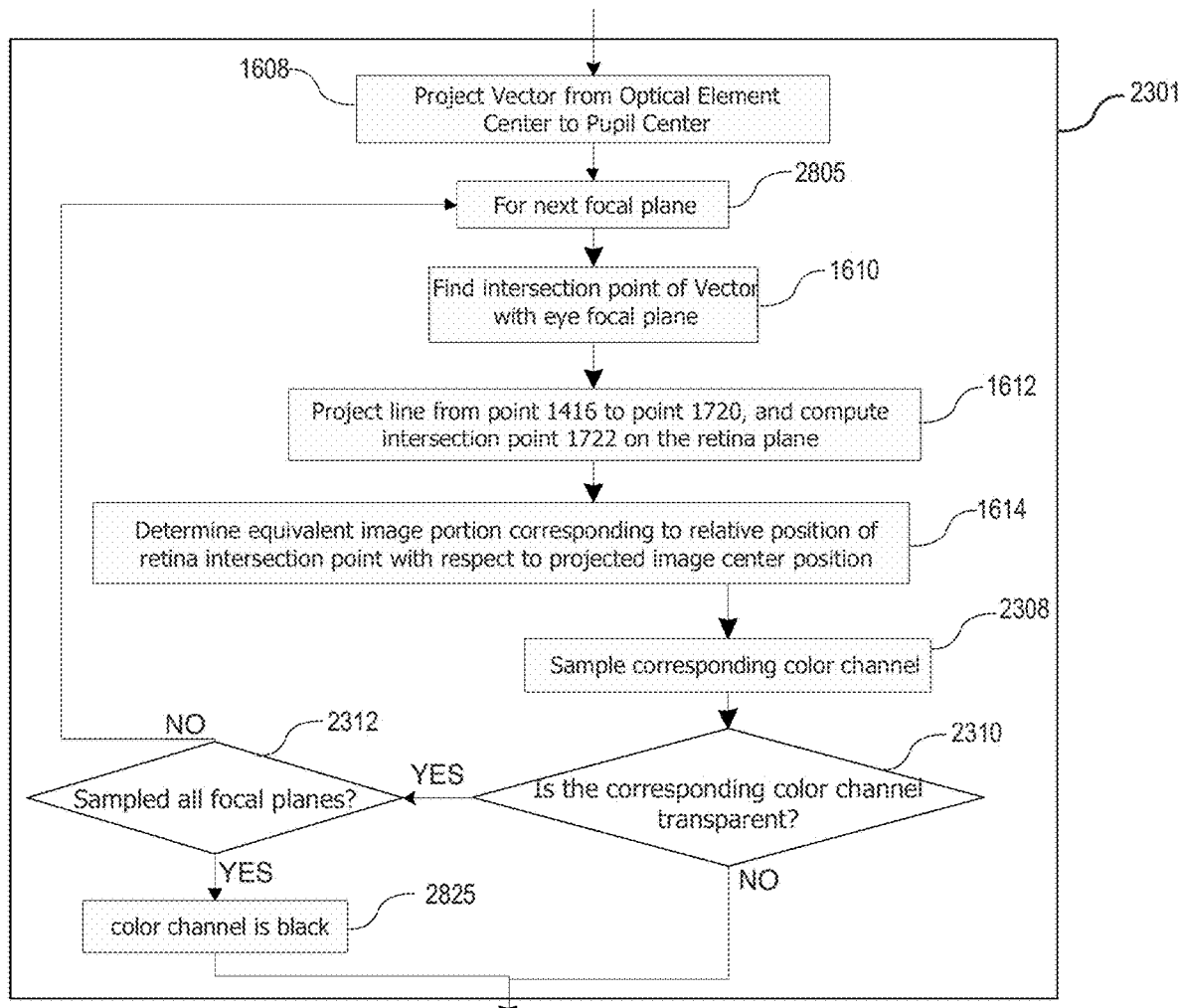

As mentioned above, steps 2102 and 2104 of FIGS. 21A and 21B are directed towards ray-tracing on one or more virtual image plane only, while steps 2300 and 2301 of FIGS. 23A and 23B are directed towards ray-tracing on the retinal plane.

For example, to account for multiple distinct image planes, input image 1020 of input variables 1004 may also include, in addition to pixel data, variable dioptric powers or perceptive "depth" information or parameters. Thus, any image or image portion may have a respective depth indicator. Thus, at sub-step 2106, a set of multiple virtual image planes may be defined, at sub-step 2108, which includes deriving their respective (virtual) location, similarly to sub-step 1302. On these planes, images or image portions may be present. Areas around these images may be defined as transparent or see-through, meaning that a user would be able to view through that virtual image plane and see, for example, images or image portions located behind it. At sub-step 2108, any image or image portion on each of these virtual image planes may be optionally scaled to fit the display, similarly as described for sub-step 1304 for a single image plane.

In the previous example shown in FIG. 15, a single virtual image plane 1502, showing an exemplary input image 1020 comprising two circles, was used. In contrast, FIGS. 22A to 22D show an example wherein each circle is located on its own virtual image plane (e.g. original virtual plane 1502 with new virtual image plane 2202). The skilled technician will understand that two planes are shown here only as an example and that the method steps described herein apply equally well to any number of virtual planes. The only effect of having more planes is a larger computational load.

Going back to 21B, in step 2104, an iteration is done over the set of virtual image planes to compute which image portion from which virtual image plane is seen by the user. Thus, at sub-step 2110 a virtual image plane is selected, starting from the plane located closest to the user. Then step 1602 proceeds as described previously for that selected virtual plane. At sub-step 2112 the corresponding color channel of the intersection point identified at step 1602 is sampled. Then at sub-step 2114, a check is made to see if the color channel is transparent. If this is not the case, then the sampled color channel is sent to step 1114 of FIG. 11, which was already described and where the color channel is rendered by the pixel/subpixel. An example of this is illustrated in FIGS. 22A and 22B, wherein a user is located so that a ray vector 2204 computed passing through optical element center location 1410 and pixel/subpixel 1402 intersects virtual image plane 1502 at location 1506. Since in this example this location is non-transparent, this is the color channel that will be assigned to the pixel/subpixel. However, as this example shows, this masks or hides parts of the image located on virtual image plane 2202. Thus, an example of the image perceived by the user is shown in FIG. 22B.

Figure 21A:
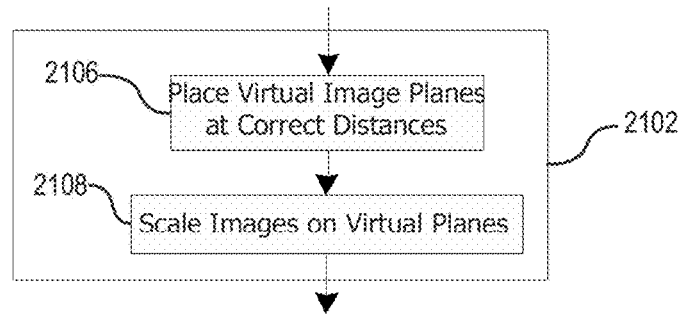
FIGS. 21A and 21B are process flow diagrams of certain process steps of FIGS. 20A and 20B for rendering a light field originating from multiple distinct virtual image planes, in accordance with one embodiment.
Figure 21B:
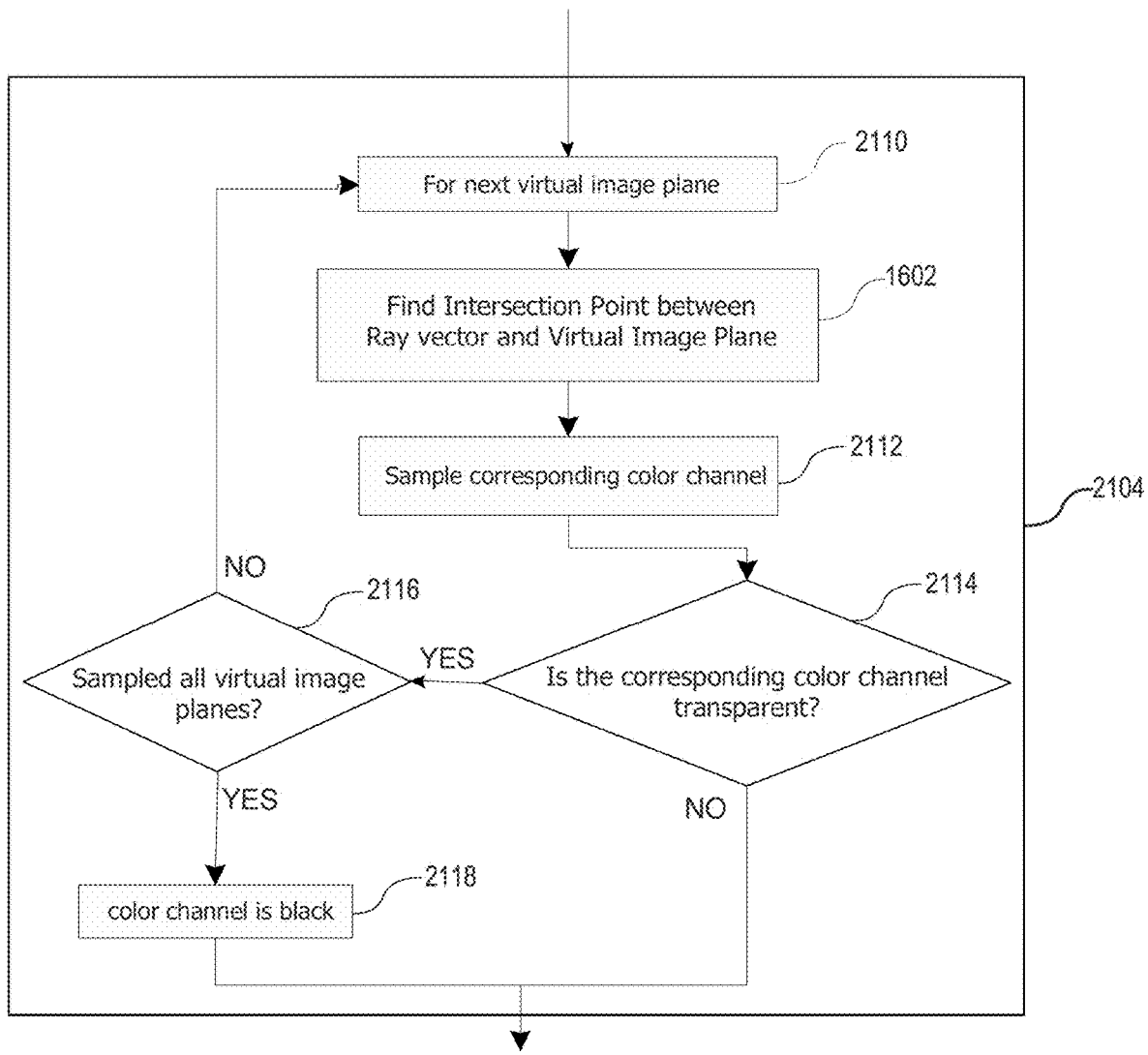

Going back to FIG. 21B, at sub-step 2114 if the color channel is transparent, then another check is made at sub-step 2116 to see if all virtual image planes have been iterated upon. If this is the case, then that means that no image or image portion is seen by the user and at sub-step 2118, for example, the color channel is set to black (or any other background colour), before proceeding to step 1114 of FIG. 11. If however at least one more virtual image plane is present, then the method goes back to step 2110 and selects that next virtual image plane and repeats sub-steps 1602, 2112 and 2114. An example of this is illustrated in FIG. 22C, wherein a user is located so that a distinct ray vector 2204 computed passing through optical element center 2206 of LFSL 106 and pixel/subpixel 2208 of pixel display 108 first intersects at location 2210 of virtual image plane 1502. Since, in this example, this location is defined to be transparent (i.e. not on the circle), the method checks for additional virtual image planes (here plane 2202) and extends vector 2204 so as to compute intersection point 2212, which is now non-transparent (i.e. on the circle), and thus the corresponding color channel is selected. An example of the image perceived by the user is shown in FIG. 22D.

Similarly, steps 2300 and 2301 of FIGS. 23A and 23B substantially mirrors steps 2102 and 2104, respectively, described in FIGS. 21A and 21B, but are herein applied to be used with two or more eye focal planes (e.g. for raytracing the image on retinal image plane 1702). Thus, we see that the method iterates, after sub-step 1608, over all designated image planes, each corresponding to a different eye focal plane, starting from the plane corresponding to an image located closest to the user. Thus, a new eye focal plane is selected at sub-step 2306, which is used for sub-steps 1610 to 1614 already described above. Once the corresponding image portion is determined at sub-step 1614, at sub-step 2308, the corresponding pixel/subpixel color channel is sampled. Then at sub-step 2310, if the color channel is non-transparent, then the method continues to step 1114 of FIG. 11, wherein the pixel/subpixel is assigned that color channel. However, if the image portion is transparent, then the method iterates to the eye focal plane corresponding to the next designated image plane. Before this is done, the method checks at sub-step 2312 if all the eye focal planes have been iterated upon. If this is the case, then no image portion will be selected and at sub-step 2314 the color channel is set to black, for example, before exiting to step 1114. If other eye focal planes are still available, then the method goes back to sub-step 2306 to select the next eye focal plane and the method iterates once more.

Figure 24A:
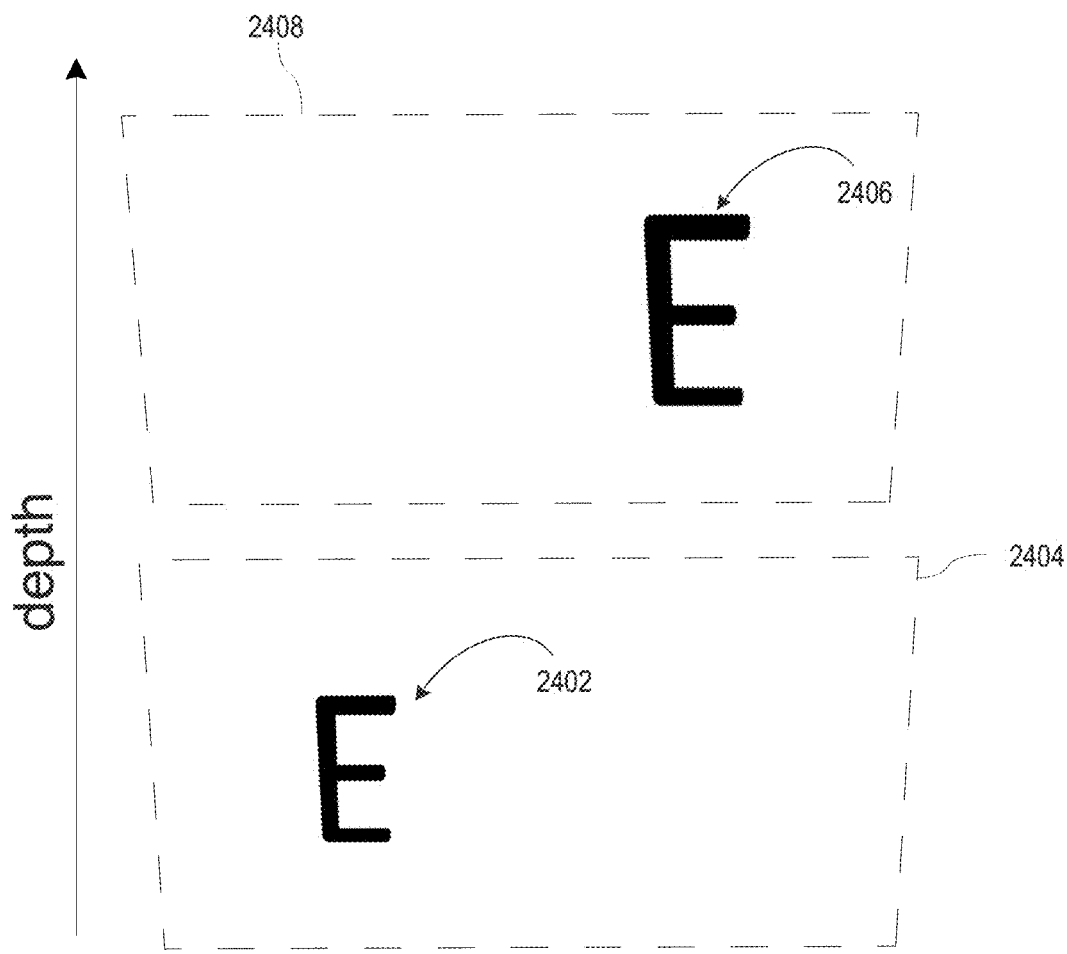
FIGS. 24A and 24B are schematic diagrams illustrating an example of a subjective visual acuity test using the ray-tracing rendering process of FIG. 23A or FIG. 23B, in accordance with one embodiment.
Figure 24B:
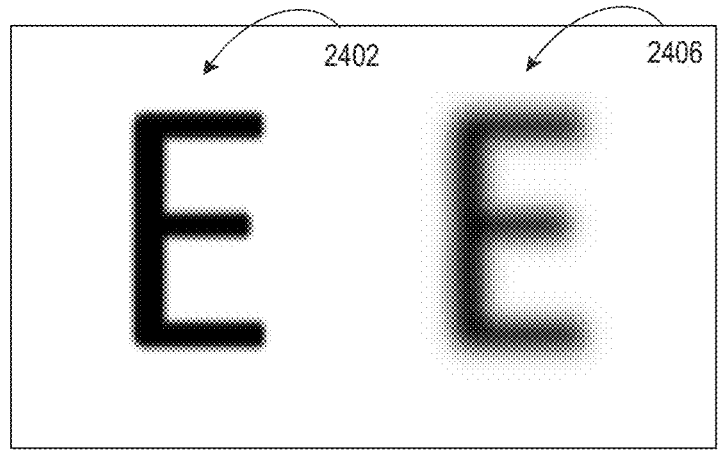

In some embodiments, as mentioned above, steps 2102, 2104 or 2300 and 2301 for multiple designated image planes of FIGS. 21A-B (on virtual planes) or FIGS. 23A-B (retinal plane) may be used to implement a phoropter/refractor device to do subjective visual acuity evaluations. For example, as illustrated in FIGS. 24A and 24B, and similarly to FIG. 9, different optotypes (e.g. letters, symbols, etc.) may be displayed simultaneously but at different perceived depths, to simulate the effect of adding a refractive optical component (e.g. change in focus/optical power). In FIG. 24A, two images of the same optotype (e.g. letter E) are displayed, each on their own designated image plane (e.g. here illustrated as virtual image planes as an example only). In this example, image 2402 is located on designated image plane 2404 while image 2406 is located on designated image plane 2408, which is located further away. Optionally, as illustrated herein, the size of the image may be increased with increased depth so that all images displayed are perceived to be of a similar relative size by the user. In FIG. 24B, we see an example of the perception of both images as perceived by a user with reduced visual acuity (e.g. myopia), for example, wherein the image closest to the user is seen to be clearer. Thus, a user could be presented with multiple images (e.g. 2 side-by-side, 4, 6 or 9 in a square array, etc.) and indicate which image is clearer and/or and most comfortable to view. An eye prescription may then be derived from this information.

As mentioned above, the systems and methods discussed herein may also be adapted to correct or compensate for the presence of HOAs. This is generally done by digitally simulating the presence of a "virtual" optical element specifically tailored or constructed so as to reproduce the effect of said HOAs. Such a "virtual" optical element will be referred to herein as a phase element, since its effect on an incoming wave front is to introduce a phase shift or phase profile corresponding to one or more known HOAs. Thus, by considering the effects of such a phase element on each incoming ray generated by a light field display, it is possible to generate an image that compensates for the user's HOAs and thus allows the user to clearly perceive the image. Notably, although the focus of the methods described below is one treating for HOAs, the methods using the phase element may generally be applied, without limitation, to simulate other kinds of optical aberrations, such as astigmatism, as will be made clear below.

The use of a virtual phase element is schematically illustrated in FIG. 25, wherein an incoming source of light herein pictured as a plane wave front 2502 is refracted by a phase element 2500, which is tailored or constructed so as to generate an aberrated output wave front 2504. Since a wave front is defined as a surface of common phase, a corresponding set of light rays may be defined so as to be perpendicular or normal to the wave front surface (incoming rays 2506 and refracted rays 2508). The difference between aberrated output wave front 2504 and input wave front 2502 is in the phase shift caused by one or more HOAs (or aberrations in general) of phase element 2500. Thus, by constructing or defining phase element 2500 so as to reproduce the required phase shift, it is possible to compute therefrom the change in orientation of input rays 2506 to output rays 2508 and construct a light field image using a light field display that compensates for these HOAs (or aberrations in general).

Notably, phase element 2500 is herein illustrated as being parallel to the (x,y) axis as an example only. More general relative orientations between phase element 2500 and for example light field display 104 or pupil plane 1406 (not shown here) may be assumed, without limitation, as will be noted further below.

As schematically illustrated in FIGS. 26A and 26B, in some embodiments, phase element 2500 may be used to model or digitally replicate HOAs (or aberrations in general) in the user's eye, in which case phase element 2500 may be virtually positioned at the user's pupil, as illustrated in FIG. 26A. In other embodiments, it may be desirable to model HOAs (or wavefront modifications) of a real physical optical element located in front of the eye, and thus phase element 2500 may be positioned somewhere in-between the eye and the light field display, as shown in FIG. 26B. In some embodiments, multiple phase elements 2500 may be deployed simultaneously.

Phase element 2500 may be defined or constructed in different ways and may have different geometries or optical characteristics, so long as it correctly models or reproduces the corresponding aberrations of interest. Some non-limiting examples are given below.

Figure 27A:
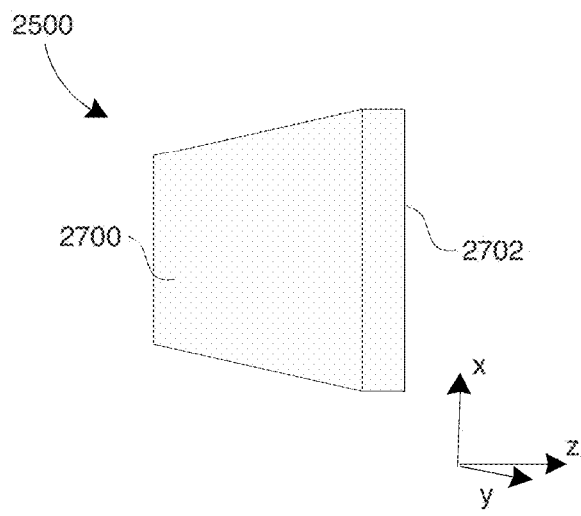
FIGS. 27A to 27D are schematic diagrams illustrating different exemplary shapes or profiles of the phase element of FIG. 25, in accordance with one embodiment.
Figure 27B:
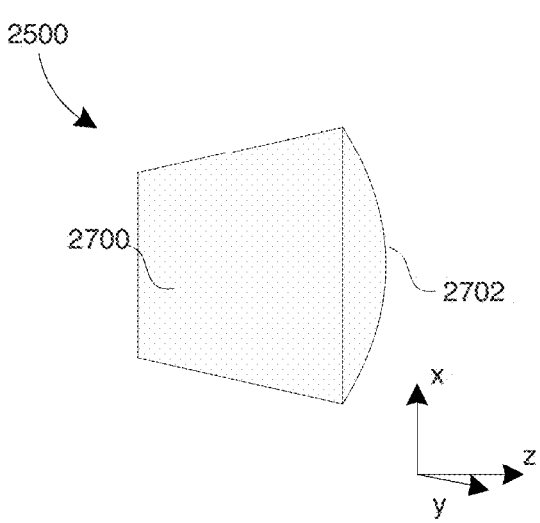
Figure 27C:
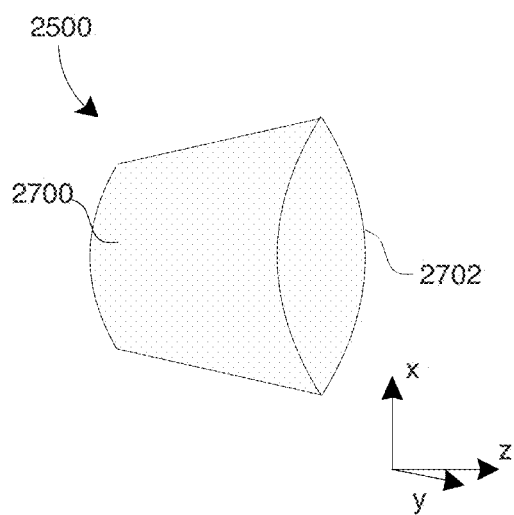

For example, as seen in FIG. 27A, in some embodiments, phase element 2500 may comprise a first incident surface 2700 (facing the light field display), a second surface 2700 (facing the user). However, different combinations of surface profiles may be considered, without limitation. For example, in some embodiments, as in the illustrated exemplary embodiment of FIG. 27B, first incident surface 2700 may be defined to be flat with a normal vector orientated in the z direction, and only the second surface 2702 having a variable shape profile. Other embodiments may include both surfaces having a variable shape or profile, as illustrated in FIG. 27C.

Figure 27D:
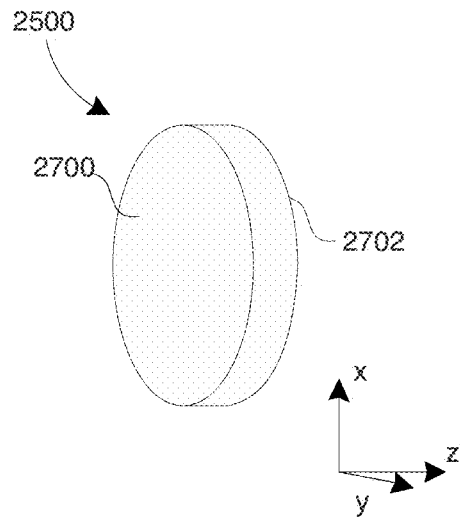

In addition, phase element 2500 is not limited to having a rectangular shape, as was illustrated in FIGS. 26A-C and 27A only as an example. Different considerations may be taken into account to determine the shape, size or extension of phase element 2500 in the (x,y) and z dimensions. In some embodiments, for example when Zernike polynomials are used to generate the shape of phase element 2500, a disk shape, as in FIG. 27D, may be used, so as to better align with the pupil shape and the azimuthal and radial dependent forms of the Zernike polynomials. Generally, the size in the (x,y) plane will be chosen so that all light rays projected from the light field display may be properly refracted. For example, in the case where phase element 2500 is placed at the pupil plane 1406, (discussed further below), the x, y coordinates may be chosen as being equal to a factor of the pupil radius, so as to ensure that all rays encountering the pupil are considered. For example, as illustrated in FIG. 27D, different in-plane shapes (herein shown as a disk-shape or circular profile) may be considered, without limitation, as required.

In some embodiments, phase element 2500 may comprise multiple layers (not shown), each layer having its own refractive index, thus comprising a multiplicity of internal surfaces in addition to the external surfaces 2700 and 2702 (not shown).

Figure 28:
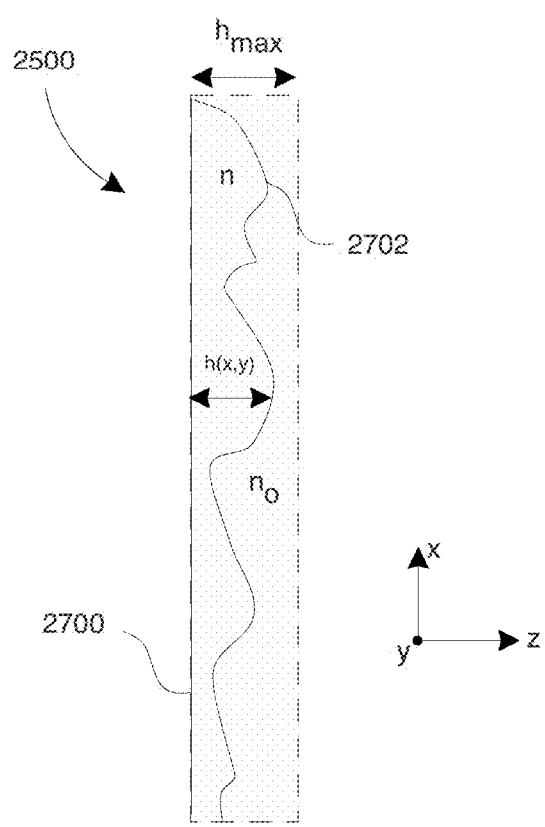
FIG. 28 is a schematic diagram illustrating a side-view of an exemplary phase element comprising a variable profile defined via a height or thickness function, in accordance with one embodiment.

In the methods considered below, as an example only, the embodiment of phase element 2500 considered, will consist of a phase element having a circular profile (as in the diagram of FIG. 27D), but having a flat or plane-like first surface 2700 and a second surface 2702 having a variable shape, depth, height or profile defined via a height or thickness function h(x,y), as illustrated schematically in FIG. 28. In this example, function h(x,y) may thus give the height or depth z-position of second surface 2702 as measured perpendicularly from the z-position of first surface 2700 for all (x,y) values. In this example, phase element 2500 is thus constructed by computing the height or thickness function h(x,y) (in conjunction with a refractive index n) that reproduces the required HOAs (or aberrations in general).

Different methods may be used to derive the correct profile of phase element 2500. In some embodiments, the required aberrational phase shift may be defined using Zernike Polynomials, for example. In other embodiments, the required phase shift may be derived from measurements or the like, for example a lens profile measurement or wave front measurement. The embodiments discussed below will use Zernike polynomials, as an example only, since they are commonly used as a complete set of functions to represent the effect of any optical element or aberration on an incoming wave front. However, other decomposition functions or polynomials may be used, for example and without limitation, Seidel series, Fourier series, Taylor polynomials, elliptical polynomials, etc.

In addition, in some embodiments, small beams may be assumed when sampling the phase element 2500, so that the divergence or convergence due to the presence of the phase element may be minimal. Again, the various embodiments described below will use such an approximation, also as an example only.

Now, with reference to FIGS. 29 to 35, and in accordance with different exemplary embodiments, a method for correcting or compensating for HOAs (or aberrations in general) via a light field display, generally referred to using the numeral 2900, will now be discussed.

Figure 29:
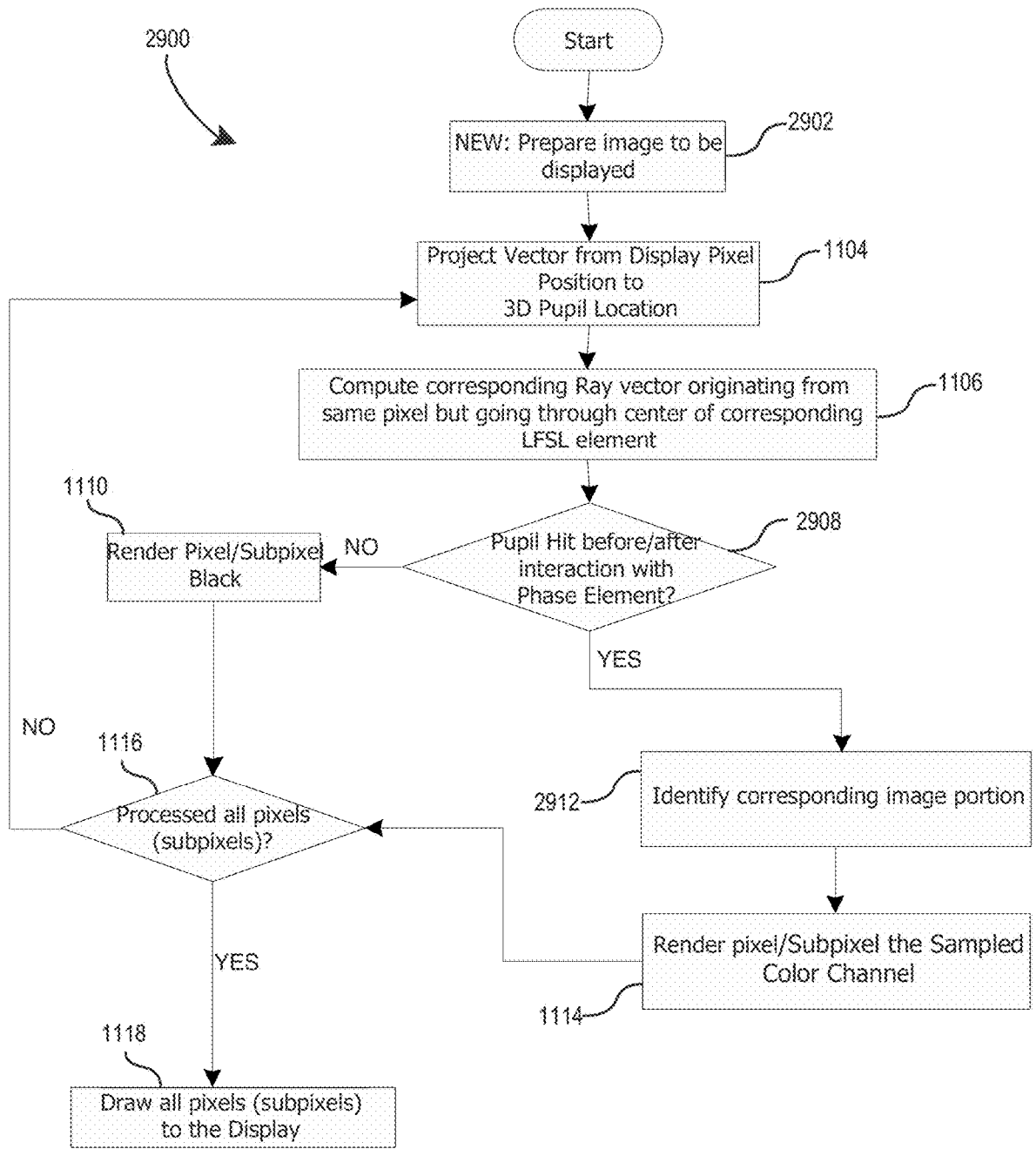
FIG. 29 is a process flow diagram of an illustrative ray-tracing rendering process using the phase element of FIG. 25 and operable to compensate for HOAs, in accordance with one embodiment.

In some embodiments, method 2900 as illustrated in FIG. 29 is an extension of method 1100 discussed above, but now includes the effects of incorporating one or more phase elements 2500 to treat HOAs (or aberrations in general). While some steps are similar as those described above, other steps have been modified or added as required.

Figure 30:
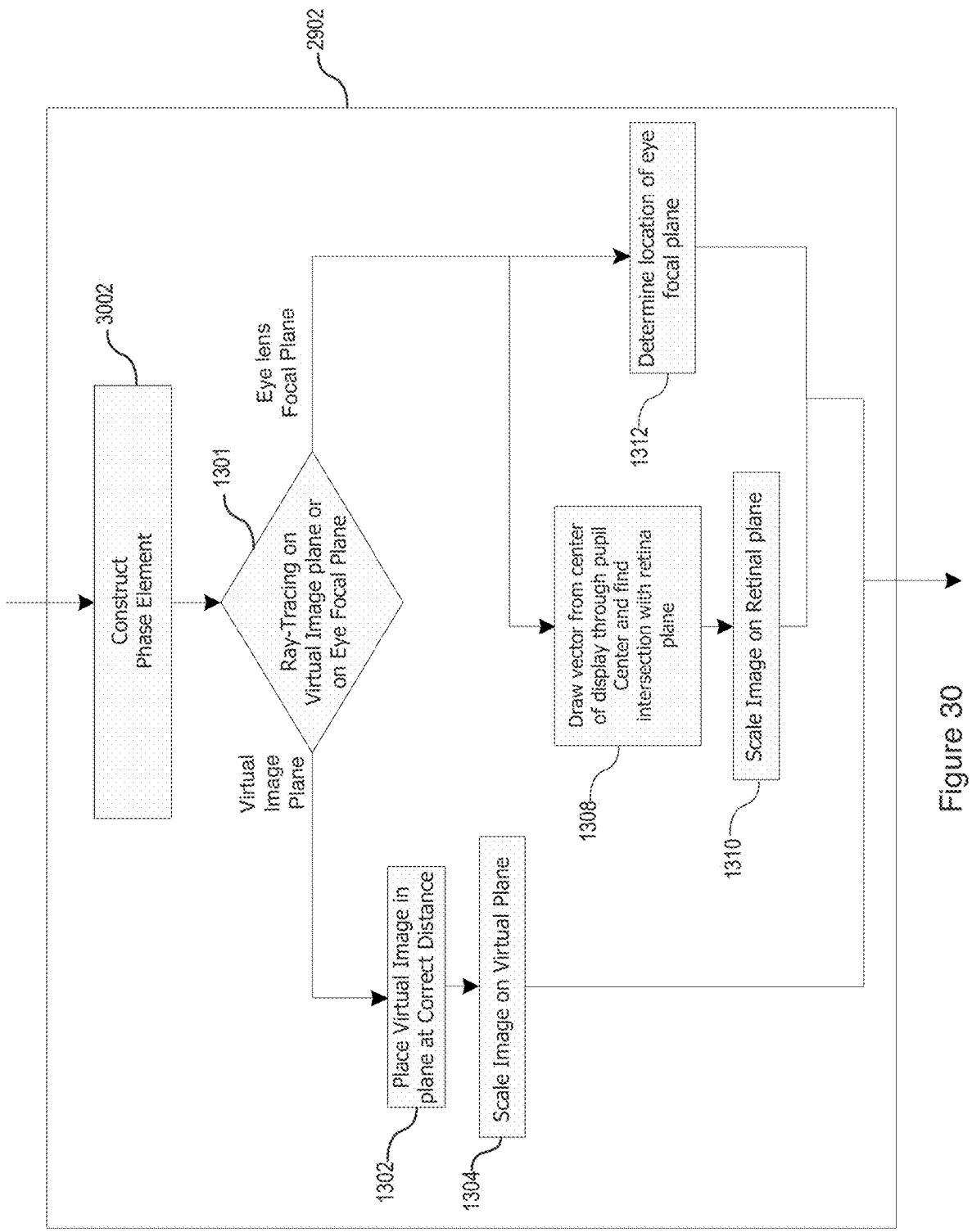
FIG. 30 is process flow diagram illustrating certain process steps of FIG. 29, in accordance with one embodiment.

At step 2902, the image or optotype to be displayed is prepared. This is illustrated in FIG. 30, where, at sub-step 3002, one or more virtual phase elements 2500 are constructed or defined. This includes, in part, defining the required geometry and optical properties of each phase element 2500 so as to reproduce the required aberrational phase shift, as was explained above. Notably, in some embodiments, multiple phase elements 2500 may be used simultaneously, as will be discussed below.

Figure 31A:
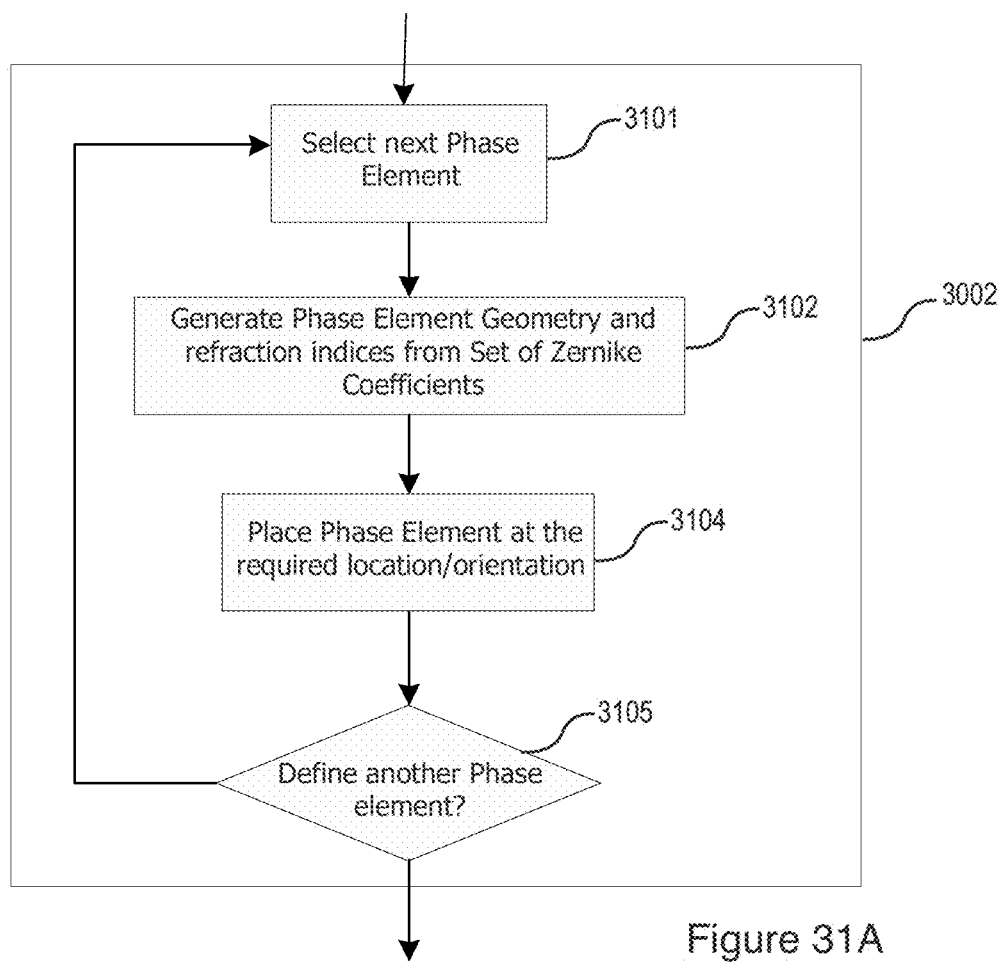
FIGS. 31A and 31B are process flow diagrams illustrating certain process steps of FIG. 30, in accordance with one embodiment.

An example of sub-step 3002 is shown in FIG. 31A. There, an iteration over all the phase element(s) 2500 to be constructed or defined is made starting at sub-step 3101. For each phase element 2500, its geometry and refraction index are computed at sub-step 3102 and its orientation and location at sub-step 3104. At sub-step 3105 the method proceeds back to sub-step 3101 if more phase elements are to be used.

Figure 31B:
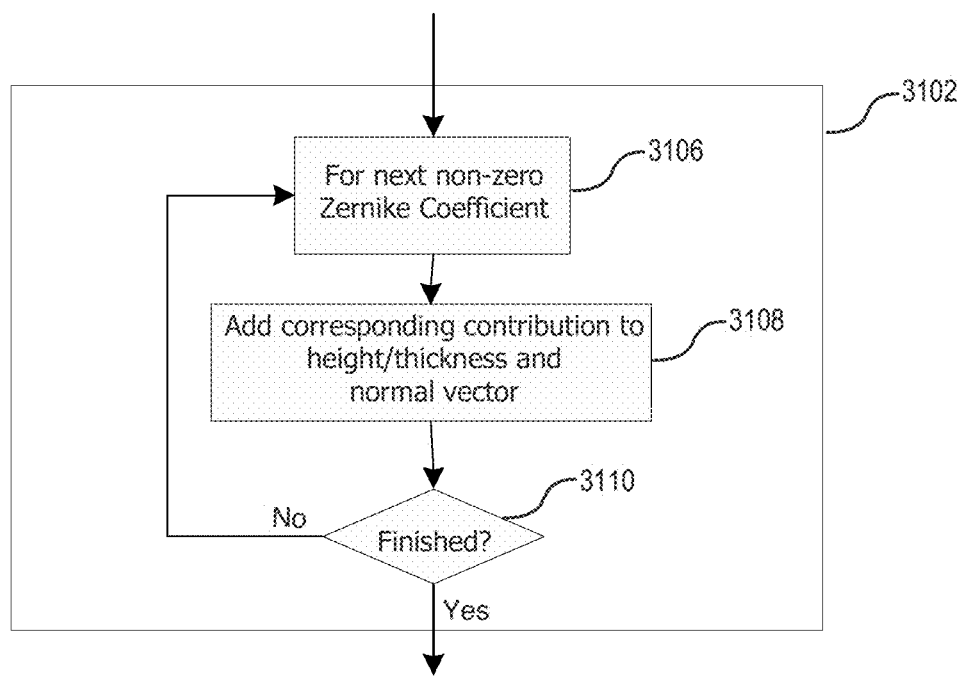

In one exemplary embodiment, and as illustrated in FIG. 31B, a given phase element 2500 is defined or constructed in sub-step 3102 to reproduce a phase shift as defined by a given Zernike polynomial which may be characterized by a corresponding set of Zernike coefficients 1036. In addition, in this embodiment, it is designed so as to comprise a first input surface 2700 (facing the light field display) that is flat and parallel to the (x,y) plane (as an example only) and second output surface 2702 (facing the user) which has a profile or shape that varies as a function of planar position (x,y). In addition, a refractive index 1038 ($n$) of phase element 2500 is also chosen accordingly. The exact value of refractive index 1038 is not meant to reproduce exactly the refractive index of a real optical element (external lens or user's eye), but it is chosen so that, in combination with the height function h(x,y), the phase element 2500 properly or correctly reproduces the chosen HOAs (or aberration in general) evaluated by comparison to diffraction patterns of wavefronts (for example such as those illustrated in FIGS. 32A and 32B).

Notably, if the height or thickness function h(x,y) is known analytically, corresponding analytical expressions for the normal vector functions of the second surface 2702 may also be used. In other embodiments, height function h(x,y) and refractive index/indices may be derived from experimental data or similar, and thus they can be used directly, and it may be required to use numerical derivatives or similar methods to compute the normal vectors. In addition, the data points can be fitted to smooth analytical functions to reduce the numerical errors in calculating the derivatives.

In some embodiments, the pre-computed or measured height or thickness function h(x,y) of phase element 2500 and the associated pre-computed normal vector coordinates may be stored digitally in an array structure or similar. For example, these values may be stored via a texture object or similar, for ease and speed of access. Thus, in some embodiments, different "resolutions" of the texture object may be used, so as to "coarse-grain" the geometry as required by considerations of speed of computation, as will be further discussed below.

In one exemplary embodiment of step 3102, illustrated in FIG. 31B, the HOAs are decomposed or described mathematically using Zernike polynomials ($Z_i$ or $Z_k^j$). These polynomials are used to represent or define deviations or shifts from a desired wave-front. Since a wave-front is a plane of uniform phase, the Zernike phase shift describing the effect of one or more optical aberrations may be written as, for example:

$$\varphi_Z(x, y) = \mathbb{Z}(x, y) = \frac{2\pi}{\lambda_0}\Sigma C_i Z_i(x, y) = \frac{2\pi}{\lambda_0}\Sigma C_{kj} Z_k^j(r, \theta).$$

In some embodiments, as was illustrated in FIGS. 28A and 28B, the spatial dependent height or thickness h(x,y) of phase element 2500, as defined from the location or position of the first interface or surface 2700 with respect to the second surface 2702, may be computed using a corresponding phase shift function, φ(x,y), which represents the effect of HOAs (or aberrations in general) on an incoming wave front, and at least one corresponding refractive index 1038 (n) of phase element 2500. In some embodiments, the phase shift may be constructed on a plane parallel to the lens principal plane using a multiplicity of parallel rays passing through the interior of phase element 2500, again as was illustrated in FIG. 25. To achieve that, both phase element 2500 and the remnant distance to reach the phase-construction plane may be considered.

Thus, as mentioned above, at sub-step 3102 of FIG. 31A, the geometry and refraction index of one phase element 2500 is generated from the input set of Zernike coefficients 1036. For example, in the exemplary embodiment of FIGS. 28A and 28B, a thin element assumption or approximation may be used, so that the phase-change or phase-shift as a function of (x,y) coordinates generated by phase element 2500 may be written as:

$$\varphi(x, y) = \frac{2\pi}{\lambda_0}[nh(x, y) + n_0(h_{max} - h(x, y))]$$

which, excluding the constant phase term, gives a height or thickness as a function of the (x,y) coordinates of:

$$h(x, y) = \frac{\lambda_0}{2\pi} \frac{\varphi(x, y)}{n - n_0}$$

where $n_0$ is the medium refractive index and n is the refractive index 1038. Assuming phase element 2500 is immersed in air (i.e. $n_0$=1), then the (height or thickness) becomes:

$$h(x, y) = \frac{\lambda_0}{2\pi} \frac{\varphi(x, y)}{n - 1}.$$

Thus, for a given phase-shift function φ(x,y), the equation above may be used to derive the corresponding height or thickness function h(x,y) at any point (x,y) of phase element 2500.

In addition, the refraction properties of phase element 2500 may be derived in different ways, as required. For example, and in accordance with one embodiment, the continuity of the tangential wave-vector component may be used to derive ray refraction equations. The position ($x_T, y_T$) of the transmitted ray through a surface is the same as the incident ray ($x_I, y_I$), thus:

$$(x_T, y_T) = (x_I, y_I).$$

A normal of the surface vector ($\overline{N}_S$) and a corresponding incident ray wave-vector ($\overline{K}_I$) define the plane of incidence. This plane can be defined by the normal that is calculated by the cross product:

$$\hat{N}_I = \frac{\overline{K}_I \times \overline{N}_S}{|\overline{K}_I||\overline{N}_S|}.$$

The angle of incidence ($\theta_I$) between the surface normal and the ray wave-vector, is given by:

$$\cos(\theta_I) = \frac{\overline{K}_I \cdot \overline{N}_S}{|\overline{K}_I||\overline{N}_S|},$$

So, in the plane of incidence, Snell's law can be used to calculate the transmitted ray angle ($\theta_T$):

$$n_I \sin(\theta_I) = n_T \sin(\theta_T)$$

where $n_I$, $n_T$, are the refractive indices in the incidence and transmission media, respectively.

In addition, the incident wave vector can be decomposed in terms of the surface normal vector and a surface tangential vector ($\overline{N}_t$):

$$a_{tI}\overline{N}_t = \overline{K}_I - \cos(\theta_I)|\overline{K}_I|\frac{\overline{N}_S}{|\overline{N}_S|}.$$

The transmitted ray direction-vector ($\overline{K}_T$) may be calculated by considering that the continuity of the tangential component of the wave vector and the change in its magnitude. Again, representing the transmitted component as normal and tangential components, in the plane of incidence:

$$\overline{K}_T = \frac{\overline{N}_S}{|\overline{N}_S|}\cos(\theta_T)|\overline{K}_I|\frac{n_T}{n_I} + \overline{K}_I - \cos(\theta_I)|\overline{K}_I|\frac{\overline{N}_S}{|\overline{N}_S|}.$$

In some embodiments, as in this example wherein the function h(x,y) is available analytically, corresponding analytical expressions for the normal unit vectors on the surface at every location h(x,y) may be derived using the gradient of the surface. Assuming the height or thickness is in the z direction only, for a function of the form:

$$S(x,y,z) = 0,$$

the normal unit vectors to the surface are given by:

$$\hat{n} = \frac{\langle S_x, S_y, S_z \rangle}{|\langle S_x, S_y, S_z \rangle|}$$

-continued for $(n-n_0)z - \frac{\lambda_0}{2\pi}\varphi(x,y) = 0$, then:

$$\hat{n} = \frac{\overline{N}_s}{|\overline{N}_s|} = \frac{\left[-\frac{\lambda_0 \partial \varphi}{2\pi \partial x'} - \frac{\lambda_0 \partial \varphi}{2\pi \partial y'}(n-n_0)\right]}{\sqrt{\left(\frac{\lambda_0 \partial \varphi}{2\pi \partial x}\right)^2 + \left(\frac{\lambda_0 \partial \varphi}{2\pi \partial y}\right)^2 + (n-n_0)^2}},$$

where $n_0$ is the medium refractive index and n is the phase element refractive index 1038. In air, this gives:

$$\hat{n}(x,y) = \frac{\overline{N}_s}{|\overline{N}_s|} = \frac{\left[-\frac{\lambda_0 \partial \varphi}{2\pi \partial x'} - \frac{\lambda_0 \partial \varphi}{2\pi \partial y'}(n-1)\right]}{\sqrt{\left(\frac{\lambda_0 \partial \varphi}{2\pi \partial x}\right)^2 + \left(\frac{\lambda_0 \partial \varphi}{2\pi \partial y}\right)^2 + (n-1)^2}}.$$

In some embodiments, a variety of optimizations may be employed. As mentioned above, analytical forms of the derivatives may be used. In addition, a high value of refractive index 1038 may also be used to minimize the thickness of phase element 2500 (although precautions must be taken so as to avoid the total internal reflection regime).

In some embodiments, if the computed height or thickness function h(x,y) results in negative values and a non-thin phase element is considered, a constant height or thickness value may be subtracted before computing ray propagation inside the element. For example:

$$h(x,y) = h(x,y) - \min(h(x,y)).$$

where min(h(x,y)) is the minimum value of function h(x,y).

We present herein an example of how Zernike polynomials and their corresponding Zernike coefficients 1036 may be used to model HOAs.

In some embodiments, a thin lens assumption may be used for phase element 2500. For example, considering a thin element with a first flat incident surface 2700 is perpendicular to z-axis, then:

$$S(x,y,z) = z - z_{0=0}$$

$$\hat{n} = \langle 0,0,1 \rangle$$

and the second surface 2702, herein modelled as an ideal thin lensing surface may (with no approximation) may be given by:

$$\phi(x,y) = \frac{2\pi}{\lambda_0}\left[f - \sqrt{x^2+y^2+f^2}\right]$$

$$= \frac{2\pi}{\lambda_0}f\left(1 - \sqrt{1 + \frac{x^2+y^2}{f^2}}\right)$$

$$= \frac{2\pi}{\lambda_0}\frac{1 - \sqrt{1+A^2(x^2+y^2)}}{A}$$

where f is the focal length of phase element 2500; which, for the paraxial limit gives:

$$\phi(x,y) \approx -\frac{2\pi}{\lambda_0}\frac{x^2+y^2}{2f} = -\frac{2\pi}{\lambda_0}A\frac{x^2+y^2}{2}$$

$$S(x,y,z) = (n-1)z - f + \sqrt{x^2+y^2+f^2} = 0$$

-continued $$\hat{n} = \frac{\left\langle \frac{x}{\sqrt{x^2+y^2+f^2}}, \frac{y}{\sqrt{x^2+y^2+f^2}}, (n-1)\right\rangle}{\sqrt{\frac{x^2+y^2}{x^2+y^2+f^2} + (n-1)^2}}.$$

In the case of a thin lens in the paraxial approximation, transfer matrix model may be used. In this example, the spatial coordinates do not change, on the other hand the wave-vector angle is given by:

$$\vec{\theta}_T = \left(\frac{-x_I}{f} + \theta_{xI}\right)\hat{\theta}_x + \left(\frac{-y_I}{f} + \theta_{yI}\right)\hat{\theta}_y$$

For: $\overline{K}_I = a_{ix}\hat{x} + a_{iy}\hat{y} + a_{iz}\hat{z}$ $$\theta_{Ix} = \operatorname{asin}\left(\frac{a_{ix}}{\sqrt{a_{ix}^2+a_{iz}^2}}\right) \approx \frac{a_{ix}}{a_{iz}}$$

The transmitted directional vector $$\overline{K}_T = a_{Tx}\hat{x} + a_{Ty}\hat{y} + a_{Tz}\hat{z}$$

$$\theta_{Tx} = \operatorname{asin}\left(\frac{a_{Tx}}{\sqrt{a_{Tx}^2+a_{Tz}^2}}\right) \approx \frac{a_{Tx}}{a_{Tz}} = \theta_{xI} - \frac{x_I}{f} = \frac{a_{ix}}{a_{iz}} - \frac{x_I}{f}$$

$$a_{Tx} = \left(\frac{a_{ix}}{a_{iz}} - \frac{x_I}{f}\right)a_{Tz}$$

$$a_{Ty} = \left(\frac{a_{iy}}{a_{iz}} - \frac{y_I}{f}\right)a_{Tz}$$

$$\sqrt{a_{Tx}^2 + a_{Ty}^2 + a_{Tz}^2} = |\overline{K}_T|$$

$$a_{Tz}\sqrt{\left(\frac{a_{ix}}{a_{iz}} - \frac{x_I}{f}\right)^2 + \left(\frac{a_{iy}}{a_{iz}} - \frac{y_I}{f}\right)^2 + 1} = |\overline{K}_T|, \text{ so that}$$

$$a_{Tz} = \frac{|\overline{K}_T|}{\sqrt{\left(\frac{a_{ix}}{a_{iz}} - \frac{x_I}{f}\right)^2 + \left(\frac{a_{iy}}{a_{iz}} - \frac{y_I}{f}\right)^2 + 1}};$$

$$a_{Ty} = \frac{|\overline{K}_T|\left(\frac{a_{iy}}{a_{iz}} - \frac{y_I}{f}\right)}{\sqrt{\left(\frac{a_{ix}}{a_{iz}} - \frac{x_I}{f}\right)^2 + \left(\frac{a_{iy}}{a_{iz}} - \frac{y_I}{f}\right)^2 + 1}};$$

$$a_{Tx} = \frac{|\overline{K}_T|\left(\frac{a_{ix}}{a_{iz}} - \frac{x_I}{f}\right)}{\sqrt{\left(\frac{a_{ix}}{a_{iz}} - \frac{x_I}{f}\right)^2 + \left(\frac{a_{iy}}{a_{iz}} - \frac{y_I}{f}\right)^2 + 1}}.$$

More generally, as discussed above, any phase shift $\varphi(x,y)$ may be represented via a Zernike polynomial in the form of:

$$\varphi(x,y) = \mathbb{Z}(x,y) = \frac{2\pi}{\lambda_0}\sum C_i Z_i(x,y)$$

and where the normal vectors to the non-flat surface of the corresponding phase element, in air, are given by:

$$\hat{n} = \frac{\left\langle -\sum C_i \frac{\partial Z_i(x,y)}{\partial x}, -\sum C_i \frac{\partial Z_i(x,y)}{\partial y}, (n-1) \right\rangle}{\sqrt{\left(\sum C_i \frac{\partial Z_i(x,y)}{\partial x}\right)^2 + \left(\sum C_i \frac{\partial Z_i(x,y)}{\partial y}\right)^2 + (n-1)^2}}.$$

Thus, for a given set of Zernike coefficients and their corresponding Zernike function, the corresponding height or thickness function $h(x,y)$ and a corresponding set of normal vector functions $\hat{n}(x,y)$ for the second surface may be computed.

series of plots illustrating the different phase element intensity profiles for refracted rays through a phase element and corresponding profiles for diffracted phase fronts for different Zernike coefficients (numbered via the OSA/ANSI standard indices). These correspond to a phase element in air ($n_o=1$) having a refractive index $n=100$, further assuming that the phase front focal length of 100 mm and a distance between the phase element and the chosen image plane of 1 m.

More generally, in the table below is an exemplary list of Zernike functions and their partial derivatives for different HOAs. Therein the variable r is the polar radial coordinates normalized to the pupil radius ($R_P$) and $\theta$ is the polar angular coordinate and z is the corresponding contribution to the height or thickness $h(x,y)$.

| Aberration | OSA ANSI Index (i) | Noll Index | Radial Index (k) | Azimuthal Index (j) | Z | $\frac{\partial Z}{\partial x}$ | $\frac{\partial Z}{\partial y}$ |
|---|---|---|---|---|---|---|---|
| Piston | 0 | 1 | 0 | 0 | 1 | 0 | 0 |
| Y-Tilt | 1 | 3 | 1 | −1 | $2r \sin(\theta) = 2y/R_p$ | 0 | $2/R_p$ |
| X-Tilt | 2 | 2 | 1 | +1 | $2r \cos(\theta) = 2x/R_p$ | $2/R_p$ | 0 |
| Y-Astigmatism | 3 | 5 | 2 | −2 | $\sqrt{6}r^2 \sin(2\theta) = 2\sqrt{6} xy/R_p^2$ | $2\sqrt{6}\, y/R_p^2$ | $2\sqrt{6}\, x/R_p^2$ |
| Defocus | 4 | 4 | 2 | 0 | $\sqrt{3}(2r^2 - 1) = \sqrt{3}(2(x^2+y^2)/R_p^2 - 1)$ | $4\sqrt{3}\, x/R_p^2$ | $4\sqrt{3}\, y/R_p^2$ |
| X-Astigmatism | 5 | 6 | 2 | +2 | $\sqrt{6}r^2 \cos(2\theta) = \sqrt{6}(x^2-y^2)/R_p^2$ | $2\sqrt{6}\, x/R_p^2$ | $-2\sqrt{6}\, y/R_p^2$ |
| Y-Trefoil | 6 | 9 | 3 | −3 | $\sqrt{8}r^3 \sin(3\theta) = \sqrt{8}(-y^3 + 3x^2y)/R_p^3$ | $6\sqrt{8}\, xy = 6\sqrt{8}\, xy/R_p^3$ | $6\sqrt{2}(x^2 - y^2)x/\sqrt{x^2} = \sqrt{8}(3x^2 - 3y^2)/R_p^3$ |
| Y-Coma | 7 | 7 | 3 | −1 | $\sqrt{8}(3r^3 - 2r)\sin(\theta) = \sqrt{8}(3x^2y/R_p^3 + 3y^3/R_p^3 - 2y/R_p)$ | $6\sqrt{6}\, xy/R_p^3$ | $\sqrt{8}\left(3\frac{x^2}{R_p^3} + 9\frac{y^2}{R_p^3} - \frac{2}{R_p}\right)$ |
| X-Coma | 8 | 8 | 3 | +1 | $\sqrt{8}(3r^3 - 2r)\cos(\theta) = \sqrt{8}(3x^3/R_p^3 + 3y^2x/R_p^3 - 2x/R_p)$ | $\sqrt{8}\left(3\frac{y^2}{R_p^3} + 9\frac{x^2}{R_p^3} - \frac{2}{R_p}\right)$ | $6\sqrt{8}\, \frac{xy}{R_p^3}$ |
| X-Trefoil | 9 | 10 | 3 | +3 | $\sqrt{8}r^3 \cos(3\theta) = \sqrt{8}(x^3/R_p^3 - 3y^2x/R_p^3)$ | $\sqrt{8}\, \frac{(3x^2 - 3y^2)}{R_p^3}$ | $-6\sqrt{8}\, \frac{yx}{R_p^3}$ |
| Y-Quadrafoil | 10 | 15 | 4 | −4 | $\sqrt{10}r^4 \sin(4\theta) = 4\sqrt{10}yx(x^2 - y^2)/R_p^4$ | $4\sqrt{10}\, \frac{(3x^2y - y^3)}{R_p^4}$ | $4\sqrt{10}\, \frac{(x^3 - 3xy^2)}{R_p^4}$ |
| Y-Secondary Astigmtism | 11 | 13 | 4 | −2 | $\sqrt{10}(4r^4 - 3r^2)\sin(2\theta) = \sqrt{10}(8x^3y/R_p^4 + 8y^3x/R_p^4 - 6xy/R_p^2)$ | $2\sqrt{10}(4y^3/R_p^4 + 12yx^2/R_p^4 - 3y/R_p^2)$ | $2\sqrt{10}(4x^3/R_p^4 + 12xy^2/R_p^4 - 3x/R_p^2)$ |
| Primary Spherical | 12 | 11 | 4 | 0 | $\sqrt{5}(6r^4 - 6r^2 + 1) = \sqrt{5}(6(x^4 + y^4 + 2x^2y^2)/R_p^4 - 6x^2/R_p^2 - 6y^2/R_p^2 + 1)$ | $\sqrt{5}(24x^3/R_p^4 + 24y^2x/R_p^4 - 12x/R_p^2)$ | $\sqrt{5}(24y^3/R_p^4 + 24x^2y/R_p^4 - 12y/R_p^2)$ |
| X-Secondary Astigmatism | 13 | 12 | 4 | +2 | $\sqrt{10}(4r^4 - 3r^2)\cos(2\theta) = \sqrt{10}[(4x^4 - 4y^4)/R_p^4 - (3x^2 - 3y^2)/R_p^2]$ | $\sqrt{10}\left(16\frac{x^3}{R_p^4} - 6\frac{x}{R_p^2}\right)$ | $\sqrt{10}\left(6\frac{y}{R_p^2} - 16\frac{y^3}{R_p^4}\right)$ |
| X-Quadrafoil | 14 | 14 | 4 | +4 | $\sqrt{10}r^4 \cos(4\theta) = \sqrt{10}(x^4 + y^4 - 6y^2/R_p^4)$ | $\sqrt{10}\left(4\frac{x^3}{R_p^4} - 12\frac{xy^2}{R_p^4}\right)$ | $\sqrt{10}\left(4\frac{y^3}{R_p^4} - 12\frac{yx^2}{R_p^4}\right)$ |

Figure 32A:
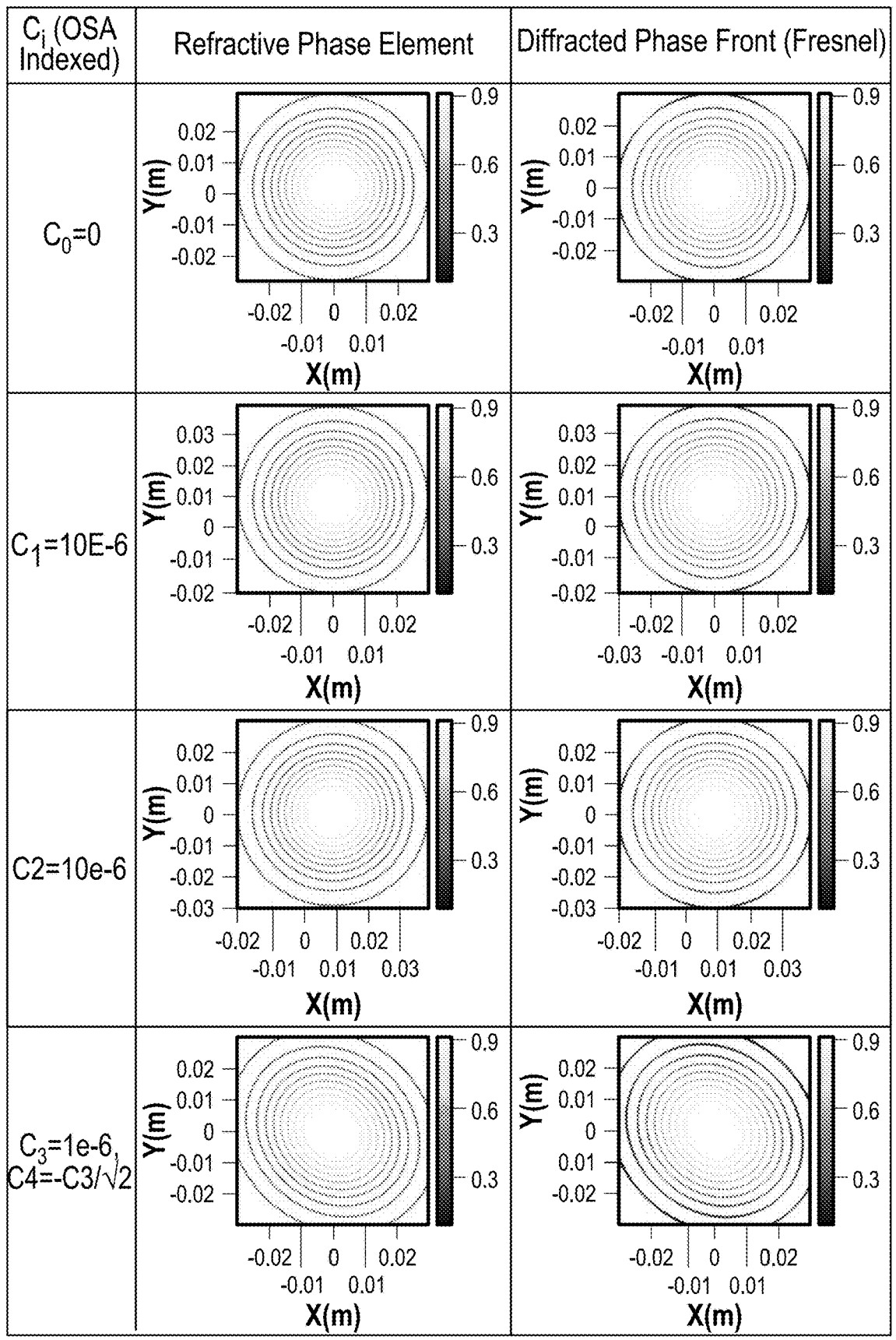
FIGS. 32A and 32B are plots of different profiles comparison of normally incident beam for raytracing through phase elements of FIG. 25 compared to diffraction with the corresponding aberration phase added to the wave front pre-diffraction. Normalized intensity profiles at the detector/image plane are shown, in accordance with one embodiment.
Figure 32A:
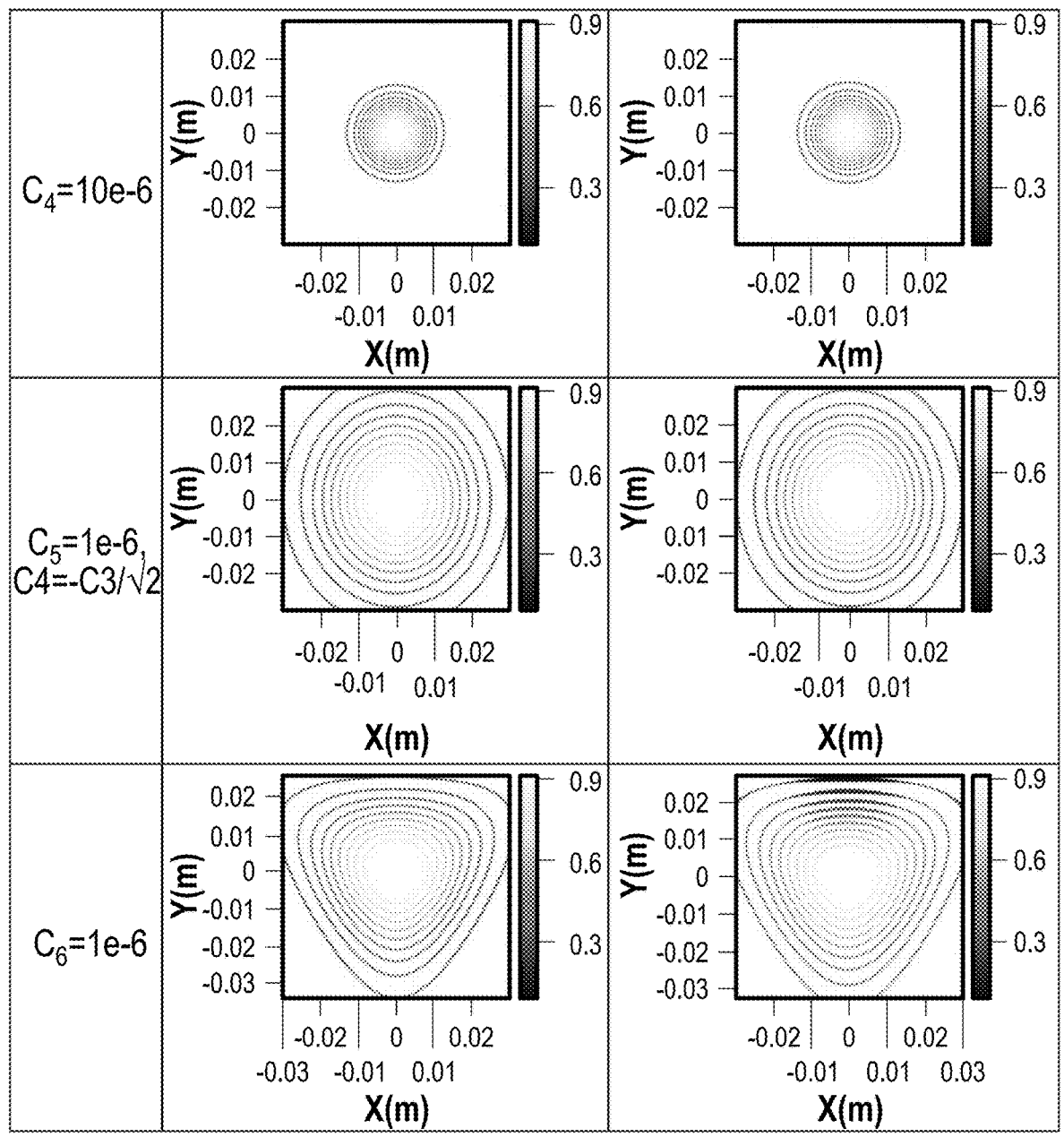
Figure 32B:
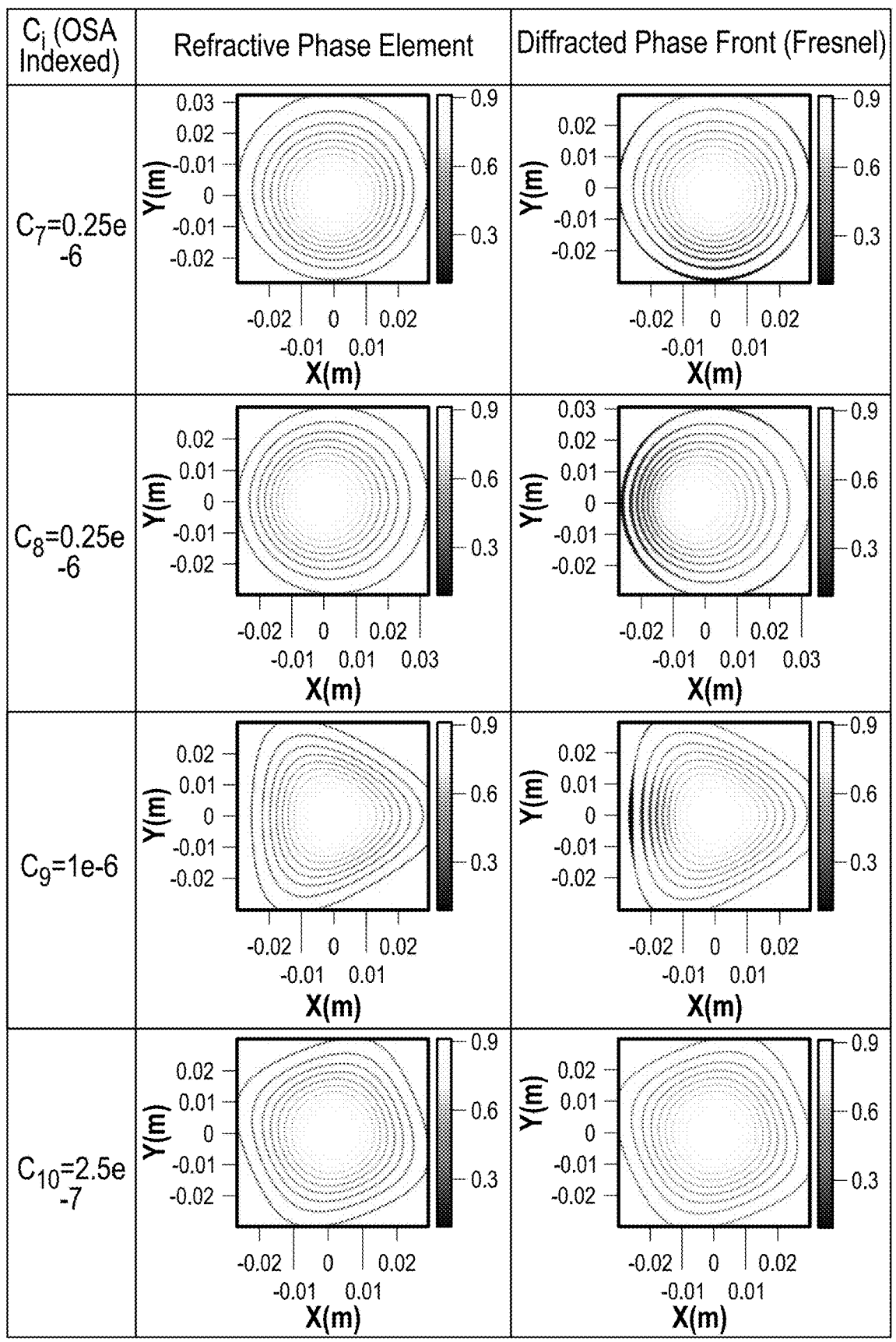
Figure 32B:
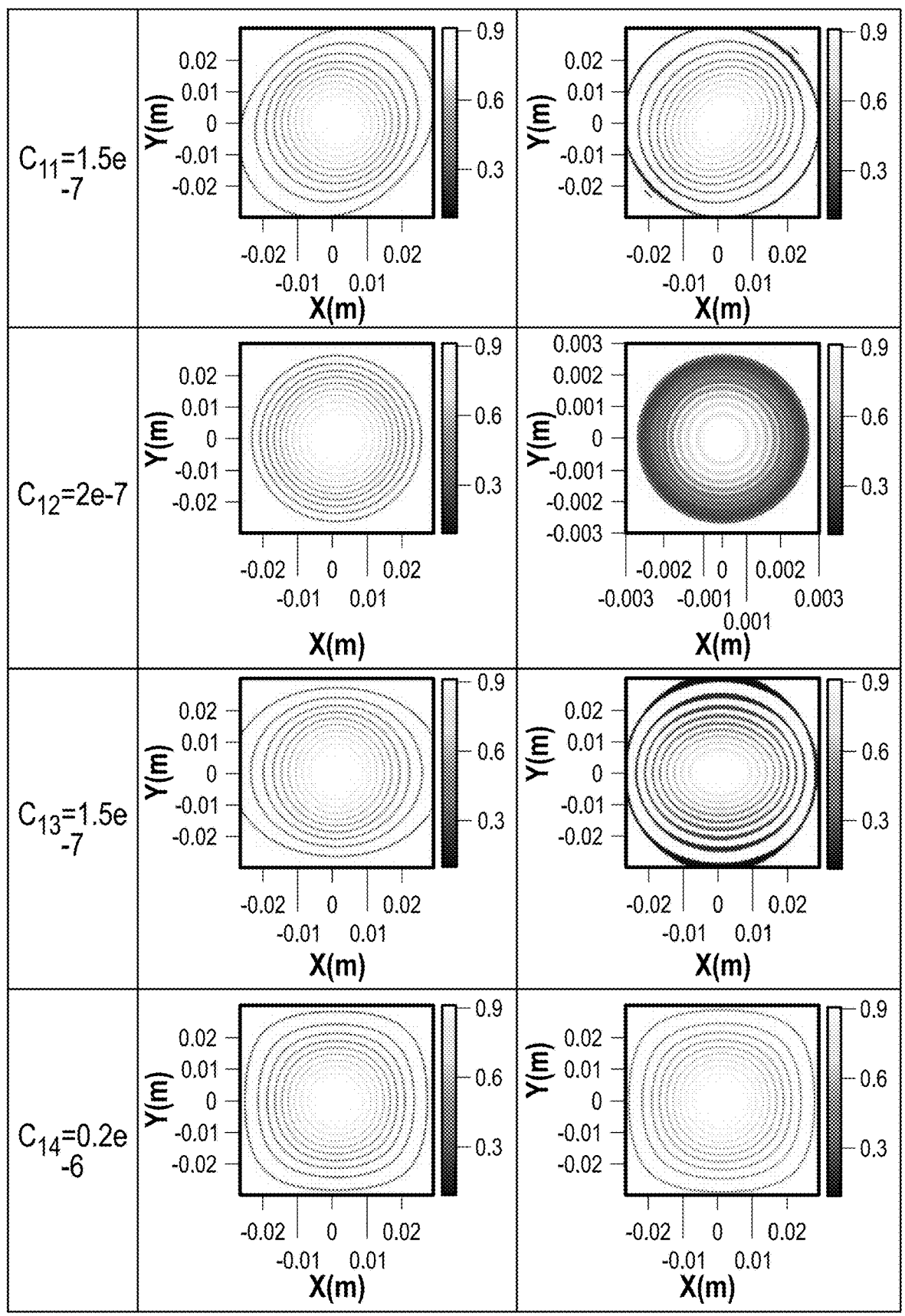

In some embodiments, the refractive index and shape of phase element 2500 may be obtained by trial and error to match, for example, a refracted beam produced by phase element 2500 with a diffraction profile or by profiling a real optical element. For example, FIGS. 32A and 32B shows a In addition, Zernike coefficients may be derived in different ways, as is well known in the art. For example, an astigmatism prescription may be converted to a Zernike phase shift function and vice-versa. The corresponding coefficients of concern here are: S: the spherical dioptric power 1026, C: cylindrical dioptric power 1030, ϑ the cylinder axis angle 1032, and RP: the pupil radius. In this example, the relation to the relevant Zernike coefficients 1036 may be given through the following relations:

Plus-Cylindrical Notation:

$$S = -\frac{4\sqrt{3}\,c_2^0}{R_P^2} - \frac{2\sqrt{6}\,\sqrt{(c_2^{-2})^2 + (c_2^2)^2}}{R_P^2},$$

$$C = -\frac{4\sqrt{6}\,\sqrt{(c_2^{-2})^2 + (c_2^2)^2}}{R_P^2},$$

$$\vartheta = \frac{1}{2}\tan^{-1}\left(\frac{c_2^{-2}}{c_2^2}\right)$$

Minus-Cylindrical Notation:

$$S = -\frac{4\sqrt{3}\,c_2^0}{R_P^2} + \frac{2\sqrt{6}\,\sqrt{(c_2^{-2})^2 + (c_2^2)^2}}{R_P^2},$$

$$C = -\frac{4\sqrt{6}\,\sqrt{(c_2^{-2})^2 + (c_2^2)^2}}{R_P^2},$$

$$\vartheta = \frac{1}{2}\tan^{-1}\left(\frac{c_2^{-2}}{c_2^2}\right) + \frac{\pi}{2}$$

Zernike Coefficients for Plus and Minus Cases:

$$c_2^{-2} = \frac{R_P^2 C \sin(2\vartheta)}{4\sqrt{6}}$$

$$c_2^0 = \frac{-R_P^2(S + C/2)}{4\sqrt{3}}$$

$$c_2^2 = \frac{R_P^2 C \cos(2\vartheta)}{4\sqrt{6}}.$$

Thus, for example, considering an exemplary astigmatism prescription (no spherical dioptric power, cylindrical dioptric power of 2 and cylinder axis of 30°), an exemplary pupil radius of 2.5 mm and a refractive index of the phase element is taken to be equal to 1.55, an exemplary height profile function h(x,y) will be derived below.

In this example, the corresponding Zernike coefficients are given by:

$$c_2^{-2} = \frac{R_P^2 C \sin(2\vartheta)}{4\sqrt{6}} = 0.17678 R_P^2$$

$$c_2^0 = \frac{-R_P^2(S + C/2)}{4\sqrt{3}} = -0.14434 R_P^2$$

$$c_2^2 = \frac{R_P^2 C \cos(2\vartheta)}{4\sqrt{6}} = 0.10206 R_P^2.$$

The corresponding normal vector function for the second surface is given by:

$$\hat{n}(x, y) = \frac{\left\langle -\sum C_i \frac{\partial Z_i(x,y)}{\partial x}, -\sum C_i \frac{\partial Z_i(x,y)}{\partial y}, (n-1)\right\rangle}{\sqrt{\left(\sum C_i \frac{\partial Z_i(x,y)}{\partial x}\right)^2 + \left(\sum C_i \frac{\partial Z_i(x,y)}{\partial y}\right)^2 + (n-1)^2}};$$

$$\hat{n}(x, y) = \frac{\langle -(0.86604y - 0.50003x), -(0.86604x - 1.5y), 0.55\rangle}{(0.86604y - 0.50003x)^2 + (0.86604x - 1.5y)^2 + (0.55)^2}.$$

The corresponding height or thickness function h(x,y) is given by:

$$\varphi(x, y) = \mathbb{Z}(x, y) = \frac{2\pi}{\lambda_0}\sum C_i Z_i(x, y);$$

$$= \frac{2\pi}{\lambda_0}\left(0.86604xy - 0.50001(x^2 + y^2) + 0.25R_P^2 + 0.24999(x^2 - y^2)\right);$$

$$= \frac{2\pi}{\lambda_0}\left(0.86604xy - 0.25002x^2 - 0.75y^2 + 0.25R_P^2\right);$$

and thus:

$$h(x, y) = \frac{\lambda_0}{2\pi}\frac{\varphi(x, y)}{n - n_0} = \left(1.5746xy - 0.45458x^2 - 1.3636y^2 + 0.25R_P^2\right).$$

Figure 33A:
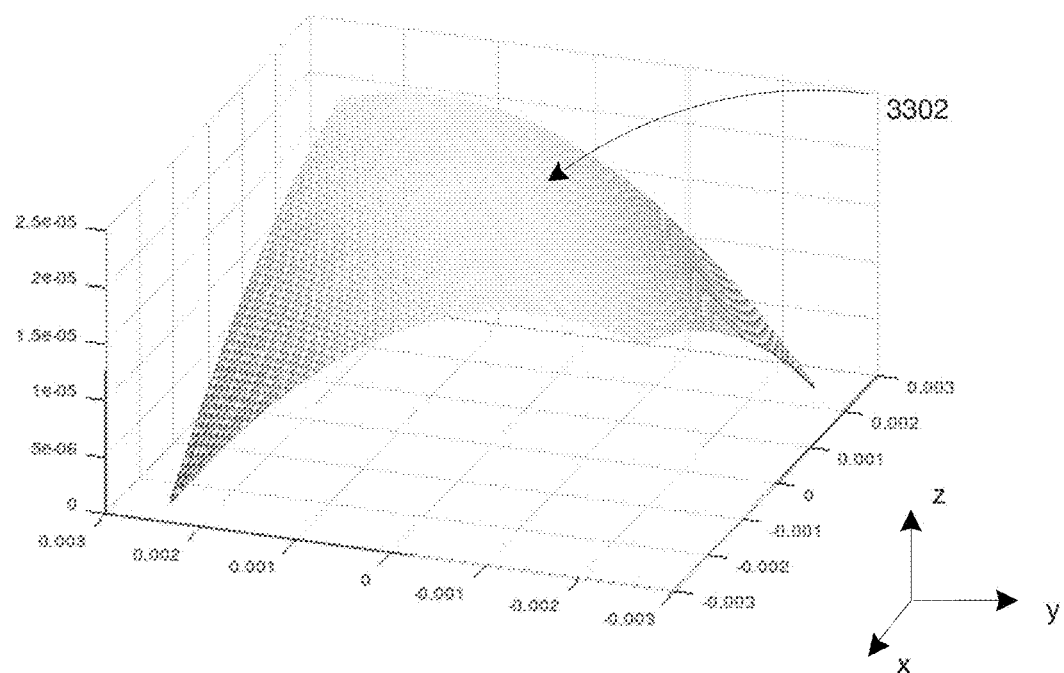
FIGS. 33A and 33B are exemplary plots of a height or thickness function for a phase element simulating astigmatism, in accordance with one embodiment.
Figure 33B:
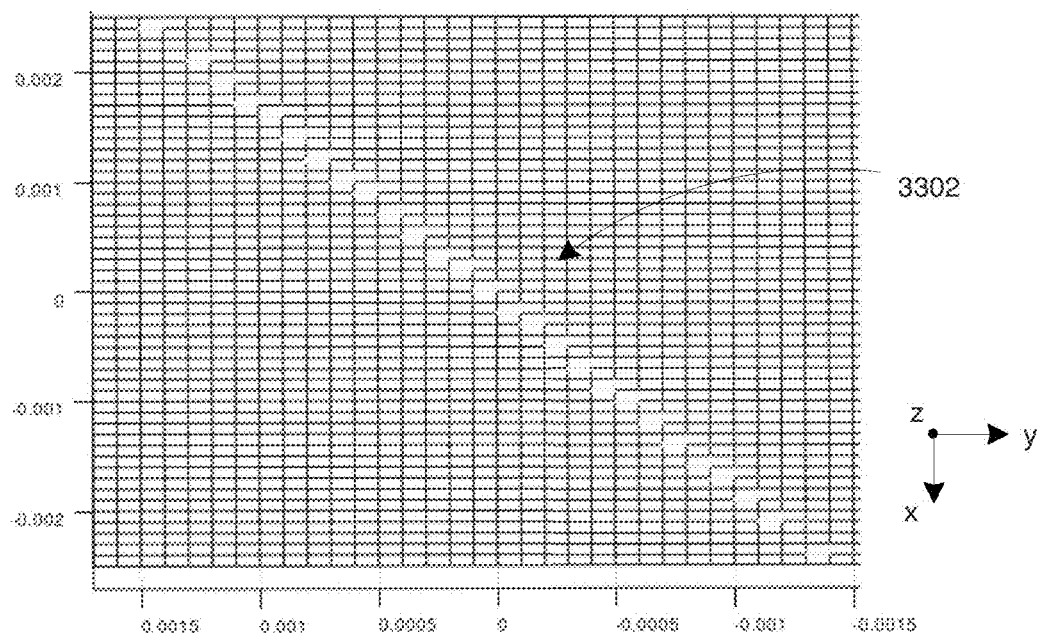

As an example, FIGS. 33A and 33B show plots of the resulting height function h(x,y) computed above (in meters).

Thus, going back to FIG. 31B, to build or construct functions h(x,y) and the associated normal vector functions, starting at sub-step 3106, for each coefficient in Zernike coefficient(s) 1036, at sub-step 3108 the corresponding contribution to the height or thickness function (and normal vector functions) for this Zernike term (coefficient and function) is added, as was done in the example above. This is done until all non-zero Zernike coefficients 1036 have been iterated upon at step 3110.

Going back to FIG. 31A, once the geometry or shape of a phase element 2500 is known, at sub-step 3104, it is "virtually" positioned at the correct location and with the correct orientation. In the examples given herein, first surface 2700 of phase element 2500 is always considered to be parallel to the (x,y) plane, but more general orientations may be considered. Computations with non-parallel surfaces may take into account the required rotational and translational transformations as necessary.

In addition, as mentioned above, phase element may be located at a given distance from the user's eye (so to model a real external lens) or it may be located (via the position of the first surface 2700) at pupil plane 1406 (to model an eye aberration).

Going back to FIG. 30, the rest of sub-step 3002 continues as discussed above in the context of FIG. 13 (i.e. sub-steps 1301 to 1312), again depending on whether ray-tracing is done using the virtual image plane or the retinal plane.

Going back to FIG. 29, the method proceeds with steps 1104 and 1106 as explained above for method 1100. However, at this point, ray 1414 (going through center location 1410 of the corresponding optical unit and originating from pixel location 1402) will encounter and be refracted by a phase element 2500, either before or after encountering pupil plane 1406.

Figure 35:
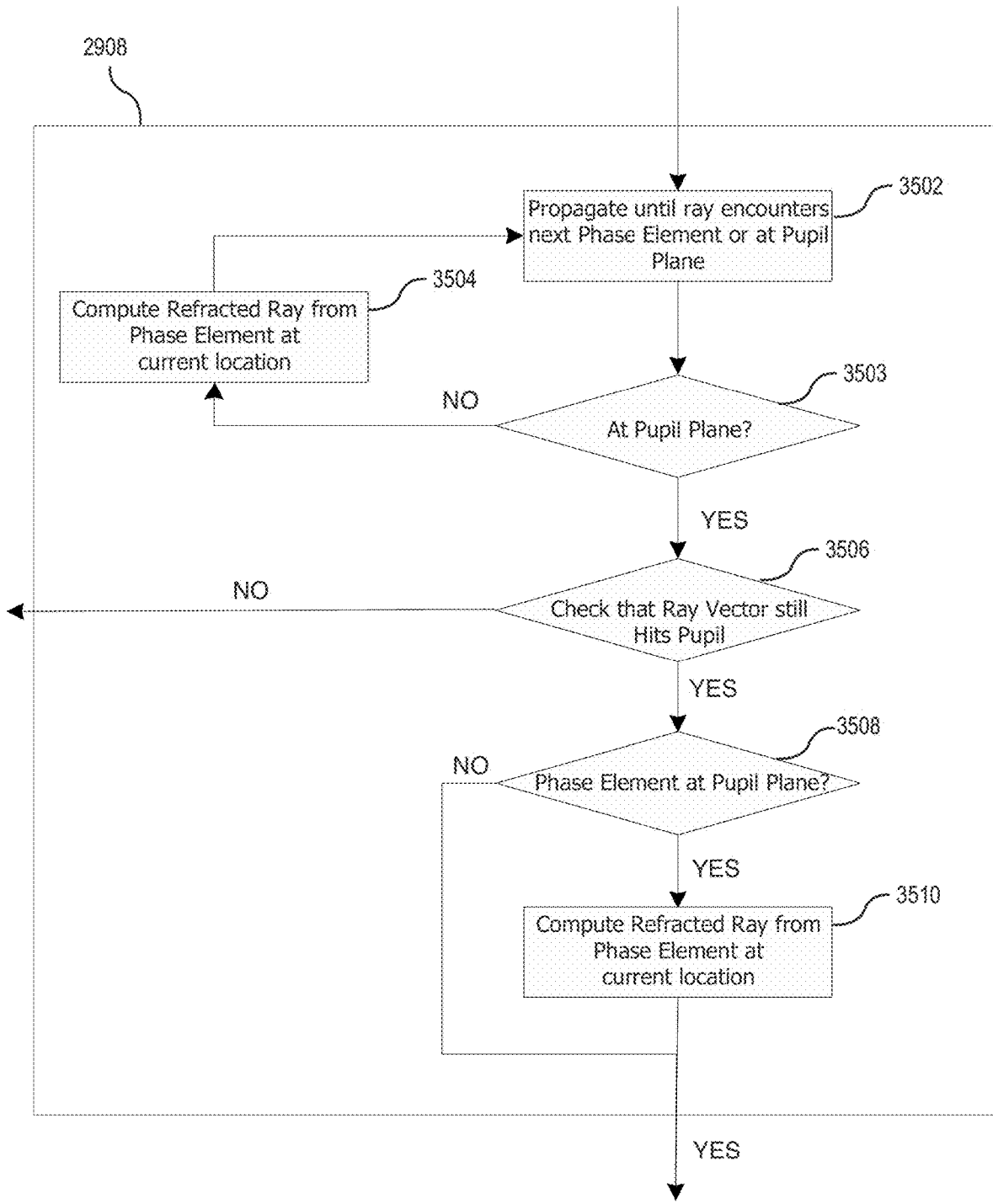
FIG. 35 is a process flow diagram illustrating certain process steps of FIG. 29, in accordance with one embodiment.
Figure 44:
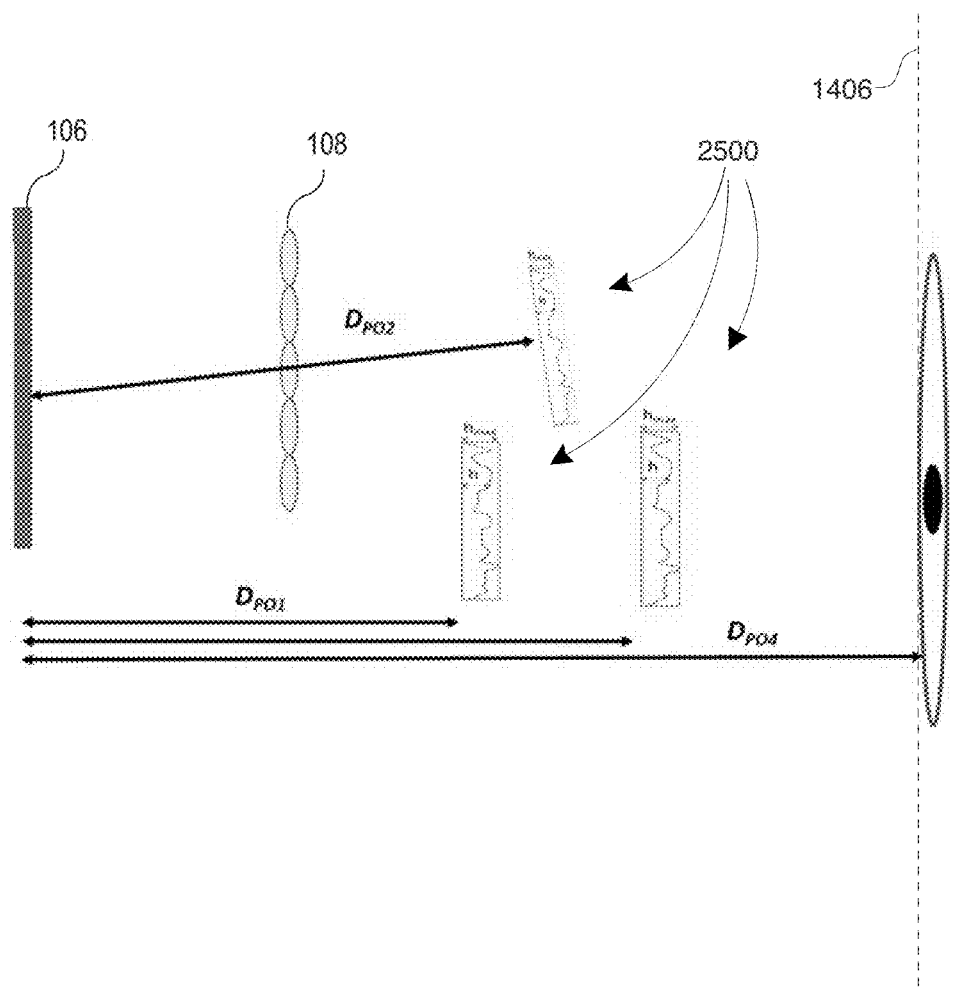
FIG. 44 is a schematic diagram illustrating the use of multiple phase elements simultaneously, in accordance with one embodiment.

Thus, step 2908, as illustrated in FIG. 35, is where rays are propagated and interacted with each phase element 2500. Notably, in this embodiment, more than one phase element 2500 may be used simultaneously, as illustrated schematically in FIG. 44. There, as an example, we see three different phase element 2500 located and oriented differently between the pixel display 106 and LFSL 108 on one side, and the pupil plane 1406 on the other side. These phase elements 2500 may or may not have the same optical properties, as required. In addition, this exemplary embodiment of step 2908 further includes the possibility of having a phase element 2500 at the pupil plane itself, so as to model an aberrated eye, or direct compensation therefor.

Going back to FIG. 35, at sub-step 3502, starting from optical element center location 1410, ray 1414 is propagated in a straight line towards the eye until it either encounters an element 2500 in its path (via first surface 2700), or until it reaches the pupil plane 1406.

At sub-step 3503, a check is made to see if the ray as reached the pupil plane. If not, then it has encountered a first surface 2700 of a phase element 2500 in its path. At sub-step 3504 the refracted ray obtained from this phase element 2500 is computed.

Figure 34:
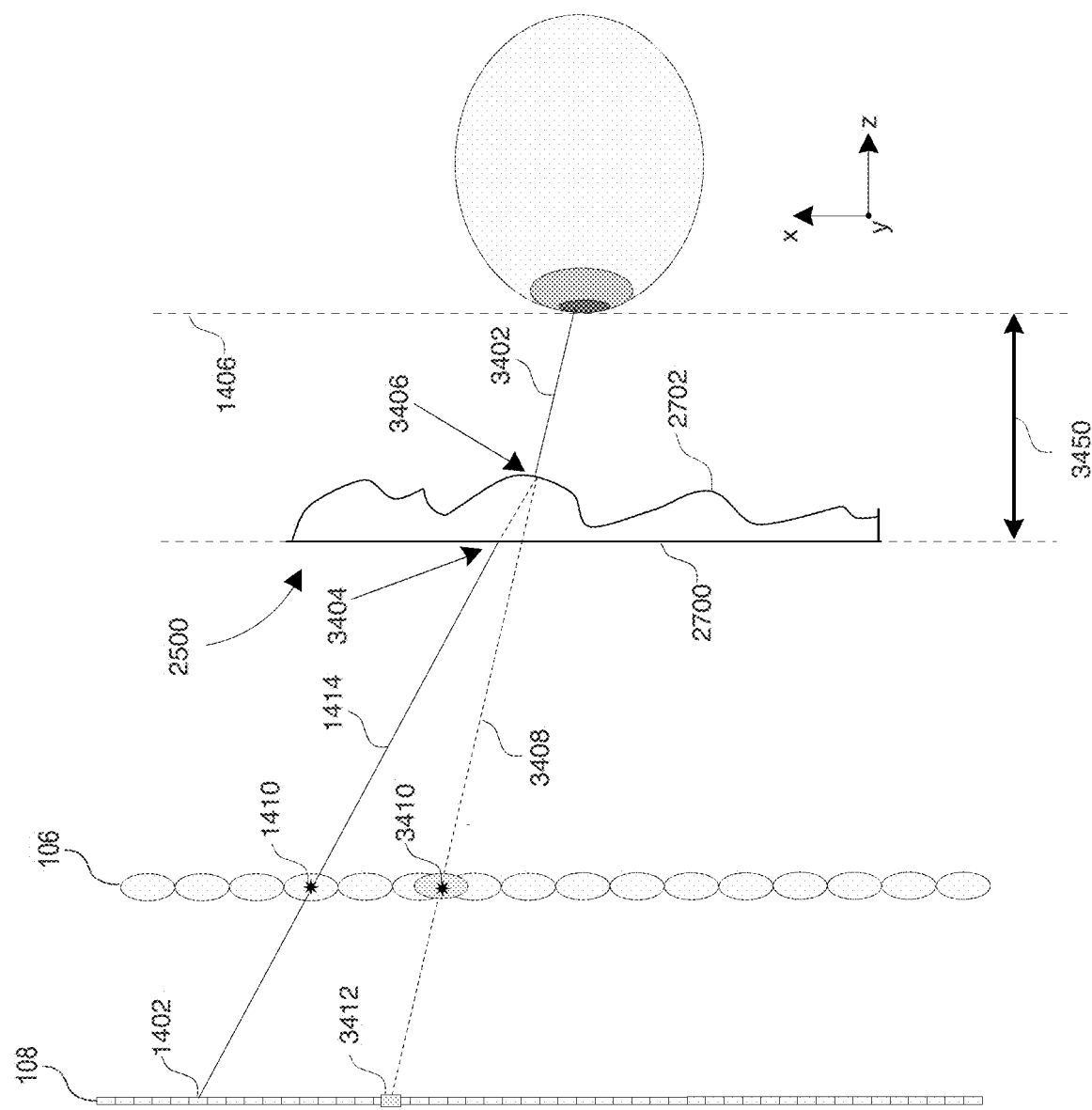
FIG. 34 is a schematic diagram illustrating certain process steps of FIGS. 35 and 38, in accordance with one embodiment.

This is schematically illustrated in FIG. 34, where phase element 2500 is shown to be located somewhere between the eye and the light field display. Thus, in this example, first surface 2700 is shown being located at a distance 3450 from pupil plane 1406. In the case where the eye itself is being modelled, then distance 3450 would be zero and first surface 2700 would be at pupil plane 1406. In addition, ray 1414 is shown encountering a first surface 2700 of a phase element 2500 at input location 3404, which produces a corresponding refracted ray 3402 exiting from second surface 2702 at output location 3406. Thus, at sub-step 3504, both the origin and orientation of refracted ray 3402 exiting phase element 2500 is computed. It is this ray that is propagated.

The skilled technician will understand that, at sub-step 3504, different methods or algorithms may be used to compute the origin and orientation of refracted ray 3402 coming out of the second surface 2702 of phase element 2500. In general, this involves computing a refraction event via electromagnetic wave propagation equations or Snell's law for each surface. However, in some embodiments, different approximations may be used to minimize the computational load of such computations.

Figure 36A:
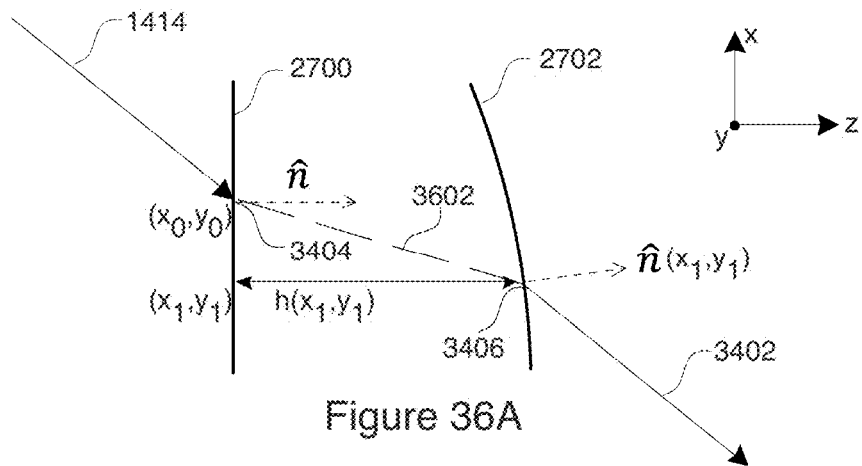
FIGS. 36A to 36C are schematic diagrams illustrating certain process steps of FIG. 35, in accordance with one embodiment.

As shown schematically in FIG. 36A, in the currently discussed embodiment (where first surface 2700 is flat and the second surface 2702 has a changing profile $h(x,y)$), incoming ray 1414 will intersect the first surface 2700 at input location 3404 (herein corresponding to x, y coordinates $(x_0,y_0)$, be refracted as ray 3602, which will travel within phase element 2500 until it reaches second surface 2702 at output location 3406 (herein corresponding to x, y coordinates $(x_1,y_1)$), where it will once again be refracted. The location in z of output location 3406 is given by the height or thickness profile function at this point, i.e. $h(x_1,y_1)$. Refracted ray 3402 is thus the refracted ray or ray vector exiting phase element 2500 at output point 3406.

In this exemplary embodiment, the normal vector $\hat{n}$ to first surface 2700 is by definition parallel to the z-axis, while the normal vectors of the second surface 2702 are defined as a function of x, y coordinates: $\hat{n}(x,y)$, as was discussed above. Thus, in FIG. 36A, the normal vector at second surface 2702 is given by $\hat{n}(x_1,y_1)$.

As mentioned above, different methods or techniques may be used to efficiently compute the refraction events illustrated in FIG. 36A. Some examples are discussed below.

In the most computationally demanding example, ray 3602 is projected forward within phase element 2500 using small propagation steps until the height or thickness traversed is equal or larger than the height or thickness at the current iteration, at which point the second refraction event is computed. However, this requires the use of small steps and thus many iterations may be required.

Figure 36B:
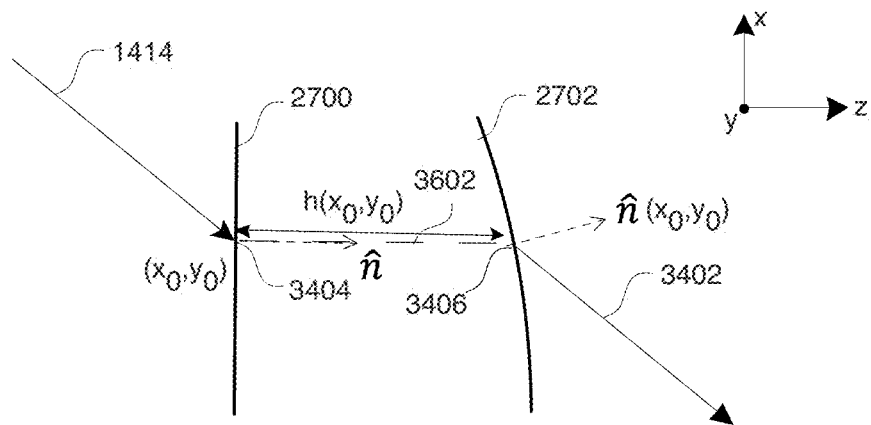

In one exemplary approximation, illustrated schematically in FIG. 36B, for a substantially thin phase element, output location 3406 may be approximated (e.g. thin lens approximation) as being the same as input location 3404 (i.e. $(x_0,y_0)$). Thus, the corresponding z-coordinate and normal vectors are given by $h(x_0,y_0)$ and normal vector $\hat{n}(x_0,y_0)$.

Figure 36C:
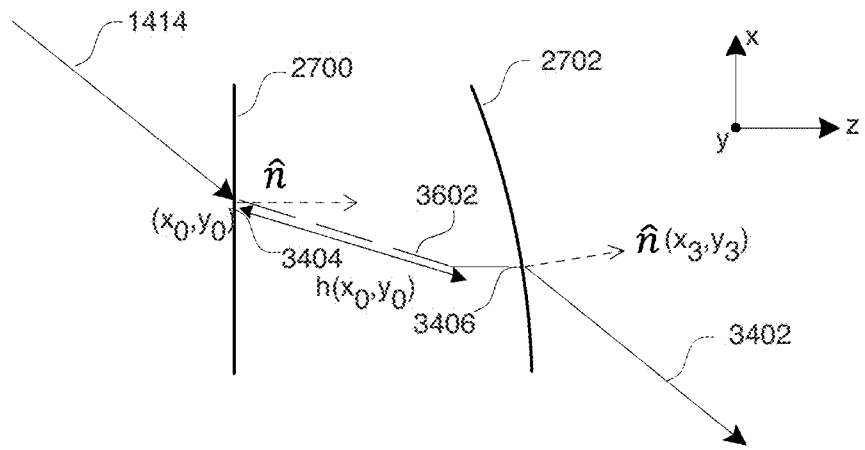

In another example, as illustrated in FIG. 36C, ray 3602 may be propagated inside phase element 2500 a distance equal to the height or thickness at the first intersection position $h(x_0,y_0)$ and then the normal vector at the new coordinates $(x_3,y_3)$ may be used to compute the second refraction event.

Figure 37A:
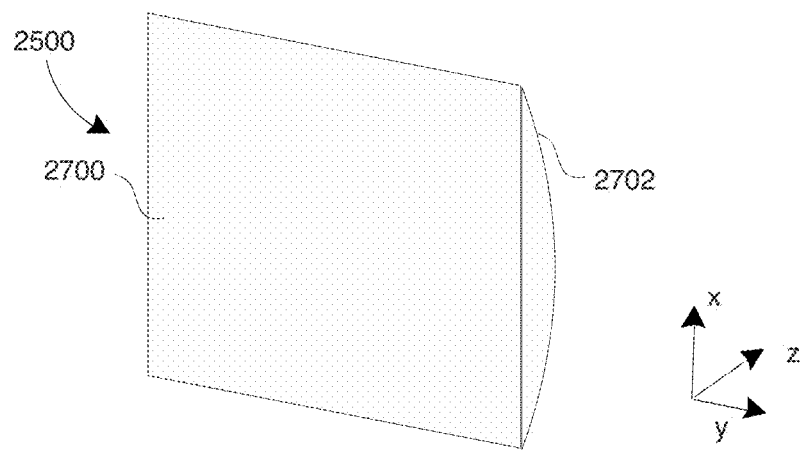
FIGS. 37A to 37C are schematic diagrams illustrating a phase element defined as a pre-computed set of height values and normal vectors, in accordance with one embodiment.
Figure 37B:
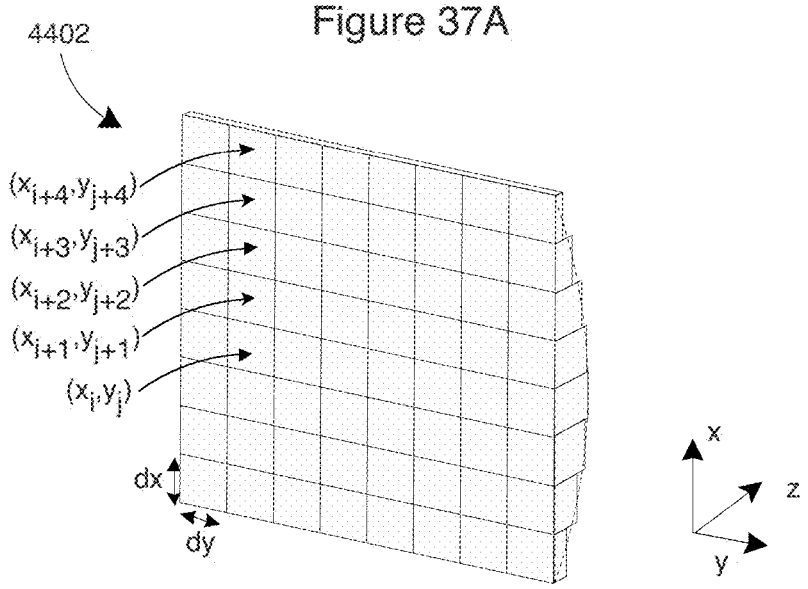
Figure 37C:
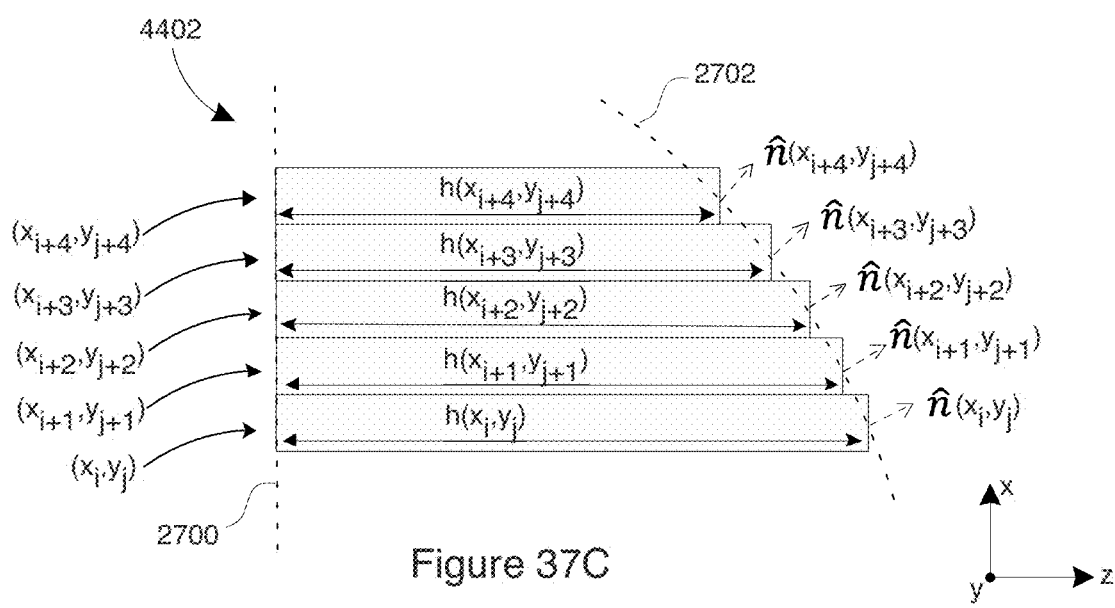

In addition, as mentioned above, in some embodiments, the values of functions $h(x,y)$ and $\hat{n}(x,y)$ may be pre-computed and stored in an array-like data structure, for example in a texture file. An example is given schematically in FIGS. 37A to 37C. Thus, the exemplary phase element 2500 of FIG. 37A (herein shown to have a rectangular shape as an example only to better illustrate) may be stored as a pre-computed array of height or thickness values herein represented as digitized phase element 4402 in FIG. 37B. Thus, each portion (i,j) (i.e. array index number) corresponds to a given height value $h(i,j)$ and normal vector $\hat{n}(i,j)$. The resolution of phase element 4402 may be changed as required by computational considerations, thus varying the corresponding size of each portion (dx,dy). FIG. 37C shows a cross-sectional view of FIG. 37B superimposed on the surfaces 2700 and 2702 of the exemplary phase element of FIG. 37A. In the case where the values are stored within a texture data structure, each portion corresponds to a texel (texture pixel) or similar and thus a corresponding (x,y) coordinate (for example input location (x,y) located within a given portion may be converted to the appropriate index (i,j) to access the corresponding height and normal vector).

In some embodiments, interpolated values for the height and normal vector may be generated as a function of the relative position of input location (x,y) with respect to the neighboring texel locations. This may include for example linear interpolation but other interpolation methods may also be used.

In some embodiments, the pre-computed set of values $h(i,j)$ may be sorted from smallest to largest, and then checked iteratively while propagating ray 3602 until the height or thickness at the newly obtained (x,y) coordinates is within a given tolerance interval.

Notably, as illustrated in FIG. 34, refracted ray 3402 will be perceived by the user, via projection 3408, as originating from a "virtual" optical element center 3410 (e.g. "virtual" lenslet or microlens center position) and corresponding "virtual" pixel 3412. As will be discussed further below, in some embodiments, each set of "virtual" pixel 3412 and associated "virtual" optical element center 3410 computed from each pixel in the pixel display, as discussed above, may be computed once and kept or stored in memory for later iterations.

Going back to FIG. 35, once a first refracted ray 3402 has been computed, the ray is propagated once more via sub-step 3502 until it encounters another phase element 2500 or until it reaches the pupil. Thus, in the case where multiple phase elements 2500 are present between the pupil plane 1406 and the LFSL 108, sub-steps 3502, 3503 and 3504 may be repeated as many times as necessary. Each time, the last refracted ray 3402 is used to compute the next refraction event. It is to be understood that the refracted ray 3402 that reaches the pupil plane 1406 is the one resulting from the last refraction event (e.g. last execution of sub-step 3504).

When, at sub-step 3503, refracted ray 3402 (or ray 1414 if no phase element 2500 has been encountered thus far) reaches the pupil plane 1406, the method proceeds to sub-step 3506 where a check is made that the intersection point of ray (1414 or 3502) on pupil plane 1406 is still within the pupil entrance, just like in step 1108 of method 1100 for example. If this is not the case, then the user cannot see the ray and step 2908 exits with a NO condition, so that method 2900 proceeds to step 1110 in FIG. 29. In the opposite case, then a final check is made at sub-step 3508 to see if a phase element 2500 has been placed at the pupil plane itself (to model an aberrated or visually compensated eye). If so, then sub-step 3510 proceeds just like sub-step 3504 and the new refracted ray 3402 is computed, just as discussed above. If no phase element was present at the pupil plane at sub-step 3508, or when the new refracted ray 3402 is computed at sub-step 3510, step 2908 exits with the YES condition, so that in method 2900 of FIG. 29, the method then proceeds to step 2912.

Figure 38:
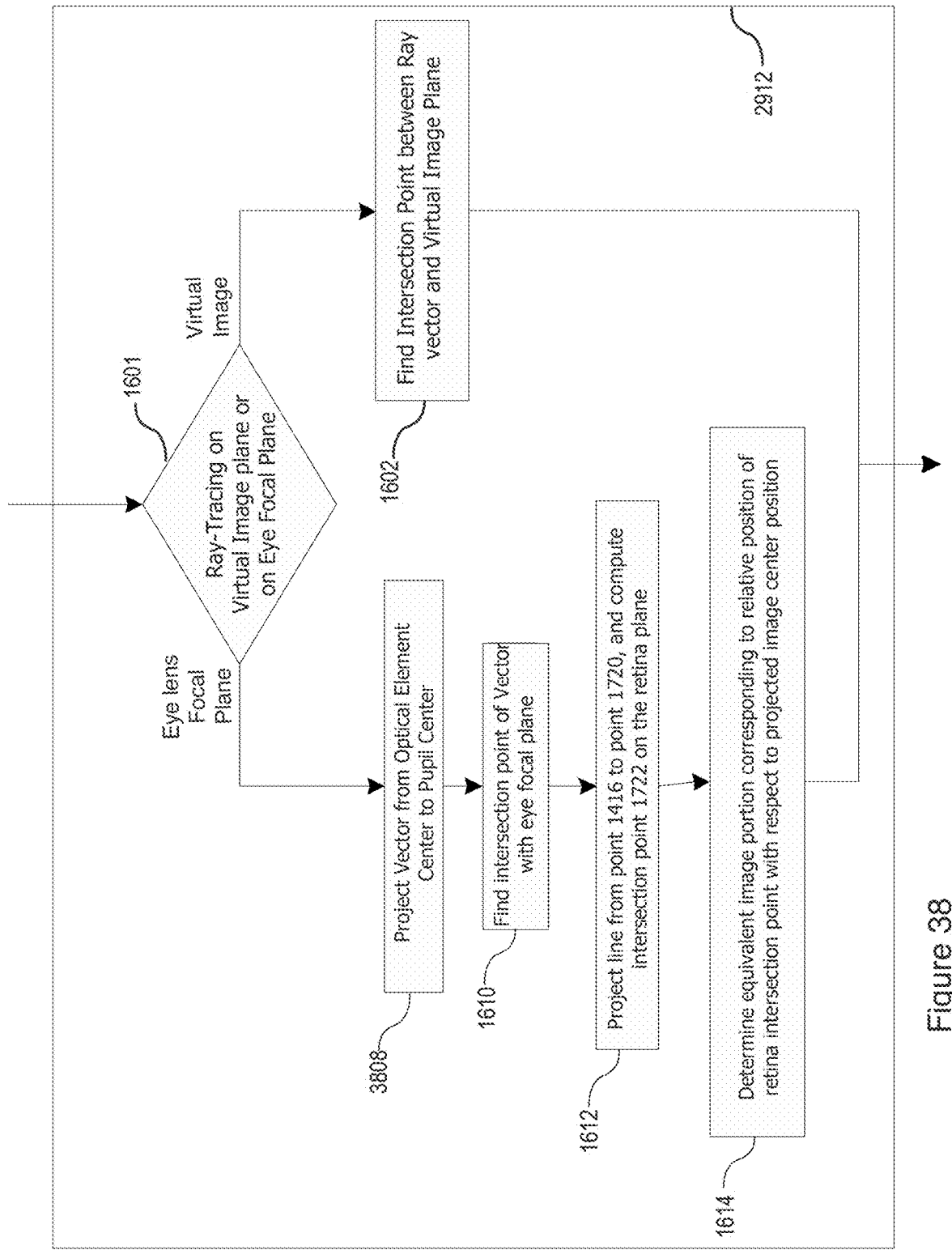
FIG. 38 is a process flow diagram illustrating certain process steps of FIG. 29, in accordance with one embodiment.

There, the last computed refracted ray 3402 (and its projection 3408 and "virtual" optical element center location 3410) may be used to replace ray 1414 in step 2912, which is illustrated in FIG. 38 and comprises the same sub-steps as step 1112 of FIG. 16, but with some changes, as will be discussed below.

Thus, step 2912 proceeds via sub-step 1601 as discussed above where the path changes depending on whether the ray-tracing is done on the virtual image plane or on the retinal plane. If it's the former, then sub-step 1602 is executed to identify the image portion on virtual image plane 1502, just like as described above in the context of FIG. 16, but here it is the intersection point of projection vector 3408 on virtual image plane 1502 (instead of vector 1504) which provides the corresponding image portion 1506 in FIG. 15.

In contrast, if at sub-step 1601 ray-tracing is done on the retinal plane, then sub-step 3808 is executed. Here, instead of using the real optical element center location 1410 to draw vector 1718 through pupil center 1022, it is instead the "virtual" optical element center location 3410 that is used instead. Thus, the ray-tracing steps illustrated in FIGS. 17A to 17D apply equally here as well, with the exception that point 1410 in FIG. 17A is replaced by point 3410. Thus, in FIG. 38, sub-steps 1610 to 1614 proceed as explained above to identify the image portion 1724.

Going back to FIG. 29, once step 2912 is finished and the corresponding image portion identified, steps 1114, 1116 and 1118 proceed just like in method 1100.

With reference to FIGS. 39 to 43, and in accordance with one exemplary embodiment, a modified version of method 2900 for correcting or compensating for HOAs but also operable to render multiple images or image portions on multiple adjusted distinct image planes simultaneously, generally referred to using the numeral 3900, will now be discussed.

Method 3900 is to method 2900 what the steps discussed above and illustrated in FIGS. 20A to 23B were for method 1100: it allows the light field display to render multiple optotypes or images simultaneously at different correction levels. In this exemplary embodiment, method 3900 as discussed below further includes the possibility of using multiple phase elements, but here wherein one distinct phase element is used for each image or optotype being rendered, and wherein each element has its own optical properties and thus simulates a different set of HOAs (or aberrations in general). Each set of HOAs (or aberrations in general) may also be defined via its own set of Zernike coefficients 1036. Thus, multiple corrections to HOAs (or aberrations in general) may be rendered simultaneously in different image portions or distinct optotypes side-by side. Usually, each set of HOAs may also be used in conjunction with a corresponding spherical dioptric power 1026, which will be used to define either a corresponding virtual image plane 1502 or an eye focal plane 1716, depending on the ray-tracing path chosen.

Figure 39:
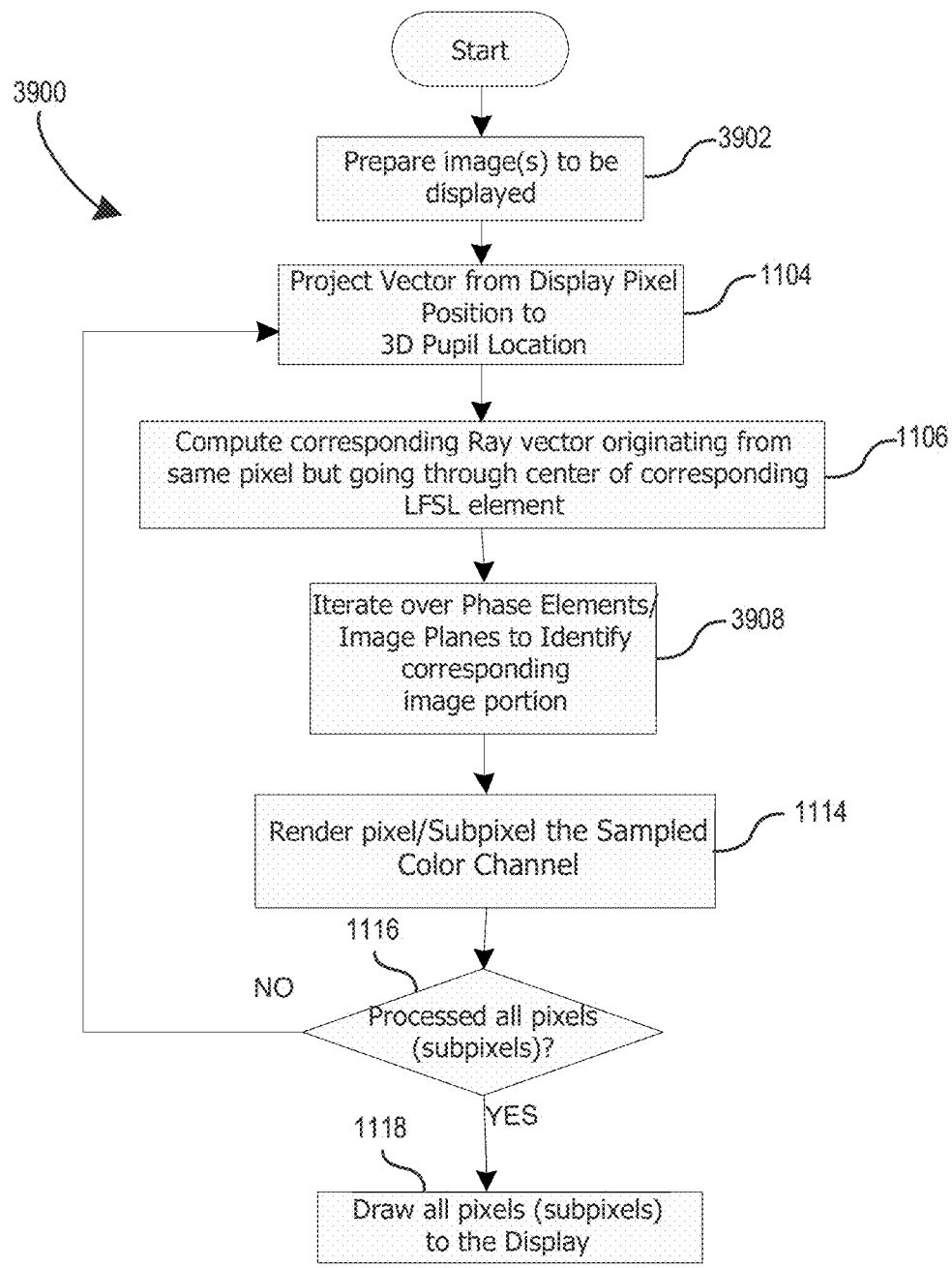
FIG. 39 is a process flow diagram of an illustrative ray-tracing rendering process for rendering simultaneously multiple images or optotypes compensating for different sets of HOAs, in accordance with one embodiment.
Figure 40A:
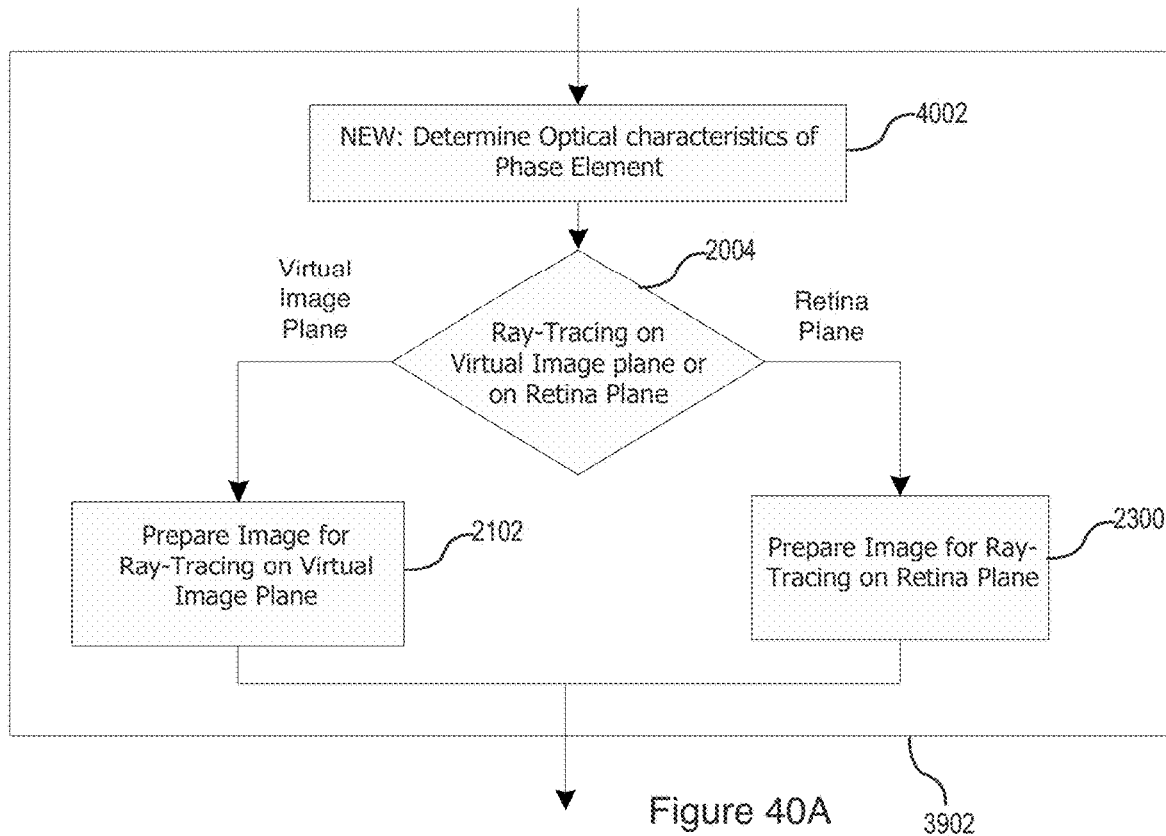
FIGS. 40A and 40B are process flow diagrams illustrating certain process steps of FIG. 39, in accordance with one embodiment.
Figure 40B:
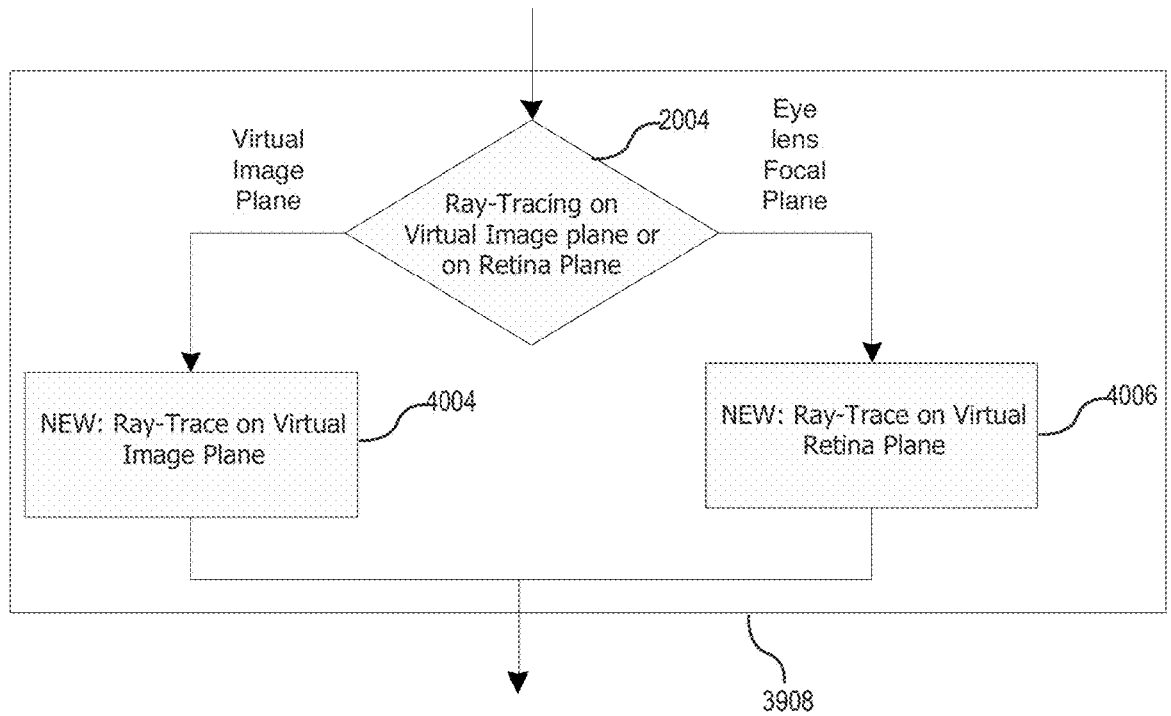
Figure 41:
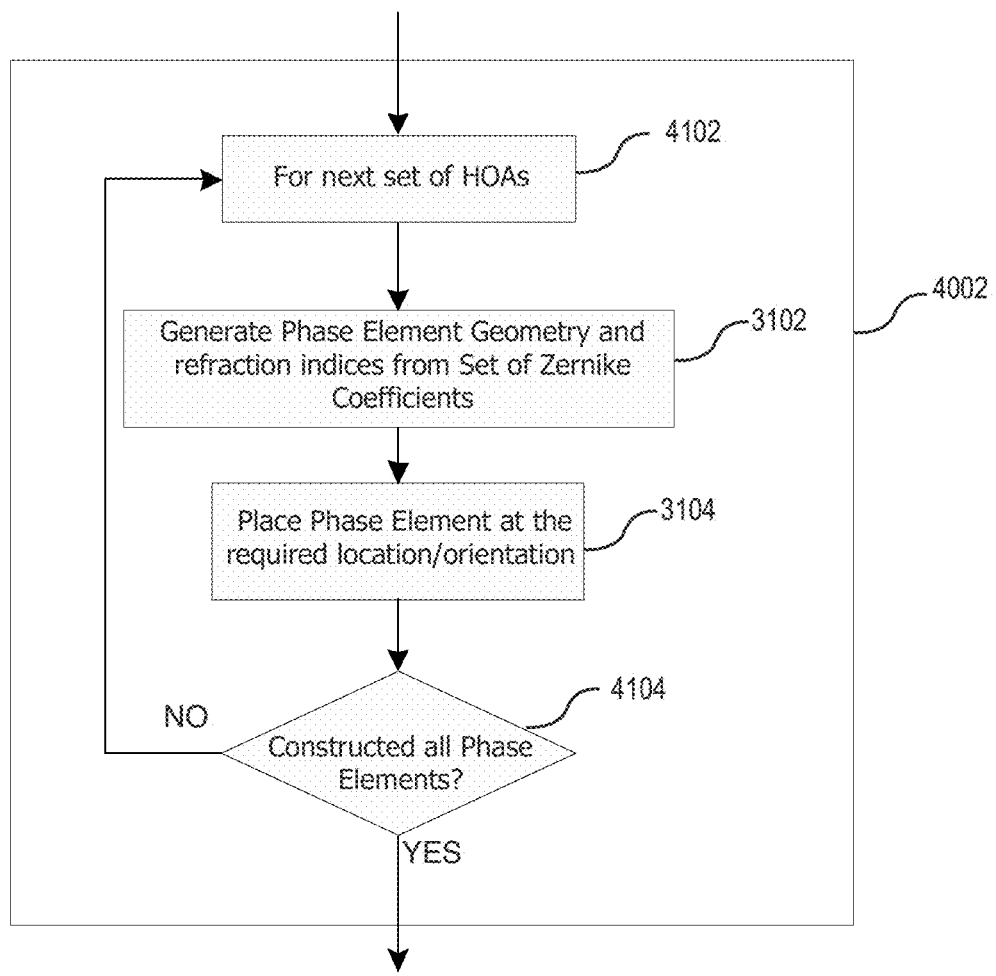
FIG. 41 is a process flow diagram illustrating certain process steps of FIG. 40A, in accordance with one embodiment.

Thus, in FIG. 39, method 3900 begins with step 3902, which mirrors in part step 2002 of FIG. 20A. However, as illustrated in FIG. 40A, step 3902 further includes, prior to sub-step 2400, sub-step 4002 where multiple phase elements may be constructed (for example one for each optotype being rendering simultaneously). Sub-step 4002 is illustrated in the process flow diagram of FIG. 41, where at sub-step 4102 a corresponding correction for a given set of HOAs (or aberrations in general) (for a given image portion or optotype) is selected (and its corresponding set of Zernike coefficients 1036). Then this set of Zernike coefficients is used to generate and place a corresponding phase element 2500 in sub-step 3102 and 3104 as discussed above. Then at sub-step 4104, if other sets of HOAs (or aberrations in general) are to be included, the method goes back iteratively to sub-step 4002 as many times as necessary, until all corresponding phase elements have been generated. Going back to FIG. 40A, after sub-step 4002, steps 2004, 2102 and 2300 proceed just as described above for each virtual image plane (sub-step 2102) or eye focal plane (sub-steps 2300).

Figure 42:
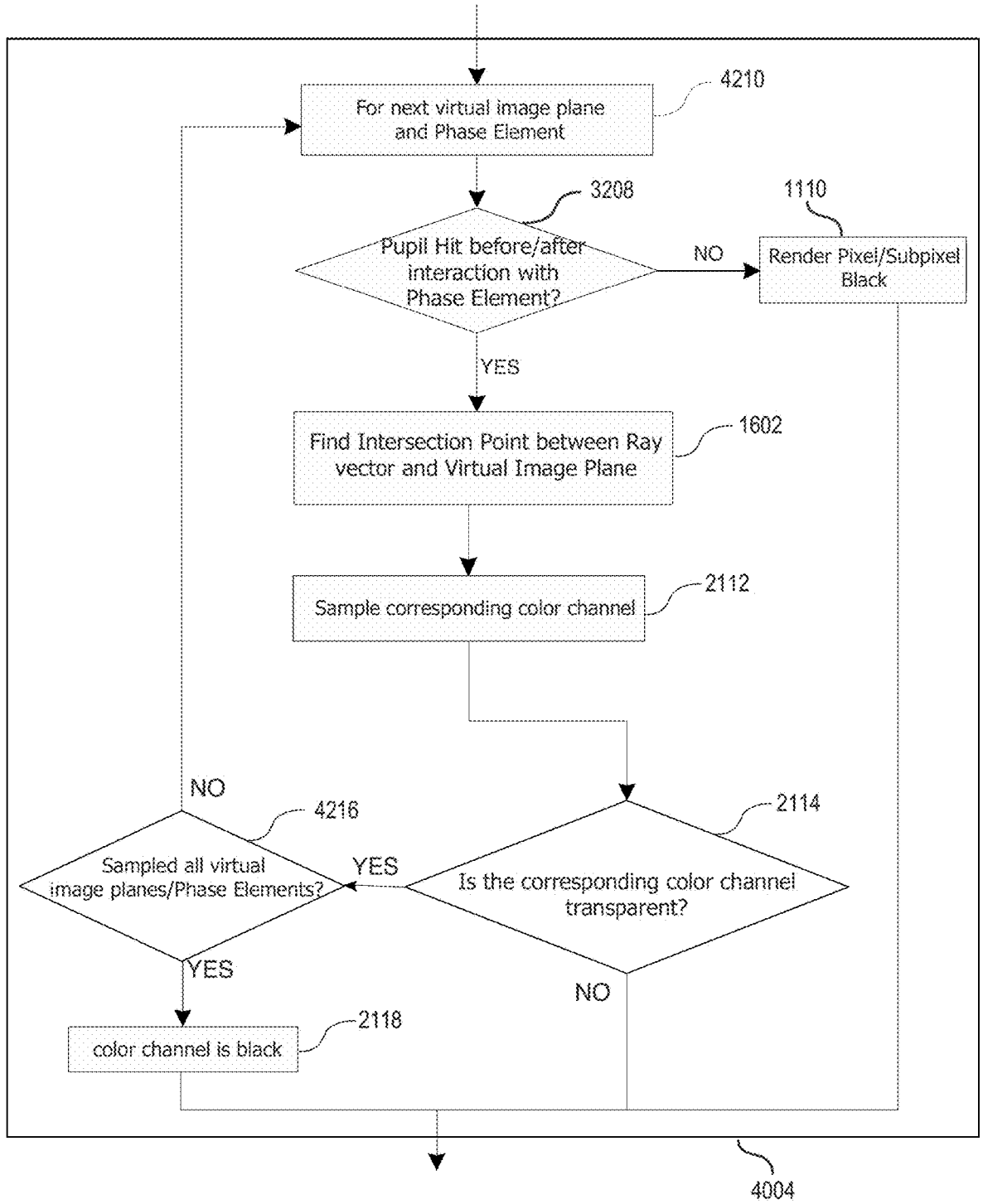
FIG. 42 is a process flow diagram illustrating certain process steps of FIG. 40B, in accordance with one embodiment.
Figure 43:
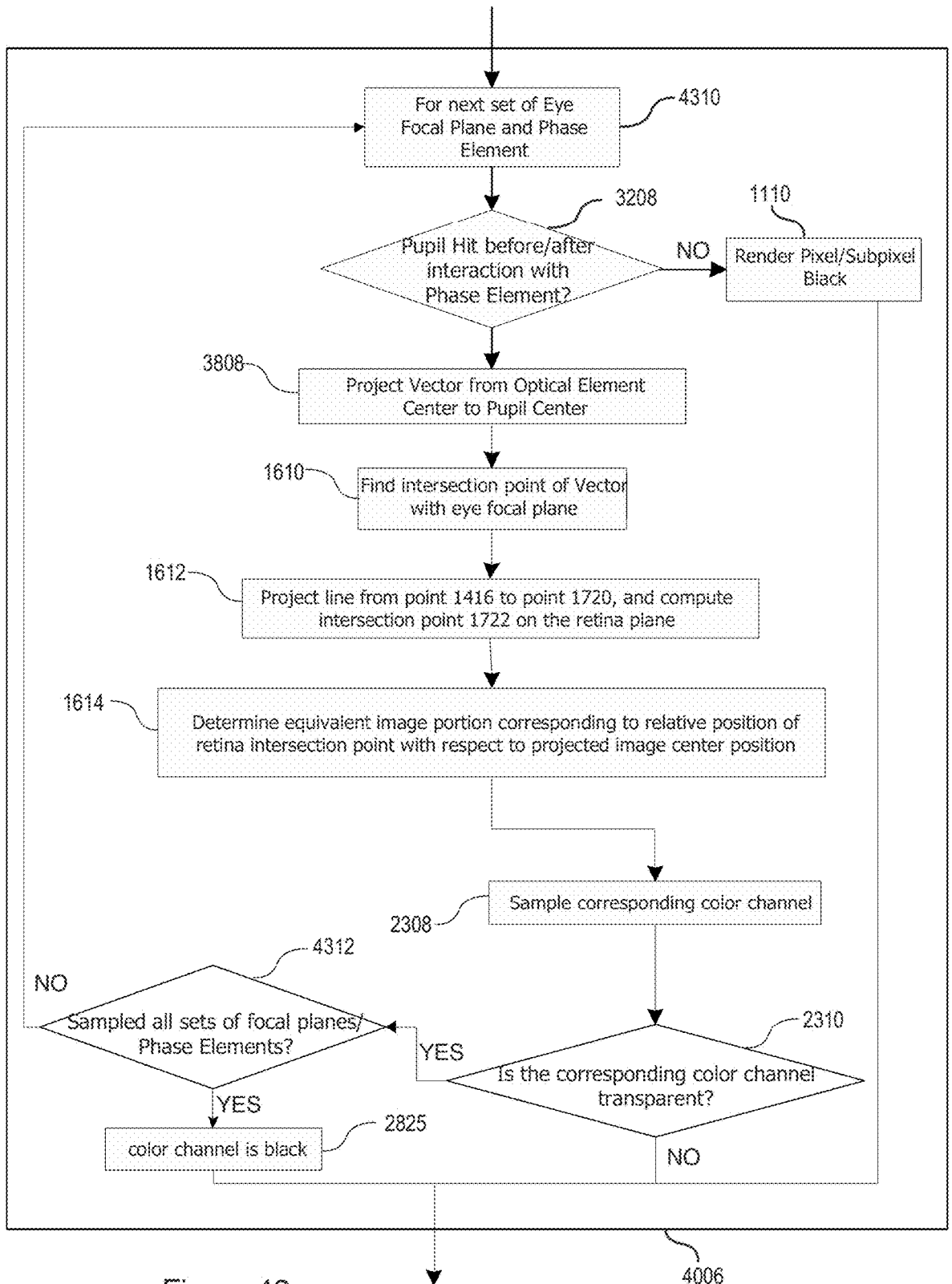
FIG. 43 is a process flow diagram illustrating certain process steps of FIG. 40B, in accordance with one embodiment.

Going back to FIG. 39, the iteration over each pixel proceed as before, via steps 1104 and 1106 discussed above. Then at step 3908, which is further illustrated in FIG. 40B, if at sub-step 2004 ray-tracing is done using virtual image planes, then the method proceeds to sub-step 4004, which is illustrated in FIG. 42, while if ray-tracing proceeds on the retinal plane, the method continues proceeds with sub-step 4006, which is illustrated in FIG. 43.

In the former case (virtual image planes), in some embodiments, sub-step 3810 is similar to step 2104 of FIG. 21B, but includes at sub-step 4210 a loop not only over corresponding spherical dioptric power 1026 values but also over associated (if any) HOAs and their corresponding phase element. So, once a combination of virtual image plane and phase element is selected, the method uses these to execute sub-step 3208, as described above. If, as computed within sub-step 3208, the ray (either ray 1414 or refracted ray 3402) does not reach inside the user pupil, then the method goes to sub-step 1110, described above. In contrast, if the ray does reach within the pupil, then the method proceeds with sub-step 1602 as discussed above, wherein the image portion on the virtual image plane is identified. Then the color channel of this image portion is identified at sub-step 2112, as before. Then, at sub-step 2114, as discussed before, if the channel is transparent, then a check is made if all combinations of virtual image planes and phase elements have been used at sub-step 4216, if not then the method goes back to sub-step 4210. If, at sub-step 4216 all combinations have been used and no non-transparent color channel has been encountered, then the method goes to sub-step 2118, as discussed above, so that the color is set to black (or another background color).

Going back to FIG. 40, if at sub-step 2004 ray-tracing is selected to be done on retina plane 1702 instead, then sub-step 4006 is executed. Flow process diagram of FIG. 43 illustrated one embodiment of sub-step 4006. Similarly, to sub-step 4004, a loop is executed over all sets of spherical dioptric power 1026 values but also over corresponding associated (if any) HOAs and their corresponding phase element at sub-step 4310. Then, sub-step 3208 is executed just as described above, and thus includes refraction by the corresponding phase element 2500 but also a check on whether the ray (either ray 1414 or refracted ray 3402, depending on the location of this particular phase element 2500) hits inside the pupil opening. If not, then step 1110 is executed as discussed above. If it does hit within the pupil opening, then steps 3808, 1610, 1612 and 1614 are executed one after the other as discussed above in the context of FIG. 38, where the "virtual" optical unit center location 3410 is used instead of the optical unit center location 1410 to draw vector 1718. Once the correct image portion has been identified at sub-step 1614, then step 2308 is executed to assign the corresponding colour channel to pixel 1402. Then sub-step 2310 is executed where, as explained above, the colour channel is checked to see if it has been defined as transparent. If it is not, then the colour value is retained and sub-step 4006 is exited. If it is transparent, then the step 4312 is executed to see if all of the corresponding sets of eye focal planes and phase elements have been iterated upon. If not, then the method goes back to sub-step 4310 with the next eye focal plane and phase element. If no phase element and eye focal plane is left, then sub-step 2825 is executed as described before, so that the corresponding colour channel is set to black (or another background colour), before exiting sub-step 4006.

Going back to FIG. 39, once step 3908 is finished, at step 1114 (described above) colour channel is assigned to pixel 1402. Steps 1116 (check if all pixels or sub-pixels have been processed) and 1118 (wherein the image is rendered via pixel display 110) proceed as explained before.

Figure 45:
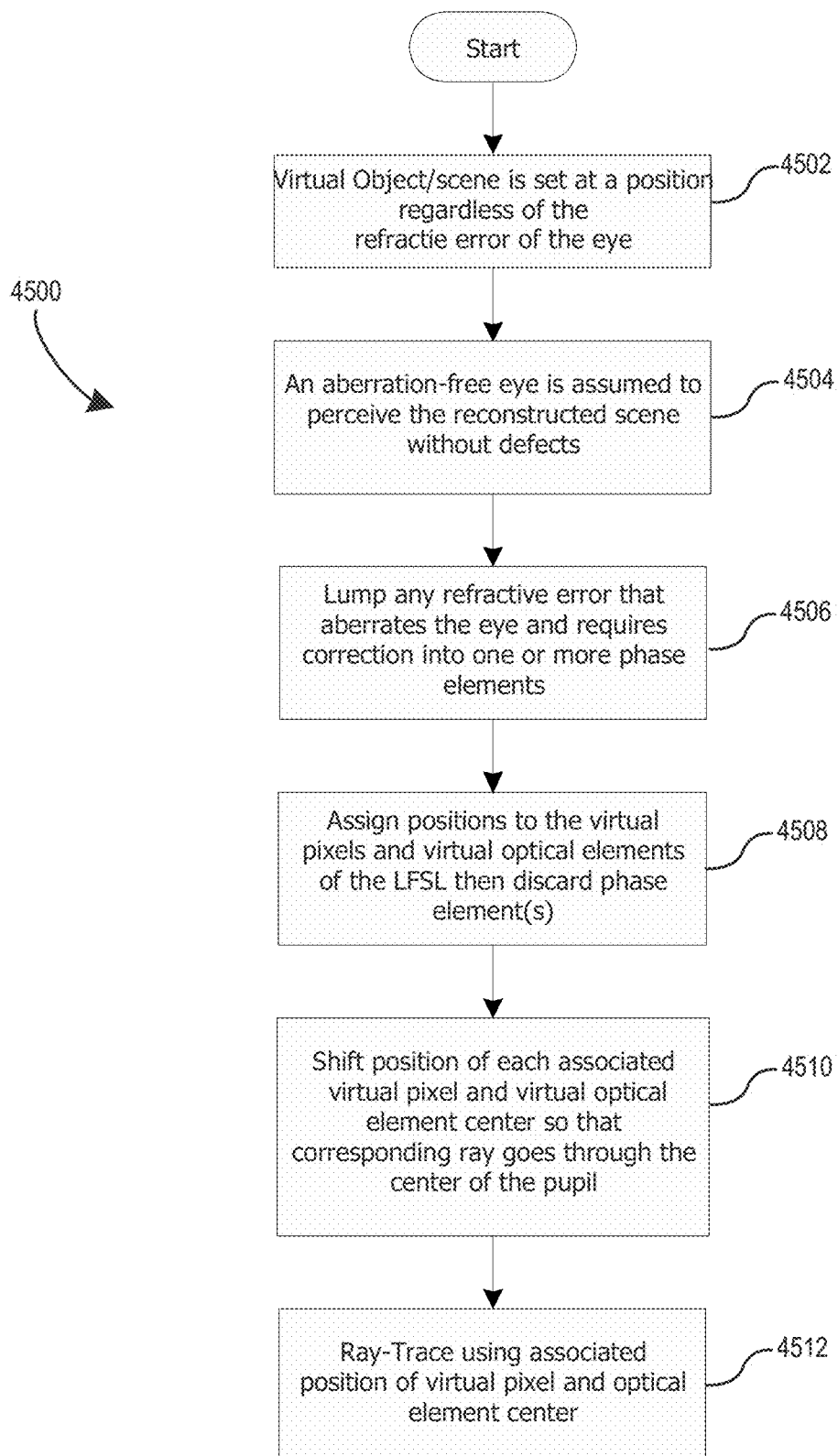
FIG. 45 is a process flow diagram illustrating an exemplary unified light field rendering method incorporating phase elements, in accordance with one embodiment.

With reference to FIG. 45, and in accordance with one exemplary embodiment, a unified light field rendering method incorporating phase elements, generally referred to using the numeral 4500, will now be described. Generally, this method is used to project a scene from a light field display using the "virtual" pixel and optical unit center (i.e. like "virtual" pixel 3412 and an associated "virtual" optical unit center 3410 discussed above and with reference to FIG. 34).

The method is to be implemented without the need of transforming the projected scene to an image plane or projection on retina. The role of the light-field algorithm, here, is to sample the scene/virtual object using the generated rays after considering eye aberrations using the phase element. The retinal spot size and spacing control is to be handled with optics design to control the generated beam characteristics.

Thus, at step 4502, a virtual object/scene is set at a position regardless of the refractive error (e.g. aberration) of the user's eye. Then at step 4504, an aberration-free eye is assumed to perceive the reconstructed scene without defects. At step 4506, any refractive error that aberrates the eye and needs to be corrected via light field rendering is lumped into one or more phase elements 2500, as discussed above, each element having the required position and orientation.

At step 4508, for each pixel 1402 in pixel display 108, rays are propagated through the corresponding optical element center 1410 and refraction events from the one or more phase elements 2500 are computed to derive a final refracted ray (i.e. ray 3402 in FIG. 34).

Figure 46:
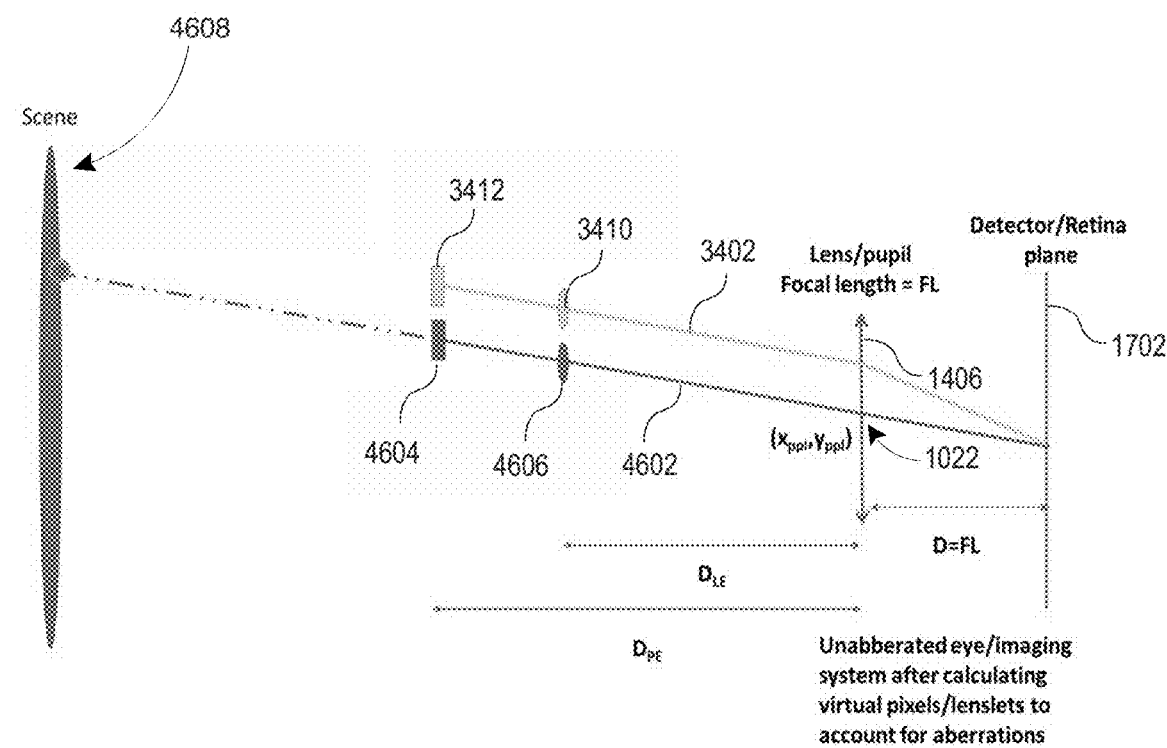
FIG. 46 is a schematic diagram illustrating certain process steps of the method of FIG. 45, in accordance with one embodiment.

At step 4510, each ray 3402 is shifted or translated to the nodal point of the eye lens (e.g. to cross pupil center location 1022 for example), as illustrated schematically in FIG. 46. There, we see a ray 3402 (with a corresponding virtual optical unit center location 3410 and associated virtual pixel location 3412) being shifted to intersect pupil center location 1022, thus giving ray 4602. By tracing back, another set of virtual pixel location 4604 and virtual optical unit center location 4606 may be found. In FIG. 46, $D_{LE}$ is the distance between the LFSL 106 and pupil plane 1406, D is the distance between the pupil and the retina (i.e. eye depth value 1034) which is assumed to be equal to the focal length (FL) of the aberration-free eye, and $D_{PE}$ is the distance between the pupil plane 1406 and the pixel display 106.

At step 4512, raytracing may be done, using different methods, such as method 1100 for example, by using virtual pixel location 4604 and virtual optical unit center location 4606 in place of the real pixel location and optical unit center location (thus using ray 4602 instead of ray 1414). Thus, ray 4602 may, for example, by projected backwards to a scene or object 4608 (i.e. for example like ray 1504 on virtual image plane 1502) to identify an corresponding image portion to be assigned to the corresponding pixel.

Below are some examples of how method 4500 may be applied to different situations:

Multiple Elements Treatment

For multiple elements with spatial offsets, method 4500 may be applied in a recursive manner or by full tracing of the beams generated by the lenslets-pixels combinations starting from the element closer to the lenslet ($D_{PO1}$ to $D_{PO3}$ in FIG. 44) and ending by the eye pupil, taking into account the required space transformation. For recursive implementation, the lenslets and pixel coordinates are updated after each iteration then the refracted phase element is removed for the following iteration. At the end of tracing, the virtual positions of lenslets and pixels are calculated, and light field raymarching is applied. For each phase element done with space transformation, inverse transformation can be done or the whole system is transformed including the virtual object all the way through.

Multi-Prescription Treatment

For a multi-prescription treatment, the scene objects/charts are sorted in space in the positions and scales they are desired to be viewed. For each prescription, a phase element is constructed, and virtual positions are calculated for the lenslets and pixels. Ray-tracing is done for each prescription/scene object combination. The pixels of rays that hit the prescription region being calculated are excluded from the following prescription calculation.

Progressive Depth Treatment

Elements like progressive lenses have different focal lengths at different regions on the lens element. For this kind of application, the phase element is constructed to correspond to refraction/phase profile of these elements then the regular procedure is applied as explained in steps 4502 to 4512 above.

Astigmatism

As noted above, the phase element method as described herein may be applied to address or test for visual acuity aberrations such as astigmatism. Likewise, while method 1100 as illustrated in FIGS. 11 to 17D is designed to correct for spherical aberrations, these methods may be expanded upon, for example, without use of the herein-described phase element approach, to also correct for astigmatism, or other visual aberrations. For example, Applicant's U.S. Pat.

No. 10,860,099 issued Dec. 8, 2020, details such an extended ray tracing approach for addressing astigmatism or similar conditions, the entire contents of which are hereby incorporated herein by reference.

For completeness, as described in this patent, and in accordance with one exemplary embodiment, a modified ray-tracing method similar to the method 1100 can be further operable to compensate or test for astigmatism. For example, in one approach, instead of using an initial fixed depth value for a virtual image plane derived from an input minimum reading distance (which implicitly implied spherical deficiency only), and use that value to place the virtual image plane at the correct location, a modified method instead proceeds to identify an intersection point on the pupil plane relative to an input cylinder axis angle, from which a combined spherical/cylindrical dioptric power or total dioptric power value may be derived. This total dioptric power may then be converted into a corresponding designated virtual image plane location for this iteration. Thus, image scaling on the virtual plane is not done once, but done on a per-pixel basis at each iteration.

As such, a total dioptric power comprising spherical and cylindrical contributions is computed as a function of the intersection point location on the pupil plane. In some embodiments, astigmatism may be modelled by considering that the eye is a sphero-cylindrical lens having a total refractive power along a given meridian angle θ given by:

$$P(\theta) = S + C \sin^2(\phi - \theta)$$

wherein P is the (total dioptric power), S is the spherical power 4001 (derived from an input or previously derived minimum reading distance, for example), C is the cylindrical power, φ the cylinder axis angle and θ is the angle of the position vector of a point on the pupil with respect to the x axis in a local pupil frame of reference.

Once the total dioptric power has been computed, it may be converted into a corresponding virtual image plane location/depth for the current pixel chosen. Therefore, each ray-tracing iteration will have its "own" corresponding virtual image plane at a potentially different location, depending on the value of the total dioptric power computed above.

In accordance with an alternative ray-tracing rendering process for astigmatism compensation, ray-tracing is otherwise implemented with respect to the eye focal plane. In particular, this approach takes into account combined effects of spherical dioptric power, cylindrical dioptric power, and cylinder axis angle variables to derive a location for an intersection point on this focal plane. Indeed, when considering spherical dioptric power only, the intersection point can be computed by drawing a line through the pupil center since for an ideal spherical lens, the ray going through the center will not be deviated by the refractive optics. Then it may be approximated that any other ray originating from the same pixel will converge on the same point on the focal plane. However, if instead of modelling the eye as a thin spherical lens but instead as a thin cylindrical lens, then in this case any ray originating from the same source or pixel along a meridian perpendicular to the cylinder axis of the cylindrical lens will converge on the same point on the focal plane along the main axis.

Thus, for the same intersection point, the point needed for drawing the straight line will have a different location along the cylinder axis. The two points identified above may be taken as extreme cases (i.e. purely spherical and purely cylindrical). Thus, if we consider a hybrid case of where the eye acts like a sphero-cylindrical lens combining the effects of a spherical lens with a cylindrical lens, that point will lie somewhere in-between those two extremum points on the cylinder axis. Accordingly, rays can be drawn through extremum points and the region along the cylinder axis on the pupil plane wherein a corresponding "offset" center pupil location is expected to be found.

Thus, a new step consists of locating an offset pupil center location within this range along the cylinder axis corresponding to an input value of the cylinder axis angle for the current pixel iteration. Once the offset pupil center location has been computed, remaining steps can be executed as above by replacing the pupil center location for the offset pupil center location to compute the location of the intersection point on the focal plane. As detailed above, these approaches may further be extended to render multiple images or optotypes simultaneously at different values of spherical dioptric power, cylindrical dioptric power, and/or cylinder axis angle.

In accordance with some embodiments, much as a complementary spherical lens, such as an electrically tunable fluid lens, may be used to extend the spherical compensation range produced via the light field display components of a subjective eye test device, as described herein, a further complementary optical refraction system may be deployed within the light field path to extend the cylindrical compensation range otherwise provided by this same light field rendering arrangement.

For example, a subjective eye test device comprising an array of digital pixels and a corresponding array of LFSEs, much as described above, may further include an adjustable refractive optical system interposed to intercept the dynamically adjustable light field to selectively produce a complementary visual acuity compensation to extend a compensation range otherwise available solely with the light field system. For example, as described above, a spherical compensation range may be extended using one or more (e.g. two stacked) tunable spherical lenses, such as an electrically tunable fluid lens, such that a coarse spherical compensation setting may be produced by this refractive optical system, whereas a fine-tuning around this coarse spherical compensation setting may be dynamically adjusted using the computationally adjustable light field system. As introduced above, and detailed below. A same or complementary refractive optical system may be deployed within the optical path to also or alternatively extend the cylindrical compensation range otherwise available solely with the light field system. For example, one or more tunable cylindrical optical elements may be interposed to set a coarse cylindrical compensation value, whereas the light field system may be computationally adjusted to fine tune a total cylindrical compensation around this coarse value. Accordingly, a total spherical and/or cylindrical compensation power may be decomposed to include both a compensation component produced by the adjustable refractive optical system, which may itself be decomposed between spherical and/or cylindrical optical elements, and the computationally adjusted light field system.

Likewise, for embodiments enabling the simultaneous projection of multiple or a same optotype for multiple distinct compensation values, a coarse spherical and/or cylindrical value may be applied uniformly to each optotype via the adjustable refractive optical system, whereas each of the multiple distinct compensation values may be simultaneously applied using the light field system within the dynamic range provided thereby, as described above. It will be appreciated that different testing sequences and/or approaches may be applied using this setup, such as, for example, first simultaneously invoking multiple spherical compensation values for comparative purposes until an optimal spherical value is subjectively identified, to be followed by various axis and/or cylindrical compensation comparison grids and/or sequences to subjectively assess an optimal cylindrical (and axis) compensation value based on a composition of light field and refractive cylindrical optical compensation values.

As noted, a dioptric correction range may be extended by incorporating additional or alternative optical components in the light path within a light field device. Moreover, the nature of the correction may be tuned based on the selection of appropriate optical component type. For example, one embodiment relates to the inclusion of cylindrical lenses to expand the cylindrical range of a light field device (e.g. a monocular or binocular refractor) by placing stacked cylindrical lenses at the exit aperture(s) of a monocular (or binocular) refractor. For example, stacked cylindrical lenses 4818, 4820 (e.g. in the binocular embodiment of FIG. 48) may be placed adjacent to (in front or behind) the tunable lens(es) 4814, 4816. The optical power of such components may be tuned, for instance, by imposing an angular offset between different cylindrical lenses axis meridian of a stack using, for instance, rotation adjustment means, such as motors.

Various configurations may be adopted to various effects depending on the application at hand. For example, one embodiment relates to disposing a double-stack of cylindrical lenses at each output aperture of a device, wherein each lens of the double-stack comprises the same optical power and optical power sign. Another embodiment relates to two double-stacks of cylindrical lenses comprising the same power magnitude and opposite signs.

Figure 47A:
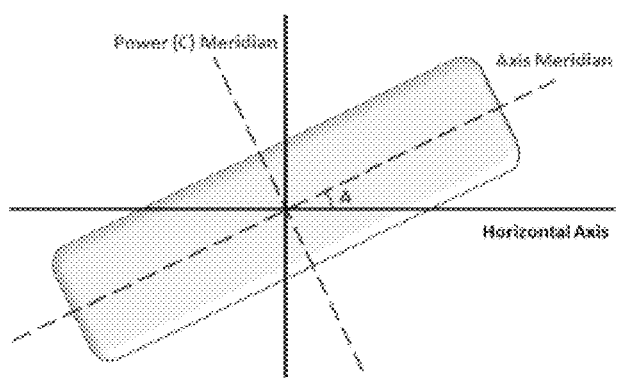
FIG. 47A is a schematic illustrating various aspects of a cylindrical lens, in accordance with various embodiments.
Figure 47B:
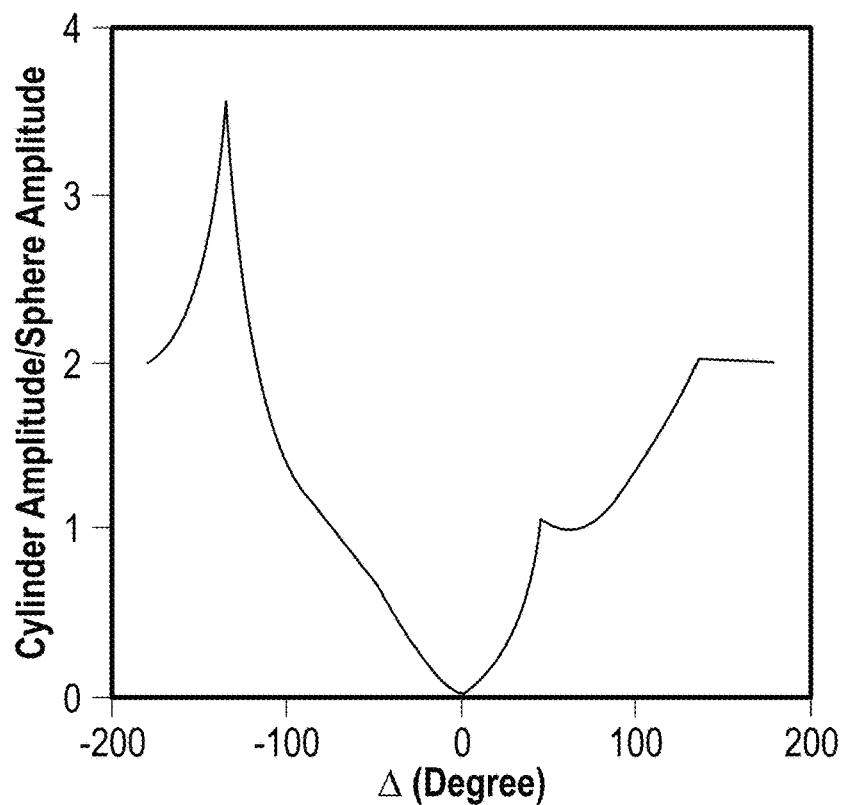
FIG. 47B is a plot of the ratio of spherical to cylindrical power amplitude as a function of angular offsets for an exemplary cylindrical lens stack for use in a subjective light field vision testing device, in accordance with various embodiments.
Figure 47C:
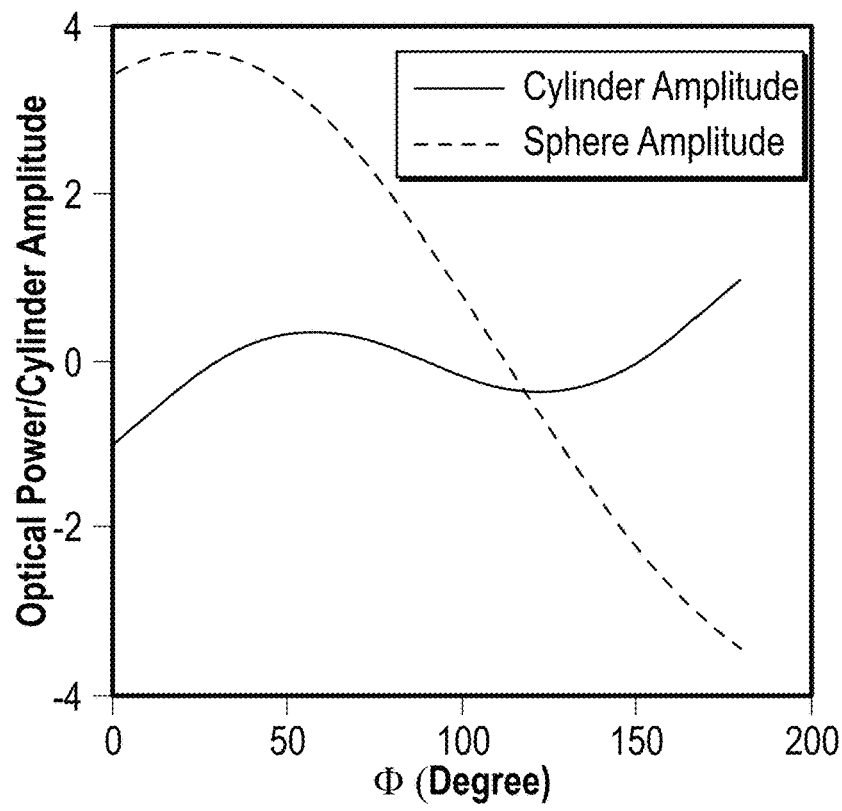
FIG. 47C is a plot of the normalised cylindrical and spherical powers for an exemplary cylindrical lens stack configuration for use in a subjective light field vision testing device, in accordance with various embodiments.

For further clarity, FIG. 47A is a schematic illustrating various aspects of a cylindrical lens. For such a cylindrical lens, the axis meridian is the meridian where the cylindrical power is zero. The power meridian (i.e. the axis along which 100% of the maximum cylindrical power is achieved), is oriented 90° from the axis meridian. Such concepts are typically applied with respect to conditions such as astigmatism, which is often reported in terms of the cylinder power at the power meridian and the axis meridian angle measured from horizontal axis.

To further elucidate how such concepts may be applied to increase dioptric ranges of a light field device as herein described, one may consider a ray position (x,y) and corresponding angle coordinates $(\alpha_x, \alpha_y)$ given by:

$$V = \begin{bmatrix} x \\ y \\ \alpha_x \\ \alpha_y \end{bmatrix}.$$

For a generic bi-cylindrical lens with the axis meridian aligned along the x-axis and characterised by a power $C_x$, and wherein the axis meridian is aligned along the y axis and is of power $C_y$, the transfer matrix is given by:

$$\overline{M_C} = \begin{bmatrix} 1 & 0 & 0 & 0 \\ 0 & 1 & 0 & 0 \\ -C_y & 0 & 1 & 0 \\ 0 & -C_x & 0 & 1 \end{bmatrix}.$$

For a rotation of $A=\varphi$ in counterclockwise direction from the +x axis, the rotation matrix is given by:

$$\overline{M_R(\varphi)} = \begin{bmatrix} Cos\varphi & Sin\varphi & 0 & 0 \\ -Sin\varphi & Cos\varphi & 0 & 0 \\ 0 & 0 & Cos\varphi & Sin\varphi \\ 0 & 0 & -Sin\varphi & Cos\varphi \end{bmatrix}.$$

Hence, the transfer matrix for a cylindrical lens with an axis meridian rotated by $\varphi$ is given by:

$$\overline{M_C(\varphi)} = \overline{M_R(-\varphi)} \cdot \overline{M_C}.$$

$$\overline{M_R(\varphi)} = \begin{bmatrix} 1 & 0 & 0 & 0 \\ 0 & 1 & 0 & 0 \\ -C_y Cos^2\varphi - C_x Sin^2\varphi & (-C_y + C_x)\frac{Sin2\varphi}{2} & 1 & 0 \\ (-C_y + C_x)\frac{Sin2\varphi}{2} & -C_y Sin^2\varphi - C_x Cos^2\varphi & 0 & 1 \end{bmatrix}.$$

For a double-stack of cylindrical lenses each characterised by a single axis of power $C_x$ and having meridians rotated by $$A = \pm\frac{\varphi}{2}$$

from the x axis, which relates to a total offset angle of $\varphi$ between the lens axis meridians, the transfer matrix is given by:

$$\overline{M_{Cx}\left(\frac{\varphi}{2}\right)M_{Cx}\left(-\frac{\varphi}{2}\right)} =$$

$$\begin{bmatrix} 1 & 0 & 0 & 0 \\ 0 & 1 & 0 & 0 \\ -2C_s Sin^2\frac{\varphi}{2} & 0 & 1 & 0 \\ 0 & -2C_x Cos^2\frac{\varphi}{2} & 0 & 1 \end{bmatrix} = \begin{bmatrix} 1 & 0 & 0 & 0 \\ 0 & 1 & 0 & 0 \\ 2C_x Cos\varphi & 0 & 1 & 0 \\ 0 & 0 & 0 & 1 \end{bmatrix}$$

$$\begin{bmatrix} 1 & 0 & 0 & 0 \\ 0 & 1 & 0 & 0 \\ -2C_x Cos^2\frac{\varphi}{2} & 0 & 1 & 0 \\ 0 & -2C_x Cos^2\frac{\varphi}{2} & 0 & 1 \end{bmatrix} =$$

$$\begin{bmatrix} 1 & 0 & 0 & 0 \\ 0 & 1 & 0 & 0 \\ 0 & 0 & 1 & 0 \\ 0 & -2C_x Cos\varphi & 0 & 1 \end{bmatrix} \begin{bmatrix} 1 & 0 & 0 & 0 \\ 0 & 1 & 0 & 0 \\ -2C_x Sin^2\frac{\varphi}{2} & 0 & 1 & 0 \\ 0 & -2C_x Sin^2\frac{\varphi}{2} & 0 & 1 \end{bmatrix}.$$

The last two equalities represent a decomposition into pure cylindrical (first bracketed term) and spherical (second bracketed term) components. These components relate to optical power of equal amplitudes, corresponding to half of the power range, as a function of the angular offset.

Hence, two cylindrical lenses of positive or negative 1.5 diopters can be added within a light field device to obtain a 6-diopter cylindrical correction range. Rotating lenses to obtain $\varphi$ values between 0 and $\pi$ yields cylindrical corrections between −3 and 3 diopters. This configuration also corresponds to a maximum spherical shift of a 3-diopter magnitude that can be compensated for by adjusting the spherical range, in accordance with one embodiment, or by inserting, for instance, an additional spherical tunable lens, in accordance with another embodiment, to compensate for the spherical shift in accordance with the characterization outlined above. Further, the meridian angle may be set to the designated angle by rotating both lenses simultaneously.

In accordance with another embodiment, the spherical shift may be minimized through the employ of a stack of positive and negative cylindrical lenses. For instance, for two double stacks having angular offsets of φ and Δ−φ and opposite powers, the ratio of spherical to cylindrical power amplitude can be calculated as a function of Δ. This is presented in the plot of FIG. 37B, where this ratio is maximised for a Δ value of −135°. FIG. 37C shows the normalized cylindrical and spherical powers as a function of φ for this Δ value of −135°. For this value, the cylindrical range of −3 to 3 diopters is yielded using two positive and two negative cylindrical lenses of an optical power of ~0.88 diopters, in accordance with one embodiment. The maximum amplitude shift in spherical power for this exemplary embodiment is ~0.88 diopters. It is further noted that for Δ=180°, which may be implemented using, for instance, Jackson cross cylinders, the cylinder-to-sphere amplitude ratio is 2, which is comparable to using a single stack of two positive or negative cylindrical lenses, as described above.

The relationship between the stacked cylindrical lenses power and the obtained cylindrical and spherical power shifts is linear. Therefore, it will be appreciated that the cylindrical expansion can be scaled by one-to-one factor relationship. For instance, in the previous example the range can be doubled to 12 diopters (−6 diopters to 6 diopters) by doubling the power magnitude of the cylindrical lens components to 3 diopters in the first exemplary embodiment and ~1.76 diopters in the second exemplary embodiment. Again, the cylindrical range expansion is determined in compromise with the spherical shift that can be compensated or scarified since the spherical shift is one-to-one dependent on the chosen cylindrical expansion range. It will be appreciated that other lens configurations are also considered, in accordance with other embodiments.

While the present disclosure describes various embodiments for illustrative purposes, such description is not intended to be limited to such embodiments. On the contrary, the applicant's teachings described and illustrated herein encompass various alternatives, modifications, and equivalents, without departing from the embodiments, the general scope of which is defined in the appended claims. Except to the extent necessary or inherent in the processes themselves, no particular order to steps or stages of methods or processes described in this disclosure is intended or implied. In many cases the order of process steps may be varied without changing the purpose, effect, or import of the methods described.

Information as herein shown and described in detail is fully capable of attaining the above-described object of the present disclosure, the presently preferred embodiment of the present disclosure, and is, thus, representative of the subject matter which is broadly contemplated by the present disclosure. The scope of the present disclosure fully encompasses other embodiments which may become apparent to those skilled in the art, and is to be limited, accordingly, by nothing other than the appended claims, wherein any reference to an element being made in the singular is not intended to mean "one and only one" unless explicitly so stated, but rather "one or more." All structural and functional equivalents to the elements of the above-described preferred embodiment and additional embodiments as regarded by those of ordinary skill in the art are hereby expressly incorporated by reference and are intended to be encompassed by the present claims. Moreover, no requirement exists for a system or method to address each and every problem sought to be resolved by the present disclosure, for such to be encompassed by the present claims. Furthermore, no element, component, or method step in the present disclosure is intended to be dedicated to the public regardless of whether the element, component, or method step is explicitly recited in the claims. However, that various changes and modifications in form, material, work-piece, and fabrication material detail may be made, without departing from the spirit and scope of the present disclosure, as set forth in the appended claims, as may be apparent to those of ordinary skill in the art, are also encompassed by the disclosure.

What is claimed is:

1. A subjective eye test device comprising:
an array of digital display pixels;
a corresponding array of light field shaping elements (LFSEs) disposed to shape a light field emanating from said pixels toward a user pupil location;
a hardware processor operable on pixel data for a defined optotype to output adjusted pixel data to be rendered via said LFSEs to adjust perception of said defined optotype at the user pupil location within a range of visual acuity compensations, wherein said range of visual acuity compensations comprises a cylindrical compensation range and a spherical compensation range; and
an adjustable refractive optical system interposed to intercept said light field and adjustable to selectively produce a complementary visual acuity compensation to extend each of said cylindrical compensation range and said spherical compensation range;
wherein said hardware processor and said adjustable refractive optical system are operable to adjust said perception of said defined optotype until an optimal spherical visual acuity compensation and an optimal cylindrical visual acuity compensation are subjectively identified.

2. The device of claim 1, wherein said adjustable refractive optical system comprises an electrically tunable lens.

3. The device of claim 2, wherein said electrically tunable lens comprises a pair of spherically tunable lenses.

4. The device of claim 1, wherein said adjustable refractive optical system comprises a tunable cylindrical lens tunable to extend said cylindrical compensation range.

5. The device of claim 4, wherein said tunable cylindrical lens comprises a pair of cylindrical lenses, wherein an angular offset of said pair of cylindrical lenses is tunable to extend said cylindrical compensation range.

6. The device of claim 1, wherein said adjustable refractive optical system is operable to set a coarse visual acuity compensation value within a broader course visual acuity compensation range, whereas said hardware processor is operable to fine-tune said coarse visual acuity compensation value within a narrower visual acuity compensation range around said coarse visual acuity compensation value until said optimal spherical and cylindrical visual acuity compensation is subjectively identified.

7. The device of claim 6, wherein said adjustable refractive optical system comprises an adjustable spherical lens to set a coarse spherical visual acuity compensation and an adjustable cylindrical lens to set a coarse cylindrical visual acuity compensation.

8. The device of claim 6, wherein a total visual acuity compensation power is composed of a coarse visual acuity compensation power produced by said adjustable refractive optical system, and a fine visual acuity compensation power produced by said hardware processor operating on said pixel data.

9. The device of claim 6, wherein said hardware processor is operable on said pixel data to simultaneously render at least two said defined optotype side-by-side in accordance with respective visual acuity compensations within said narrower visual acuity compensation range for subjective comparison.

10. The device of claim 9, wherein said at least two said defined optotype are rendered to present distinct levels of correction for a same optotype.

11. The device of claim 1, wherein said defined optotype comprises multiple optotypes varying in size and displayed simultaneously according to a same visual acuity compensation.

12. The device of claim 1, wherein said optimal cylindrical visual acuity compensation compensates for astigmatism.

* * * * *